United States Patent
Dahl et al.

(10) Patent No.: US 9,457,036 B2
(45) Date of Patent: *Oct. 4, 2016

(54) COMPOSITIONS AND METHODS FOR COMBINATION ANTIVIRAL THERAPY

(71) Applicant: Gilead Sciences, Inc., Foster City, CA (US)

(72) Inventors: Terrence C. Dahl, Sunnyvale, CA (US); Mark M. Menning, San Francisco, CA (US); Reza Oliyai, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 14/523,758

(22) Filed: Oct. 24, 2014

(65) Prior Publication Data

US 2015/0111855 A1 Apr. 23, 2015

Related U.S. Application Data

(63) Continuation of application No. 14/227,653, filed on Mar. 27, 2014, which is a continuation of application No. 12/204,174, filed on Sep. 4, 2008, now Pat. No. 8,716,264, which is a continuation of application No. 10/540,794, filed as application No. PCT/US2004/000832 on Jan. 13, 2004, now abandoned.

(60) Provisional application No. 60/440,246, filed on Jan. 14, 2003, provisional application No. 60/440,308, filed on Jan. 14, 2003.

(51) Int. Cl.

| | | |
|---|---|---|
| *A01N 43/54* | (2006.01) | |
| *A61K 31/505* | (2006.01) | |
| *A61K 31/675* | (2006.01) | |
| *A61K 31/513* | (2006.01) | |
| *A61K 31/7076* | (2006.01) | |
| *A61K 45/06* | (2006.01) | |
| *A61K 31/683* | (2006.01) | |
| *A61K 9/20* | (2006.01) | |

(52) U.S. Cl.
CPC .......... *A61K 31/675* (2013.01); *A61K 9/2009* (2013.01); *A61K 9/2013* (2013.01); *A61K 9/2018* (2013.01); *A61K 9/2054* (2013.01); *A61K 9/2059* (2013.01); *A61K 31/513* (2013.01); *A61K 31/683* (2013.01); *A61K 31/7076* (2013.01); *A61K 45/06* (2013.01)

(58) Field of Classification Search
None
See application file for complete search history.

(56) References Cited

U.S. PATENT DOCUMENTS

| | | |
|---|---|---|
| 3,524,846 A | 8/1970 | Moffatt et al. |
| 3,622,677 A | 11/1971 | Short et al. |
| 3,682,930 A | 8/1972 | Bourquin et al. |
| 3,994,974 A | 11/1976 | Murakami et al. |
| 4,003,878 A | 1/1977 | Skaar et al. |
| 4,258,062 A | 3/1981 | Jonas et al. |
| 4,355,032 A | 10/1982 | Verheyden et al. |
| 4,384,005 A | 5/1983 | McSweeney |
| 4,430,343 A | 2/1984 | Iemura et al. |
| 4,476,248 A | 10/1984 | Gordon et al. |
| 4,724,233 A | 2/1988 | De Clercq et al. |
| 4,808,716 A | 2/1989 | Holy et al. |
| 4,816,570 A | 3/1989 | Farquhar |
| 4,879,288 A | 11/1989 | Warawa et al. |
| 4,935,507 A | 6/1990 | Takaya et al. |
| 4,957,924 A | 9/1990 | Beauchamp |
| 4,968,788 A | 11/1990 | Farquhar |
| 5,047,407 A | 9/1991 | Belleau et al. |
| 5,075,445 A | 12/1991 | Jarvest et al. |
| 5,142,051 A | 8/1992 | Holy et al. |
| 5,151,426 A | 9/1992 | Belleau et al. |
| 5,155,268 A | 10/1992 | Hester |

(Continued)

FOREIGN PATENT DOCUMENTS

| | | |
|---|---|---|
| EP | 0 182 024 A2 | 5/1986 |
| EP | 0 206 459 A2 | 12/1986 |

(Continued)

OTHER PUBLICATIONS

Gild—Gilead Sciences Conference Call to Discuss Triangle Pharmaceuticals Acquisition dated Dec. 4, 2002, Ristig et al. (Tenofovir Disoproxil Fumarate, TDF) Therapy for Chronic Hepatitis B in Human Immunodeficiency Virus/Hepatitis B Virus—Coinfected Individuals for Whom Interferon-alpha and Lamivudine Therapy Have Failed, JID 2002; 186 pp. 1844-1847.*

Memorandum Opinion and Order Construing Patent Claims, signed by Judge Irene M. Keeley, Case No. 1:14-cv-00099-IMK (Dated: May 12, 2015), 44 pages.

(Continued)

*Primary Examiner* — Alton Pryor
(74) *Attorney, Agent, or Firm* — Cooley LLP

(57) ABSTRACT

The present invention relates to therapeutic combinations of [2-(6-amino-purin-9-yl)-1-methyl-ethoxymethyl]-phosphonic acid diisopropoxycarbonyloxymethyl ester (tenofovir disoproxil fumarate, Viread®) and (2R,5S,cis)-4-amino-5-fluoro-1-(2-hydroxymethyl-1,3-oxathiolan-5-yl)-(1H)-pyrimidin-2-one (emtricitabine, Emtriva™, (−)-cis FTC) and their physiologically functional derivatives. The combinations may be useful in the treatment of HIV infections, including infections with HIV mutants bearing resistance to nucleoside and/or non-nucleoside inhibitors. The present invention is also concerned with pharmaceutical compositions and formulations of said combinations of tenofovir disoproxil fumarate and emtricitabine, and their physiologically functional derivatives, as well as therapeutic methods of use of those compositions and formulations.

16 Claims, No Drawings

(56) References Cited

U.S. PATENT DOCUMENTS

| | | |
|---|---|---|
| 5,177,064 A | 1/1993 | Bodor |
| 5,179,104 A | 1/1993 | Chu et al. |
| 5,204,466 A | 4/1993 | Liotta et al. |
| 5,208,221 A | 5/1993 | Kim et al. |
| 5,210,085 A | 5/1993 | Liotta et al. |
| 5,386,030 A | 1/1995 | Kim et al. |
| 5,432,172 A | 7/1995 | Kashman et al. |
| 5,453,503 A | 9/1995 | Aikins et al. |
| 5,466,806 A | 11/1995 | Belleau et al. |
| 5,476,938 A | 12/1995 | Vemishetti et al. |
| 5,486,520 A | 1/1996 | Belleau et al. |
| 5,506,347 A | 4/1996 | Erion et al. |
| 5,512,596 A | 4/1996 | Kim et al. |
| 5,514,557 A | 5/1996 | Moghaddam |
| 5,514,798 A | 5/1996 | Bischofberger et al. |
| 5,519,021 A | 5/1996 | Payne et al. |
| 5,538,975 A | 7/1996 | Dionne |
| 5,587,480 A | 12/1996 | Belleau et al. |
| 5,618,820 A | 4/1997 | Dionne |
| 5,618,964 A | 4/1997 | Cheng et al. |
| 5,627,186 A | 5/1997 | Cameron et al. |
| 5,663,159 A | 9/1997 | Starrett, Jr. et al. |
| 5,696,254 A | 12/1997 | Mansour et al. |
| 5,733,788 A | 3/1998 | Bischofberger |
| 5,744,596 A | 4/1998 | Mansour et al. |
| 5,756,706 A | 5/1998 | Mansour et al. |
| 5,763,606 A | 6/1998 | Mansour et al. |
| 5,792,756 A | 8/1998 | Starrett, Jr. et al. |
| 5,798,340 A | 8/1998 | Bischofberger et al. |
| 5,814,639 A | 9/1998 | Liotta et al. |
| 5,859,021 A | 1/1999 | Cameron et al. |
| 5,905,082 A | 5/1999 | Roberts et al. |
| 5,914,331 A | 6/1999 | Liotta et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 6,043,230 A | 3/2000 | Arimilli et al. |
| 6,057,305 A | 5/2000 | Holy et al. |
| 6,069,249 A | 5/2000 | Arimilli et al. |
| 6,069,252 A | 5/2000 | Liotta et al. |
| 6,113,920 A | 9/2000 | Maye et al. |
| 6,114,343 A | 9/2000 | Liotta et al. |
| 6,121,315 A | 9/2000 | Nair et al. |
| 6,180,639 B1 | 1/2001 | Coates et al. |
| 6,194,391 B1 | 2/2001 | Schinazi et al. |
| 6,312,662 B1 | 11/2001 | Erion et al. |
| 6,417,191 B1 | 7/2002 | Barry et al. |
| 6,639,071 B2 | 10/2003 | Thompson et al. |
| RE38,333 E | 11/2003 | Arimilli et al. |
| 6,642,245 B1 | 11/2003 | Liotta et al. |
| 6,703,396 B1 | 3/2004 | Liotta et al. |
| 6,812,233 B1 | 11/2004 | Liotta |
| 6,939,964 B2 | 9/2005 | Thompson et al. |
| 7,094,413 B2 | 8/2006 | Buelow et al. |
| 7,795,217 B2 | 9/2010 | Adra |
| 7,851,165 B2 | 12/2010 | Fuhrmann et al. |
| 8,067,473 B2 | 11/2011 | Alchanati et al. |
| 8,592,397 B2 | 11/2013 | Dahl et al. |
| 8,598,185 B2 * | 12/2013 | Dahl et al. ............... 514/263.32 |
| 8,716,264 B2 * | 5/2014 | Dahl et al. ...................... 514/81 |
| 8,871,271 B2 | 10/2014 | Dahl et al. |
| 2001/0012518 A1 | 8/2001 | Makooi-Morehead et al. |
| 2001/0014352 A1 | 8/2001 | Batra et al. |
| 2003/0203969 A1 | 10/2003 | Bevec et al. |
| 2004/0180089 A1 | 9/2004 | Plachetka et al. |
| 2004/0224917 A1 | 11/2004 | Dahl et al. |
| 2004/0253218 A1 | 12/2004 | Eisenbach-Schwartz et al. |
| 2005/0197320 A1 | 9/2005 | Chen et al. |
| 2006/0128692 A1 | 6/2006 | Chen et al. |
| 2006/0246130 A1 | 11/2006 | Dahl et al. |
| 2007/0036861 A1 | 2/2007 | Oury et al. |
| 2007/0077295 A1 | 4/2007 | Dahl et al. |
| 2007/0099902 A1 | 5/2007 | Dahl et al. |
| 2009/0036408 A1 | 2/2009 | Dahl et al. |
| 2009/0143314 A1 | 6/2009 | Dahl et al. |
| 2014/0037732 A1 | 2/2014 | Dahl et al. |
| 2014/0213556 A1 | 7/2014 | Dahl et al. |
| 2014/0370102 A1 | 12/2014 | Dahl et al. |

FOREIGN PATENT DOCUMENTS

| | | |
|---|---|---|
| EP | 0 269 947 A1 | 6/1988 |
| EP | 0 369 409 A1 | 5/1990 |
| EP | 0 382 526 A2 | 8/1990 |
| EP | 0 481 214 A1 | 4/1992 |
| EP | 0 482 657 A2 | 4/1992 |
| EP | 0 595 635 | 5/1994 |
| EP | 0 632 048 A1 | 1/1995 |
| EP | 0 647 649 A1 | 4/1995 |
| EP | 0 694 547 A2 | 1/1996 |
| EP | 1 256 585 A1 | 11/2002 |
| EP | 1 332 757 A1 | 8/2003 |
| GB | 942 152 A | 11/1963 |
| GB | 1 523 865 A | 9/1978 |
| GB | 2 111 043 A | 6/1983 |
| WO | WO 88/05438 | 7/1988 |
| WO | WO 91/19721 A1 | 12/1991 |
| WO | WO 92/01698 | 2/1992 |
| WO | WO 92/09611 A1 | 6/1992 |
| WO | WO 92/13869 | 8/1992 |
| WO | WO 92/14743 * | 9/1992 |
| WO | WO 92/14743 A2 | 9/1992 |
| WO | WO 93/03027 A1 | 2/1993 |
| WO | WO 94/03466 | 2/1994 |
| WO | WO 94/03467 A2 | 2/1994 |
| WO | WO 95/07919 | 3/1995 |
| WO | WO 95/07920 A1 | 3/1995 |
| WO | WO 95/32957 A1 | 12/1995 |
| WO | WO 96/18605 A1 | 6/1996 |
| WO | WO 98/04569 A1 | 2/1998 |
| WO | WO 99/25352 A1 | 5/1999 |
| WO | WO 99/61026 | 12/1999 |
| WO | WO 00/16755 | 3/2000 |
| WO | WO 00/25797 A1 | 5/2000 |
| WO | WO 00/64427 A2 | 11/2000 |
| WO | WO 01/64221 A1 | 9/2001 |
| WO | WO 02/08241 A2 * | 1/2002 |
| WO | WO 02/062123 A2 | 8/2002 |
| WO | WO 02/068058 A2 | 9/2002 |
| WO | WO 02/070518 A1 | 9/2002 |
| WO | WO 03/045327 A2 | 6/2003 |
| WO | WO 03/059327 | 7/2003 |
| WO | WO 2004/052296 A2 | 6/2004 |
| WO | WO 2004/064845 A1 | 8/2004 |
| WO | WO 2005/021001 A1 | 3/2005 |
| WO | WO 2006/135933 A2 | 12/2006 |
| WO | WO 2006/135993 A2 | 12/2006 |
| WO | WO 2007/068934 A2 | 6/2007 |
| WO | WO 2012/068535 | 5/2012 |

OTHER PUBLICATIONS

Plaintiffs' Motion to Compel Defendants to Produce Documents, Case No. 1:14-cv-00099-IMK (Filed: May 28, 2015), 9 pages.
Plaintiffs' Response to Defendants' Pretrial Memrorandum filed by Bristol-Meyers, Squibb Company, Merck, Sharp &Dohme Corp., Case No. 1:10-cv-01851-RJS, (Filed May 28, 2013), 19 pages.
Affidavit of Paul A. Bartlett, Ph.D. filed by Emory University, Defendants' Memorandum of Law in Oppositon to Plaintiffs' Opening Pretrial Brief ffiled by Teva Pharmaceutical Industries, Ltd., Teva Pharmaceuticals USA, Inc., Case No. 1:10-cv-01851-RJS, (Filed May 28, 2013), 18 pages.
Stipulation and Order of Dismissal, Case No. 1:10-cv-01851-RJS (Dated Aug. 16, 2013), 2 pages.
Affidavit of Calvin J. Cohen, M.D. filed by Emory University, Gilead Sciences, Inc., Case No. Case: 1:08-cv-10838-RJS (Filed Sep. 9, 2013), 41 pages. Gilead Sciences, Inc.,Case No. 1:08-cv-10838-RJS (Filed Sep. 9, 2013), 39 pages.
Affidavit of Carlo-Federico Perno, M.D., Ph.D. filed by Emory University, Gilead Sciences, Inc.,Case No. 1:08-cv-10838-RJS (Filed Sep. 9, 2013), 50 pages.

(56) References Cited

OTHER PUBLICATIONS

Affidavit of Dennis C. Liotta, Ph.D. filed by Emory University, Gilead Sciences, Inc.,Case No. 1:08-cv-10838-RJS (Filed Sep. 9, 2013), 31 pages.
Affidavit of Judi Weissinger, Ph.D. filed by Emory University, Gilead Sciences, Inc.,Case No. 1:08-cv-10838-RJS (Filed Sep. 9, 2013), 13 pages.
Affidavit of Stephen G. Davies, Ph.D. filed by Emory University, Gilead Sciences, Inc.,Case No. 1:08-cv-10838-RJS (Filed Sep. 9, 2013), 42 pages.
Affidavit of Daniel C. Smith, Ph.D. filed by Emory University, Gilead Sciences, Inc.,Case No. 1:08-cv-10838-RJS (Filed Sep. 9, 2013), 31.
Affidavit of James Meyers filed by Emory University, Gilead Sciences, Inc.,Case No. 1:08-cv-10838-RJS (Filed Sep. 9, 2013), 15.
Plaintiffs' Pretrial Memorandum filed by Emory University, Gilead Sciences, Inc.,Case No. 1:08-cv-10838-RJS (Filed Sep. 9, 2013), 60 pages.
Plaintiffs' Proposed Findings of Fact and Conclusions of Law, filed by Emory University, Gilead Sciences, Inc.,Case No. 1:08-cv-10838-RJS (Filed Sep. 9, 2013), 85 pages.
Declaration of Harry Boghigian filed by Teva Pharmaceutical Industries Limited, Teva Pharmaceuticals USA, Inc., Case No. 1:08-cv-10838-RJS (Filed Sep. 9, 2013), 17 pages.
Declaration of Stanley Roberts, Ph.D., filed by Teva Pharmaceutical Industries Limited, Teva Pharmaceuticals USA, Inc., Case No. 1:08-cv-10838-RJS (Filed Sep. 9, 2013), 78 pages.
Defendants' Pretiral Memorandum filed by Teva Pharmaceutical Industries Limited, Teva Pharmaceuticals USA, Inc., Case No. 1:08-cv-10838-RJS (Filed Sep. 9, 2013), 47 pages.
Defendants' Proposed Findings of Fact and Conclusions of Law filed by Teva Pharmaceutical Industries Limited, Teva Pharmaceuticals USA, Inc., Case No. 1:08-cv-10838-RJS (Filed Sep. 9, 2013), 68 pages.
Affidavit of Dennis C. Liotta,Ph.D. filed by Emory University, Gilead Sciences, Inc. Case No. 1:08-cv-10838-RJS (Filed Sep. 19, 2013), 31 pages.
Affidavit of Stephen G. Davies, Ph.D. filed by Emory University, Gilead Sciences, Inc. Case No. 1:08-cv-10838-RJS (Filed Sep. 19, 2013), 42.
Plaintiffs' Pretrial Memorandum filed by Emory University, Gilead Sciences, Inc. Case No. 1:08-cv-10838-RJS (Filed Sep. 19, 2013), 60 pages.
Plaintiffs' Proposed Findings of Fact and Conculsions of Law filed by Emory University, Gilead Sciences, Inc. Case No. 1:08-cv-10838-RJS (Filed Sep. 19, 2013), 85 pages.
Defendants' Memorandum of Law in Opposition to Plantiffs' Pretrial Memorandum filed by Teva Pharmaceutical Industries Limited, Teva Pharmaceuticals USA, Inc., Case No. 1:08-cv-10838-RJS (Filed Sep. 23, 2013), 31 pages.
Plaintiffs' Opposition to Teva's Pretrial Memorandum, filed by Emory University, Gilead Sciences, Inc. Case No. 1:08-cv-10838-RJS (Filed Sep. 23, 2013), 41 pages.
Amendend Declaration of Stanley Roberts, Ph.D. filed by Teva Pharmaceutical Industries Limited, Teva Pharmaceuticals USA, Inc., Case No. 1:08-cv-10838-RJS (Filed Oct. 4, 2013), 77 pages.
Transcript of Proceedings regarding Trial held on Oct. 8, 2013 before Judge Richard J. Sullivan, Case No. 1:08-cv-10838-RJS (Dated Oct. 21, 2013), 222 pages.
Transcript of Proceedings regarding Trial held on Oct. 9, 2013 before Judge Richard J. Sullivan, Case No. 1:08-cv-10838-RJS (Dated Oct. 21, 2013), 220 pages.
Transcript of Proceedings regarding Trial held on Oct. 10, 2013 before Judge Richard J. Sullivan, Case No. 1:08-cv-10838-RJS (Dated Oct. 21, 2013), 38 pages.
Transcript of Proceedings regarding Trial held on Oct. 28, 2013 before Judge Richard J. Sullivan, Case No. 1:08-cv-10838-RJS (Dated Nov. 7, 2013), 67 pages.

Stipulated Statement of Corrections to Trial Transcript, Oct. 8-10, 28, 2013 filed by Emory University, Gilead Sciences, Inc. Case No. 1:08-cv-10838-RJS (Filed Dec. 4, 2013), 42 pages.
Plaintiffs' Post-Trial Brief filed by Emory University, Gilead Sciences, Inc. Case No. 1:08-cv-10838-RJS (Filed Dec. 4, 2013), 43 pages.
Defendants' Post-Trial Memorandum filed by Teva Pharmaceutical Industries Limited, Teva Pharmaceuticals USA, Inc., Case No. 1:08-cv-10838-RJS (Filed Dec. 4, 2013), 43 pages.
Defendants' Revised Proposed Findings of Fact and Conclusions of Law filed by Teva Pharmaceutical Industries Limited, Teva Pharmaceuticals USA, Inc., Case No. 1:08-cv-10838-RJS (Filed Dec. 4, 2013), 102 pages.
Plaintiffs' Proposed Findings of Fact and Conclusions of Law filed by Emory University, Gilead Sciences, Inc. Case No. 1:08-cv-10838-RJS (Dec. 5, 2013), 111 Pages.
Plaintiffs' Notice of PTX, A, B, and C (exhibits) in Support of Post-trial Memorandum regarding Post Trial Memorandum filed by Emory University, Gilead Sciences, Inc. Case No. 1:08-cv-10838-RJS, (Filed Dec. 5, 2013), 81 pages.
Plaintiffs' Opposition to Defendants' Post-Trial Memorandum filed by Emory University, Gilead Sciences, Inc. Case No. 1:08-cv-10838-RJS (Filed Dec. 18, 2013), 22 pages.
Defendants' Post-Trial Reply Memorandum filed by Teva Pharmaceutical Industries Limited, Teva Pharmaceuticals USA, Inc., Case No. 1:08-cv-10838-RJS (Filed Dec. 18, 2013), 20 pages.
Stipulation of Dismissal, Case No. 1:08-cv-10838-RJS (Dated Jan. 29, 2014), 3 pages.
Order, Case No. 1:08-cv-10838-RJS (Dated Feb. 13, 2014), 1 page.
Order on Stipulation for Dismissal, Case No. 1:08-cv-10838_RJS (Dated Apr. 30, 2014), 2 pages.
Staszewski, S., J. Gallant, A. Pozniak, J. M. A. H. Suleiman, E. DeJesus, E. Koenig, S. Coleman et al. "Efficacy and safety of tenofovir disoproxil fumarate (TDF) versus stavudine (d4T) when used in combination with lamivudine (3TC) and efavirenz (EFV) in HIV-1 infected patients naive to antiretroviral therapy (ART): 48-week interim results." Oral 17, 14th International AIDS Conference, Jul. 7-12, 2002 (poster).
Staszewski, S., J. Gallant, A. Pozniak, J. M. A. H. Suleiman, E. DeJesus, E. Koenig, S. Coleman et al. "Efficacy and safety of tenofovir disoproxil fumarate (TDF) versus stavudine (d4T) when used in combination with lamivudine (3TC) and efavirenz (EFV) in HIV-1 infected patients naive to antiretroviral therapy (ART): 48-week interim results of Study GS-99-903" Oral 17, 14th International AIDS Conference, Jul. 7-12, 2002 (presentation), 23 pages.
Declaration of Dr. Jonathan A V Coates in the matter Australian patent application 2011253996 in the name of Gilead Sciences, Inc. and in the matter of Opposition by Alphapharm, Jun. 2, 2015.
Declaration of Andrew David Carr in the matter Australian patent application 2011253996 in the name of Gilead Sciences, Inc. and in the matter of Opposition by Alphapharm, Jun. 2, 2015.
Declaration of Helen Grimes in the matter Australian patent application 2011253996 in the name of Gilead Sciences, Inc. and in the matter of Opposition by Alphapharm, Jun. 2, 2015.
Statement of Grounds and Particulars filed by Alphapharm Pty Ltd in the Australian Patent Office for Application No. 2011253996, dated Mar. 17, 2015, 12 pages.
Australian Product Information for EMTRIVA (emtricitabine) Capsules, Apr. 2014, 22 pages.
Australian Product Information for Viread® (tenofovir disoproxil fumarate) 300 mg Tablets, Oct. 2013, 44 pages.
Australian Product Information for 3TC® Tablets and Oral Solution , Feb. 2015, 26 pages.
Australian Product Information for REYATAZ® (atazanavir sulfate), Dec. 2014, 52 pages.
Australian Product Information for STOCRIN® (efavirenz), Mar. 2015, 29 pages.
Australian Product Information for KALETRA, Jan. 30, 2015, 39 pages.
Abstracts of the 10th Conference on Retroviruses and Opportunistic Infections Feb. 10-14, 2003, p. 10, Abstract 564b (A-564b), 5 pages.
Braunwald et al, Harrison's Principles of Internal Medicine (McGraw-Hill, 15th ed, 2001),pp. 1852-1913 (Harrison's).

(56) References Cited

OTHER PUBLICATIONS

Cadman et al GMHC Treat Issues vol. 12 No. 3, 1998, pp. 5-9 (1998).
Rudnic, E., Remington 20th Edition, Chapter 45, pp. 996-1035, (2000).
"AIDS," Monthly Index of Medical Specialties, pp. 194-198 (2002).
"Anti-HIV Drug Updates—Three Drugs on the Near Horizon," Project Inform Perspective 35:4-7 (2003).
"Atripla Fact Sheet", www.fda.gov, [Online], Jul. 12, 2006, pp. 1-2 retrieved from the internet www.fda.gov/cder/drug/inforpage/atripla/factsheet.htm [retrieved on Jan. 31, 2007.
"Gilead Buys Triangle in $464M Deal" Pharma Marketletter, 1 page (Dec. 9, 2002).
"Gilead Captures Triangle for $464 Million," Chemical Market Reporter 262(21):1 page (Dec. 9, 2002).
"Gilead set to acquire Triangle for $464m," BT Catalyst 17(1):1 page (Jan. 1, 2003).
"HIV Treatment Information," Project Inform, (on line), Jan. 2006, pp. 1-3, retrieved from http://www.projinf.org/bn/news_013006.html [retrieved on Jan. 31, 2007].
"Rescriptor," Patient Prescribing Information Leaflet, 7 pages (2001).
"Scientific Discussion," EMEA, pp. 1/28-3/28, European Medicines Agency: (Feb. 2005).
Adis Data Information, "Emtricitabine/Tenofovir Disoproxil Fumarate," Drugs in R & D 5(3):160-161 (2004).
Alexander et al., "Investigation of (Oxodioxolenyl)methyl carbamates as nonchiral bioreversible prodrug moieties for chiral amines," J. Med. Chem. 39:480-486, 1996.
Amended Answer and Counterclaim against Gilead Sciences, Inc. filed by Teva Pharmaceuticals USA, Inc and Teva Pharmaceuticals Industries, Ltd. Case No. 08-CV-10838 (Jul. 20, 2009).
Anderson, "Antiviral dynamics and sex differences of zidovudine and lamivudine triphosphate concentrations in HIV-infected individuals," AIDS 17:2159-2168 (2003).
Ansel et al., "Pharmaceutical Dosage Forms and Rug Delivery Systems," 7th Edition, Lippincott Williams & Wilkins, pp. 209-213 (1999).
Answer and Counterclaim against Gilead Sciences, Inc. filed by Teva Pharmaceuticals USA, Inc and Teva Pharmaceuticals Industries, Ltd. Case No. 08-CV-10838 (Feb. 5, 2009).
Answer filed by Teva Pharmaceuticals USA, Inc and Teva Pharmaceuticals Industries, Ltd. Case No. 10-CV-01796 (May 10, 2010).
Answer filed by Teva Pharmaceuticals USA, Inc and Teva Pharmaceuticals Industries, Ltd. Case No. 10-CV-01851 (May 17, 2010).
Arimilli et al., "Orally bioavailable acylic nucleoside phosphonate prodrugs: Adefovir, Dipivoxil and Bis(POC)PMPA," vol. 3 (accepted for publication), Adv. Antiviral Drug Design, 1998.
Arimilli et al., "Synthesis, in vitro biological evaluation and oral bioavailability of 9-[2-(phosphonomethoxy)propyl]adenine (PMPA) prodrugs," Antiviral Chem. & Chemo. 8(6):557-567, 1997.
Arribas et al., "Tenofovir Disoproxil Fumarate, Entricitabine and Efavirenz Compared with Zidovudine/Lamivudine and Efavirenz in Treatment-Naive Patients 144-Week Analysis," JAIDS 47(1):74-78 (2008).
Balzarini et al, "Differential antiherpesvirus and antiretrovirus effects of the (S) and (R) enantiomers of acyclic nucleoside phosphonates: potent and selective in vitro and in vivo antiretrovirus activities of (R)-9-(2-phosphonomethoxypropyl)-2,6-diaminopurine." Antimicrob Agents Chemother. Feb. 1993; 37(2): 332-338.
Banker, Modem Pharmaceutics, Drugs and the Pharmaceutical Sciences, p. 340, Mercel Dekker, Inc. 1996.
Bartlett et al., "Overview of the effectiveness of triple combination therapy in antiretroviral-naive HIV-1 infected adults," AIDS 15:1369-1377 (2001).
Beauchamp et al., "Amino acid ester prodrugs of acyclovir," Antivir. Chem. and Chemoth. 3(3):157-64, 1992.

Benzaria et al., "New prodrugs of 9-(2-phosphonomethoxyethyl)adenine (PMEA): Synthesis and stability studies," Nucls. & Nuclt. 14(3-5):563-565, 1995.
Benzaria et al., "Synthesis, in Vitro Antiviral Evaluation, and Stability Studies of Bis(S-acyl-2-thioethyl) Ester Derivatives of 9[2-(Phosphonometyoxy)ethyl]adenine (PMEA) as Potential PMEA Prodrugs with Improved Oral Bioavailability," J. Med. Chem. 39:4958-4965 (1996).
Berge et al., "Pharmaceutical salts," J. Pharm. Sci. 66(1):1-19, 1977.
Blackburn et al., "DNA and RNA structure," pp. 15-81, Nucleic Acids in Chemistry and Biology, 1996.
Bristol Myers Squibb "Sustiva®," http://www.fda.gov/medwaTCH/SAFETY/2005/Sustiva_PI61005.pdf, pp. 3-40 (retrieved Jan. 31, 2007).
Bundgaard et al., "Design and Application of Prodrugs," pp. 113-191, Textbook of Drug Design and Development, 1991, 1 page.
Byrn (editor), Solid State Chemistry of Drugs, 2cd Edition, p. 22, 1999.
Colla et al., "Synthesis and antiviral activity of water-soluble esters of acyclovir [9-[(2-Hydroxyethoxy)methyl]guanine]," J. Med. Chem. 26:602-04, 1983.
Communication about intention to grant a European patent for Patent Publication EP 1583542 (Application No. 04701819.7) issued by the European Patent Office (Nov. 5, 2007).
Communication and Annex for Patent Publication EP 1583542 (Application No. 04701819.7) issued by the European Patent Office (Jul. 17, 2007).
Communication and Annex for Patent Publication EP 1583542 (Application No. 04701819.7) issued by the European Patent Office (Jul. 26, 2006).
Communication and Annex for Patent Publication EP 1583542 (Application No. 04701819.7) issued by the European Patent Office (Oct. 24, 2005).
Communication from the Examining Division of the EPO for EP 1890681 B1 (Application No. 06773194.3) (May 13, 2009).
Communication of further notices of opposition pursuant to Rule 79(2) EPC for EP 1583542 B1 (Application No. 04701819.7) and Request to File Observations (Apr. 23, 2009).
Communication of Intent to Grant EP 1890681 B1 (Application No. 06773194.3) and Druckexemplar issued by the European Patent Office (Jul. 15, 2008).
Communication of notices of opposition pursuant to Rule 79(2) EPC for EP 1890681 B1 (Application No. 06773194.3) and Request to File Observations (Nov. 12, 2009).
Communication pursuant to Article 94(3) EPC for Patent Publication EP 1923063 (Application No. 08152527.1) issued by the European Patent Office (Sep. 4, 2009).
Complaint for Patent Infringement against Teva Pharmaceuticals USA, Inc and Teva Pharmaceuticals Industries, Ltd. filed by Gilead Sciences, Inc. and Emory University Case No. 10-CV-01798 (Mar. 5, 2010).
Complaint for Patent Infringement against Teva Pharmaceuticals USA, Inc and Teva Pharmaceuticals Industries, Ltd. filed by Gilead Sciences, Inc. Case No. 08-CV-10838 (Dec. 12, 2008).
Complaint for Patent Infringement against Teva Pharmaceuticals USA, Inc and Teva Pharmaceuticals Industries, Ltd. filed by Gilead Sciences, Inc. Case No. 10-CV-01796 (Mar. 5, 2010).
Complaint for Patent Infringement against Teva Pharmaceuticals USA, Inc and Teva Pharmaceuticals Industries, Ltd. filed by Merck, Sharp & Dohme Corp and Bristol-Myers Squib Company. Case No. 10-CV-01851 (Mar. 9, 2010).
Conference Call Transcript—Gilead Sciences Conference call to Discuss Triangle Pharmaceuticals Acquisition. Event Date/Time Dec. 4, 2002/ 9:00 AM ET (11 pages).
Correction of an Error in the Decision According to Rule 140 EPC for EP 1890681 B1 (Application No. 06773194.3) (Jul. 5, 2011).
Dando et al., "Emtricitabine/Tenofovir Disoproxil Fumarite," Drugs 64(18):2075-2082 (2004).
Davidsen et al., "N-(Acyloxyalkyl)pyridinium salts as soluble prodrugs of a potent platelet activating factor antagonist," J. Med. Chem. 37(26):4423-4429, 1994.

(56) References Cited

OTHER PUBLICATIONS

De Clercq et al., "(S)-9-(2,3-dihydroxypropyl)adenine: An aliphatic nucleoside analog with broad spectrum antiviral activity," Science 200:563-565, 1978.
De Clercq, "Antiviral drugs: current state of the art," J. Clin. Virol. 22:73-89 (2001).
De Clercq et al., "New Developments in Anti-HIV Chemotherapy," Curr. Med. Chem. 8(13):1543-1572 (2001).
De Clercq et al., "New developments in anti-HIV chemotherapy," Farmaco 56(1-2):3-12 (2001).
De Clercq, "Highlights in the Development of New Antiviral Agents," Mini-Rev. Med. Chem. 2(2):163-175 (2002).
De Clercq, "New developments in anti-HIV chemotherapy," Biochem Biophys Acta 1587(2-3):258-275 (2002).
De Lombaert et al., "N-Phosphonomethyl Dipeptides and their Phosphonate Prodrugs, a New Generation of Neutral Endopeptidase (NEP, EC 3.4.24.11) Inhibitor," J. Med. Chem. 37:498-511 (1994).
Decision of Hearing of the Indian Patent Office for Patent Application No. 3383/DELNP/2005 (Mar. 25, 2009).
Decision of Rejection for Application No. 7000806/1999 issued by the Korean Intellectual Property Office (Jan. 20, 2006) (translation).
Decision of Rejection for Patent Application No. 7000636/2000 issued by the Korean Intellectual Property Office (May 10, 2006) (translation).
Decision of Rejection for Patent Application No. 7007002/2008 issued by the Korean Intellectual Property Office (Jan. 7, 2009) (translation).
Decision of Rejection for Patent Application No. 86110757 issued by the Intellectual Property Office of Taiwan (Nov. 11, 1999) (translation).
Decision of Rejection for Patent Application No. 87112168 issued by the Taiwanese Intellectual Property Office (Apr. 6, 2001) (translation).
Decision of the Opposition Division for EP Patent EP 1583542 B1 (Application No. 04701819.7), Claims, Grounds for the Decision and Provision of the minutes (Jan. 31 and Feb. 14, 2011).
Decision to Grant Patent Application No. 06773194.3 (EP 1890681B1) issued by the European Patent Office (Dec. 11, 2008).
Declaration of Colleen Tracy in Support of a Motion for Leave to File Amended Complaint Case No. 10-CV-01796 (Apr. 11, 2011).
Declaration of James Galbraith in Opposition of a Motion for Leave to File Amended Complaint Case No. 10-CV-01796 (Apr. 25, 2011).
Delehanty et al. Slides from the oral presentation for "A Randomized Study of Three Doses of FTC Versus 3TC in HIV-Infected Patients," 6th CROI (Jan. 31-Feb. 4, 1999) Chicago.
Delehanty et al., "A Phase I/II Randomized, Controlled Study of FTC Versus 3TC in HIV-Infected Patients," 6th CROI (Jan. 31-Feb. 4, 1999) Chicago, Session 5, Abstract 16.
Drugs and the Pharmaceutical Sciences, vol. 1999, p. 60 (Mark Gibson, ed), 2009.
Engel, R., "Phosphonates as analogues of natural phosphates," Chem. Rev. 77(3):349-367, 1977.
Examination Report for Patent Application No. 540728 issued by the Intellectual Property Office of New Zealand (Apr. 24, 2007).
Examination Report Patent Application No. 564045 issued by the Intellectual Property Office of New Zealand (Oct. 6, 2009).
Examiner's First Report on Patent Application No. 2009200414 issued by the Australian Patent Office (Feb. 24, 2010).
Examiner's First Report on Patent Application No. 85827/98 issued by the Australian Patent Office (Feb. 28, 2001).
Examiner's First Report Patent Application No. 20026257795 issued by the Australian Patent Office (Sep. 29, 2009).
Examiner's Remarks for Patent Application No. a 2008 00493 issued by the Ukrainian Patent Office (2010).
Examiner's Second Report on Patent Application No. 85827/98 issued by the Australian Patent Office (Mar. 27, 2002).
Examiner's First Report on Patent Application No. 2004206821 issued by the Australian Patent office (Aug. 28, 2007).
Examiner's Remarks for Patent Application No. 200501134/28 issued by the Eurasian Patent Office (received Jul. 30, 2009) (translation).
Examiner's Second Report on Patent Application No. 2004206821 issued by the Australian Patent office (Aug. 20, 2008).
Extended European Search Report for Patent Publication EP 1923063 (Application No. 08152527.1) issued by the European Patent Office (Mar. 10, 2009).
Farquhar et al., "Biologically Reversible Phosphate-Protective Groups," J. Pharm. Sci. 72:324-325 (1983).
Farquhar et al., "Synthesis and antitumor evaluation of Bis[(pivaloxy)methyl] 2'-deoxy-5-fluorouridine 5'-monophosphate (FdUMP): a strategy to introduce nucleotides into cells," J. Med. Chem. 37(23):3902-03, 1994.
Fasman et al., pp. 385-394, Practical Handbook of Biochem. and Molec. Biol., 1989.
FDA: "Guidance for industry fixed dose combination and co-packaged drug products for treatment of HIV," www.fda.org. [on line], May 2004, pp. 1-17, (retrieved from http://www.fda.gov/oc/initiatives/hiv/hivguidance.html>[retrieved on Jan. 31, 2007].
Fell et al., "The tensile strength of lactose tablets" J. Pharm. Pharmacol. 20:657-659 (1968).
Feng et al. 2009 "The triple combination of tenofovir, emtricitabine and efavirenz show synergistic anti-HIV-1 activity in vitro: a mechanism of action study," Retrovirology 6:44, http://www.retrovirology.com/content/6/1/44.
Feng, J. et al, "Mechanistic studies show that 9-)-FTC-TP is a better inhibitor of HIV-1 reverse transcriptase than 3TC-TP," FASEB 13:1511-1517 (1999).
Final Office Action for Patent Application No. 86110757 issued by the Intellectual Property Office of Taiwan (Sep. 5, 2000) (translation).
Final Office Action for Patent Application. No. 89123708 issued by the Intellectual Property Office of Taiwan (Apr. 12, 2001) (translation).
First Amended Complaint for Patent Infringement against Teva Pharmaceuticals USA, Inc and Teva Pharmaceuticals Industries, Ltd. filed by Gilead Sciences, Inc., Emory University Case No. 08-CV-10838 (Jul. 1, 2009).
First Examination Report for Application No. 564102 Issued by the Intellectual Property Office of New Zealand (Oct. 6, 2009).
First Examination Report for Patent Application No. 3383/DELNP/2005 from the Indian Patent Office (Jul. 31, 2007).
First Examination Report for Patent Application No. 602/DEL/2007 issued by the Indian Patent Office (Nov. 18, 2009).
First Office Action for Patent Application No. 200410046290.X issued by the Chinese Patent Office (Jun. 17, 2005) (translation).
First Office Action for Patent Application No. 200480002190.5 issued by the Patent Office of the People's Republic of China (Aug. 4, 2006).
First Office Action for Patent Application No. 200510099916.8 issued by the Chinese Patent Office (Jun. 15, 2007) (translation).
First Office Action for Patent Application No. 97197460.8 issued by the Chinese Patent Office (Jan. 16, 2004) (translation).
First Official Action for Patent Application No. a 2008 00555 issued by the Ukrainian Patent Office (2011) (translation).
Fiske et al., "Pharmacokinetics, safety and tolerability of single escalating doses of DMP 266, an HIV non-nucleoside reverse transcriptase inhibitor, in healthy volunteers," Pharm. Res. 14(11 Suppl.):S609 (1997).
Flaherty et al., "Synthesis and selective monoamine oxidase B-inhibiting properties of 1-Methyl-1,2,3,6-tetrahydropyrid-4-yl carbamate derivatives: potential prodrugs of (R)-and (S)-Nordeprenyl," J. Med. Chem. 39:4759-4761, 1996.
Folkmann et al., "Acyloxymethyl carbonochloridates. New intermediates in prodrug synthesis," Synthesis, pp. 1159-1166, 1990.
Frampton et al., "Emtricitabine: A Review of Its Use in the Management of HIV Inspection," Drugs 65(10):1427-1448 (2005).
Freeman et al.., "3 Prodrug Design for Phosphate and Phosphonates," Progress in Medicinal Chemistry 34:112-147 (1997).
Fridland, "Tenofovir," Curr. Opin. Anti-Infect. Invest. Drugs 2(3):295-301 (2000).

(56) References Cited

OTHER PUBLICATIONS

Fung et al., "Tenofovir Disoproxil Fumarate: A Nucleotide Reverse Transcriptase Inhibitor for the Treatment of HIV Infection," Clin. Therapeutics 24(10):1515-1548 (2002).
Further Examination Report for Patent Application No. 540728 issued by the Intellectual Property Office of New Zealand (Feb. 11, 2008).
Further Examination Report for Patent Application No. 540728 issued by the Intellectual Property Office of New Zealand (Jun. 18, 2008).
Generics [UK] Limited, Notice of Opposition of EP Patent EP 1583542B1 (Application No. 04701819.7) (Mar. 18, 2009).
Generics [UK] Limited, Written Submission in preparation for Oral Proceedings for EP Patent EP 1583542 B1 (Application No. 04701819.7) (Sep. 17, 2010).
Gerhartz (editor) Ullmann's Encyclopedia of Industrial Chemistry vol. B2, Unit Operations I, 5th Edition, p. 3-7.
Gilead "Truvada®," http://www.fda.gov/medwatch/SAFETY/ 2005/Oct_PI/Truvada_PI.pdf, pp. 1-29 (retrieved Jan. 31, 2007).
Gilead Sciences Inc., Appeal Grounds against the Decision of the Opposition Division for EP 1890681 B1 (Application No. 06773194.3) (Oct. 17, 2011).
Gilead Sciences Inc., Notice of Appeal against the Decision of the Opposition Division for EP 1890681 B1 (Application No. 06773194.3) (Aug. 16, 2011).
Gilead Sciences Inc., Written Submission in preparation for Oral Proceedings for the Opposition of EP 1890681 B1 (Application No. 06773194.3) (Feb. 4, 2011).
Gilead Sciences Inc., Written Submission in preparation for Oral Proceedings for the Opposition of EP 1890681 B1 (Application No. 06773194.3) (Mar. 2 & 4, 2011).
Gilead Sciences Inc., Written Submission in preparation to/during Oral Proceedings for EP Patent EP 1583542 B1 (Application No. 04701819.7) (Sep. 17, 2010).
Gilead Sciences, Inc., "Data Comparing Viread (R) and Emtriva (R) to Combivir (R) as Part of Combination HIV Therapy Published in New England Journal of Medicine," p. 1-5, Press Release, 2006.
Gilead Sciences, Inc., "Gilead Sciences to Acquire Triangle Pharmaceuticals for $464 Million; Gilead to Launch Coviracil in 2003; Will Develop Co-Formulation of Viread and Coviracil," 2 pages, Press Release (2002).
Gilead Sciences, Inc., "U.S. FDA Approves Gilead Sciences' Emtriva A one-capsule, Once-Daily Medication for the Treatment of HIV," pp. 3-7, Press Release, 2003.
Gilead Sciences, Inc., Physician Insert for Truvada, pp. 1-30 (2007).
Gilead, Bristol-Myers Squibb "Atripla™," http://www.fda.gov/ cder/foi/;abe;/2006/0219371b1.pdf, pp. 4-53 (retrieved Jan. 31, 2007).
Gilead: "Bristol-Myers Squibb and Gilead announce data supporting bioequivalence for single PIII fixed dose regimen of Sustiva®(efavirenz) and Truvada® (emtricitabine and tenofovir fumarate)" Gilead Press Release (online Jan. 9, 2006), pp. 1-5, retrieved from http://www.gilead.com/press.
Gilead: "Gilead provides update on development of fixed-dose regimen of Truvada (emtricitabine and tenofovir disoproxil fumarate) and Sustiva (efavirenz)," Gilead Press Release, [on line], Apr. 26, 2005, pp. 1-3, retrieved from http://www.gilead.com/press.
Hammer et al., "Ether, carbonate and urethane deoxynucleoside derivatives as prodrugs," Acta Chemica Scandinavia 50:609-622, 1996.
Harris et al., "Genotypic Analysis of HIV-1 Infected ART Naive Patients Receiving Emtricitabine (FTC) or Lamivudine (3TC) in a Double Blind Equivalence Trial," 5th International Workshop on Drug Resistance and Treatment Strategies, Jun. 4-8, No. 104 (2001).
Havlir et al., "In Vivo Antagonism with Zidovudine plus Stavudine Combination Therapy," J. Infect. Disease 182:321-325 (2000).
Hazen et al., "Relative Anti-HIV-1 Efficacy of Lamivudine and Emtricitabine in Vitro Is Dependent on Cell Type," J. AIDS 32:255-258 (2003).

Hostetler et al., "Greatly Enhanced Inhibition of Human Immunodeficiency Virus Type 1 Replication in CEM and HT 4-6C Cells by 3'-Deoxythymidine Diphosphate Dimyristoylglycerol, a Lipid Prodrug of 3'-Deoxythymidine," Antimicro. Agent Chemo. 36(9):2025-2029 (1992).
Hostetler et al., "Synthesis and Antiretroviral Activity of Phospholipid Analogs of Azidothymidine and Other Antiviral Nucleosides," J. Biol. Chem. 265(11):6112-6117 (1990).
Ibbotson et al., Drugs 2003, 63(11), 1089-1096.
Ikeda et al., "Studies of prodrugs III. A convenient and practical preparation of Amphicillin prodrugs," Chem. Pharm. Bull. 32:4316-4322, 1984.
Information about the Results of Oral Proceedings for EP Patent EP 1583542 B1 (Application No. 04701819.7), Claims, Amended Claims and Minutes of the Oral Proceeding (Nov. 19, 2010).
International Preliminary Report on Patentability for PCT/US2004/ 000832 (Dec. 29, 2004).
International Preliminary Report on Patentability for PCT/US2006/ 023222 (Oct. 8, 2007).
International Preliminary Report on Patentability for PCT/US2006/ 023223 (Oct. 8, 2007).
International Search Report and Written Opinion mailed Jul. 12, 2004 for PCT/US2004/000832, Int'l. Filing Date Jan. 13, 2004.
International Search Report for PCT/US1997/013244 (Oct. 20, 1997).
International Search Report for PCT/US1998/015254 (Nov. 25, 1998).
International Search Report for PCT/US2006/023222 (Feb. 23, 2007).
International Search Report for PCT/US2006/023223 (Feb. 23, 2007).
Ishida and Asao, "Self-association and unique DNA binding properties of the anti-cancer agent TAS-103, a dual inhibitor of topoisomerases I and II," Biochem. Biophys. Acta 1587(2-3):155-163 (2002).
Iyer et al., "Synthesis of acyloxyalkyl acylphosphonates as potential prodrugs of the antiviral Trisodium phosphonoformate (Foscarnet sodium)," Tet. Lett. 30(51): 7141-7144, 1989.
Jones et al., "Minireview: nucleotide prodrugs," Antiviral Res. 27:1-17 (1995).
Kearney et al., "Effect of Demographic Variables on the Pharmacokinetics of Tenofovir DF in HIV-Infected Patients and Healthy Subjects," 41st ICAAC Abstracts, Chicago, IL, Sep. 22-25, 2001, Abstract A-504.
Khamnei et al., "Neighboring Group Catalysis in the Design of Nucleotide Prodrugs," J. Med. Chem. 39:4109-4115 (1996).
King et al. "Potency of Nonnucleoside Reverse Transcriptase Inhibitors (NNRTIs) Used in Combination with Other Human Immunodeficiency Virus NNRTIs, NRTIs, or Protease Inhibitors," Antimicrobial Agents and Chemotherapy 46(6):1640-1646 (2002).
Kleinebudde et al. European journal of Pharmaceutics and Biopharmaceutics, 2004, 58, 317-326.
Krise et al., "Prodrugs of phosphates, phosphonates, and phosphinates," Advanced Drug Delivery Reviews 19:287-310, 1996.
Kucera et al., "Novel Membrane-Interactive Ether Lipid Analogs That Inhibit Infectious HIV-1 Production and Induce Defective Virus Formation," AIDS Res. & Hum. Retro. 6:491-501 (1990).
Lachman, et al. (1987) "The Theory and Practice of Industrial Pharmacy", Varghese Publishing House, Dadar Bombay, pp. 330-331.
Landgrebe, J. A., "Crystallization and filtration," Theory and Practice in the Organic Laboratory, 3rd Edition, pp. 65-77, 1982.
Letter Regarding the Opposition Procedure for EP Patent EP 1583542 B1 (Application No. 04701819.7) (Mar. 11, 2010).
Lieberman et al., "," Pharmaceutical Dosage Forms 1:177-178 (1989).
Lindahl et al., "Synthesis of an acyloxymethyl prodrug of the Inositol phosphate alpha-Trinositol," J. Carbohydrate Chemistry 15(5):549-554, 1996.
Liu et al., "Thymidylate synthase as a translational regulator of cellular gene expression," Biochem. Biophys. Acta 1587(2-3):174-182 (2002).

(56) References Cited

OTHER PUBLICATIONS

Loveday, "Nucleoside reverse transcriptase inhibitor resistance," JAIDS 26:S10-S24 (2001).

Maillard et al., "Adenosine receptor prodrugs: Synthesis and biological activity of derivatives of potent A1-selective agonists," J. Pharm. Sci. 83(1):46-53, 1994.

Margot et al., "Development of HIV-1 Drug Resistance Through 144 Weeks in Antiretroviral-Naive Subjects on Emtricitabine, Tenofovir Disoproxil Fumarate, and Efavirenz Compared with Lamivudine/Zidovudine and Efavirenz in Study GS-01-934," JAIDS 52(2):209-221 (2009).

Margot et al., "Genotypic and phenotypic analyses of HIV-1 in antiretroviral-experienced patients treated with tenofovir DF," AIDS 16:1227-1235 (2002).

Margot et al., "Resistance development over 144 weeks in treatment-naive patients receiving tenofovir disoproxil fumarate or stavudine with lamivudine and efavirenz in Study 903," HIV Medicine 7:442-450 (2006).

Masho et al., "Review of Tenofovir-Emtricitabine," Ther. Clin. Risk Manag. 3(6):1097-1104 (2007).

McColl et al., "Pooled Analysis of Recent Emtricitabine and Lamivudine Clinical Trials Reveals Differences in Rates of Development of the M184V/I Mutation," Poster Number: PE7.3/17, 10th European AIDS Conference (EACS) Nov. 17-20, 2005, Dublin Ireland.

McIntee et al., "Probing the mechanism of action and decomposition of amino acid phosphomonoester amidates of antiviral nucleoside prodrugs," J. Med. Chem. 40(2):3323-31, 1997.

Memorandum of Law in Opposition of a Motion for Leave to File Amended Complaint Case No. 10-CV-01796 (Apr. 25, 2011).

Miller et al., Sixth International Congress on Drug Therapy in HIV Infection, Nov. 17- 21, 2002 (1 page).

Mills et al., "Artemis: Efficacy and Safety of Darunavir/ritonavir (DRV/r) 800/100mg Once-daily vs Lopinavfr/ritonavir (LPV/r) in Treatment-naive, HIV-1-infected Patients at 96 wks," 48th Annual ICAAC/IDSA, 46th Annual Meeting, Washington, D.C. Oct. 25-28, 2008, Presentation Number: H-1250c.

Minutes of the Oral Proceedings before the Opposition Division for EP 1890681 B1 (Application No. 06773194.3) and Appendices (Apr. 5, 2011).

Molina et al., "A Lopinavir/Ritonavir-Based Once-Daily Regimen Results in Better Compliance and Is Non-inferior to a Twice-Daily Regimen Through 96 Weeks," AIDS Research and Human Retroviruses 23(12):1505-1514 (2007).

Molina et al., "Once-Daily Combination Therapy with Emtricitabine, Didanosine, and Efavirenz in Human Immunodeficiency Virus-Infected Patients," J. Infect. Dis. 182:599-602 (2000).

Mulato et al., "Anti-HIV activity of adefovir (PMEA) and PMPA in combination with antiretroviral compounds: in vitro analyses," Antiviral Res. 36(2):91-97 (1997).

Murry et al., "Reversion of the M184V Mutation in Simian Immunodeficiency Virus Reverse Transcriptase is Selected by Tenofovir, Even in the Presence of Lamivudine," J. Virol. 77(2):1120-1130 (2003).

Naesens et al., "Antiretroviral activity and pharmacokinetics in mice of oral Bis(Pivaloyloxymethyl)-9-(2-phosphonylmethoxyethyl)adenine, the Bis(Pivaloyloxymethyl)ester prodrug of 9-(2-Phosphonylmethoxyethyl)adenine," Antimicro AG & Chemo. 40(1)22-28, 1996.

Newman and Byrn, "Solid-state analysis of the active pharmaceutical ingredient in drug products" Drug Discovery Today, 8(19) 898-905 (2003).

Notari, "Prodrug Design," Pharmaceutical Therapy, 14:25-53, 1981.

Notice of Appeal of the Decision of the Opposition Division for EP Patent EP 1583542 B1 (Application No. 04701819.7) (Mar. 29, 2011).

Office Action for Korean Patent Application No. 7013069/2005 issued by the Korean Intellectual Property Office (May 22, 2007).

Office Action for Patent Application No. 10-2000-7000636 issued by the Korean Intellectual Property Office (Aug. 19, 2005) (translation).

Office Action for U.S. Appl. No. 08/900,752 issued by the United States Patent and Trademark Office (Apr. 16, 1998).

Office Action for Patent Application No. 11-510067 issued by the Japanese Patent Office (Dec. 11, 2007) (translation).

Office Action for Patent Application No. 2,261,619 issued by the Canadian Patent Office (Dec. 22, 2004).

Office Action for Patent Application No. 2,298,059 issued by the Canadian Intellectual Property Office (Apr. 25, 2007).

Office Action for Patent Application No. 2,512,475 issued by the Canadian Patent Office (Jan. 10, 2008).

Office Action for Patent Application No. 2,611,520 issued by the Canadian Patent Office (Jun. 7, 2010).

Office Action for Patent Application No. 2006-500939 issued by the Japanese Patent Office (Mar. 25, 2010).

Office Action for Patent Application No. 2006-500939 issued by the Japanese Patent Office (Nov. 9, 2009).

Office Action for Patent Application No. 7007002/2008 issued by the Korean Intellectual Property Office (Jun. 11, 2008) (translation).

Office Action for Patent Application No. 7009376/2009 issued by the Korean Intellectual Property Office (Oct. 9, 2009) (translation).

Office Action for Patent Application No. 87112168 issued by the Taiwanese Intellectual Property Office (Mar. 1, 2004) (translation).

Office Action for Patent Application No. 87112168 issued by the Taiwanese Intellectual Property Office (May 6, 2002) (translation).

Office Action for Patent Application No. 87112168 issued by the Taiwanese Intellectual Property Office (Oct. 20, 2000) (translation).

Office Action for Patent Application No. 93112403 issued by the Taiwanese Intellectual Property Office (Apr. 27, 2005) (translation).

Official Action for Application No. 095120445 issued by the Taiwanese Intellectual Property Office (Nov. 29, 2011) (translation).

Official Action for Application No. 2008-517083 issued by the Japanese Patent Office (Aug. 2, 2011) (translation).

Official Action for Ex Parte Reexamination of U.S. Pat. No. 5,922,695 (Dec. 11, 2007).

Official Action for Ex Parte Reexamination of U.S. Pat. No. 5,935,946 (Jan. 16, 2008).

Official Action for Ex Parte Reexamination of U.S. Pat. No. 5,977,089 (Jan. 16, 2008).

Official Action for Ex Parte Reexamination of U.S. Pat. No. 6,043,230 (Dec. 11, 2007).

Official Action for Patent Application No. 10-1999-7000806 issued by the Korean Intellectual Property Office (Apr. 28, 2005) (translation).

Official Action for Patent Application No. 10-508318 issued by the Japanese Patent Office (Apr. 10, 2007) (translation).

Official Action for Patent Application No. 200501134/28 issued by the Eurasian Patent Office (Dec. 25, 2008).

Official Action for Patent Application No. 200501134/28 issued by the Eurasian Patent Office (Oct. 15, 2006).

Official Action for Patent Application No. 333687 issued by the Intellectual Property Office of New Zealand (Mar. 2, 1999).

Official Action for Patent Application No. 7001077/2008 issued by the Korean Intellectual Property Office (Sep. 13, 2010).

Official Action for Patent Application No. 93100813 issued by the Taiwanese Intellectual Property Office (Jun. 22, 2005) (translation).

Official Action for Patent Application. No. 200800033/27 issued by the Eurasian Patent Office (2010) (translation).

Opinion on Patent Application No. 1-2005-00812 issued by the Vietnamese Patent Office (Jul. 27, 2008).

Opponents Comments to the Reply Statement by the Applicant relating to Patent Application No. 3383/DELNP/2005 (Aug. 14, 2008).

Order Granting Request for Ex Parte Reexamination of U.S. Pat. No. 5,922,695 (Jul. 13, 2007).

Order Granting Request for Ex Parte Reexamination of U.S. Pat. No. 5,935,946 (Jul. 13, 2007).

Order Granting Request for Ex Parte Reexamination of U.S. Pat. No. 5,977,089 (Jul. 13, 2007).

Order Granting Request for Ex Parte Reexamination of U.S. Pat. No. 6,043,230 (Jul. 13, 2007).

(56) References Cited

OTHER PUBLICATIONS

Osol et al., Editor, Remington's Pharmaceutical Sciences, Sixteenth Edition, pp. 1554-1557, 1980.
Pallella et al., J. Med. Chem. 338:853-860 (1998).
Parikh, Handbook of Pharmaceutical Granulation Tech., NY, Marcel Dekker Inc., 1996.
Pharmaceutical Dosage Forms and Drug Delivery Systems, 6th Ed. pp. 171-174 (1995).
Pharmaceutical Technology (2005), Big Pharma Companies Team Up to Develop Once-Daily Triple-Combination HIV Drug,vol. 29, No. 4.
Piantadosi et al., "Synthesis and Evaluation of Novel Ether Lipd Nucleoside Conjugates for Anti-HIV-I Activity," J. Med. Chem. 34:1408-1414 (1991).
Plaintiff's Reply to Teva USA's Amended Counterclaim, filed by Gilead Sciences, Emory University, Case No. 08-CV-10838 (Aug. 10, 2009).
Plaintiff's Reply to Teva USA's Second Amended Counterclaim, filed by Gilead Sciences, Emory University,Case No. 08-CV-10838 (Oct. 15, 2009).
Plaintiff's Reply to Teva's Counterclaim, filed by Gilead Sciences, Inc., Emory University Case No. 08-CV-10838 (Feb. 25, 2009).
Pozniak et al., "Tenofovir Disoproxil Fumarate, Emtricitabine, and Efavirenz Versus Fixed-Dose Zidovudine/Lamivudine and Efavirenz in Antiretroviral-Naive Patients," JAIDS 43(5):535-540 (2006).
Pre-Grant Opposition Petition against Brazilian Patent Application PI 0406760-6 (Aug. 20, 2010).
Puech et al., "Intracellular delivery of nucleoside monophosphates through a reductase-mediated activation process," Antiviral Res. 22:155-174 (1993).
Pujari et al., "Safety and long term effectiveness of generic fixed-dose formulations of nevirpine-based HAART amongst antiretroviral-naïve HIV-infected patients in India," World Health Organization, [on line], Dec. 16, 2003, pp. 99-116; (Retrieved from: http://libdoc.who.int/publications/2003/a86263.pdf.
Rejection Decision for Patent Application No. 200480002190.5 issued by the Patent Office of the People's Republic of China (Jan. 15, 2010).
Rejection of Patent Application No. 93100813 issued by the Taiwanese Intellectual Property Office (Feb. 22, 2006) (translation).
Reply of the Patent Proprietor to the Notice of Opposition of EP 1890681 B1 (Application No. 06773194.3) (Jun. 22, 2010).
Reply of the Patent Proprietor to the Notices of Opposition of EP Patent EP 1583542 B1 (Application No. 04701819.7) (Jan. 4, 2010).
Request for Ex Parte Reexamination of U.S. Pat. No. 5,922,695 (submitted Apr. 30, 2007).
Request for Ex Parte Reexamination of U.S. Pat. No. 5,935,946 (submitted Apr. 30, 2007).
Request for Ex Parte Reexamination of U.S. Pat. No. 5,977,089 (submitted Apr. 30, 2007).
Request for Ex Parte Reexamination of U.S. Pat. No. 6,043,230 (submitted Apr. 30, 2007).
Response to the Written Opinion of the ISA for PCT/US2006/023222 (May 10, 2007).
Response to the Written Opinion of the ISA for PCT/US2006/023223 (May 10, 2007).
Revised International Search Report for PCT/US2004/000832 (Aug. 5, 2004).
Revocation of European Patent EP 1890681 B1 (Application No. 06773194.3) (Jun. 8, 2011).
Richman, "Antiretroviral activity of emtricitabine, a potent nucleoside reverse transcriptase inhibitor," Antivir. Ther. 6(2):83-88 (2001).
Richman, "HIV Chemotherapy," Nature 410:995-1001 (2001).
Ristig et al., "Tenofovir Disoproxil Fumarate Therapy for Chronic Hepatitis B in Human Immunodeficiency Virus/Hepatitis B Virus—Coinfected Individuals for Whom Interferon-α and Lamivudine Therapy Have Failed," J. Infect. Dis.186:1844-1847 (2002).
Robinson et al., "Discovery of the Hemifumarate and (alpha-L-Alanyloxy)methylester as prodrugs of an antirheumatic oxindole: Prodrugs for enolic OH group," J. Med. Chem. 39:10-18, 1996.
Rousseau et al., "Prototype trial design for rapid dose selection of antiretroviral drugs: an example using emtricitabine (Coviracil)," Journal of Antimicrobial Chemotherapy 48:507-513 (2001).
Safadi et al., "Phosphoryloxymethyl carbamates and carbonates—Novel water soluble prodrugs for amines and hindered alcohols," Pharm. Res. 10(9):1350-1355, 1993.
Sakamoto et al., "Studies on prodrugs II. Preparation and characterization of (5-substituted 2-oxo-1, 3-dioxolen-4-yl)methyl esters of Ampicillin," Chem. Pharm. Bull. 32(6):2241-2248, 1983.
Samara et al., "Pharmacokinetic analysis of Diethylcarbonate prodrugs of Ibuprofen and Naproxen," Biopharmaceutics & Drug Disposition 16:201-210, 1995.
Sanne et al., "Genotypic Analysis of HIV-1 Infected ART-Naive Patients Receiving Emtricitabine (FTC) or Lamivudine (3TC) in a Double Blind Equivalence Trial," Poster No. 4433, presented at the XIV International AIDS Conference Jul. 7-12, 2002, Barcelona, Spain.
Sanne et al., "Two Randomized, Controlled, Equivalence Trials of Emtricitabine (FTC) to Lamivudine (3TC)," Poster 4432 presented at the XIV International AIDS Conference, Jul. 7-12, 2002, Barcelona, Spain.
Schinazi et al., "Characterization of Human Immunodeficiency Viruses Resistant to OxathiolaneCytosine Nucleosides," Antimicrobial Agents and Chemotherapy 374:875-881 (1993).
Schinazi et al., "Selective Inhibition of Human Immunodeficiency Viruses by Racemates and Enantiomers of cis-5-Fluoro-1-[2-(Hydroxymethyl)-1,3-Oxathiolan-5-yl]Cytosine," Antimricobial Agents and Chemotherapy 36(11):2423-2431(1992).
Schinazi et al., Letter to the Editor "Assessment of the Relative Potency of Emtricitabine and Lamivudine," J. AIDS 34(2)243-245 (2003).
Search and Examination Report for Appln No. AP/P/2005/003348 issued by the African Regional Intellectual Property Organization, 5 pages. (Apr. 10, 2008).
Second Amended Answer and Counterclaim against Gilead Sciences, Inc. filed by Teva Pharmaceuticals USA, Inc and Teva Pharmaceuticals Industries, Ltd. Case No. 08-CV-10838 (Filed Oct. 9, 2009).
Second Amended Complaint for Patent Infringement against Teva Pharmaceuticals USA, Inc and Teva Pharmaceuticals Industries, Ltd. filed by Gilead Sciences, Inc., Emory University Case No. 08-CV-10838 (Sep. 25, 2009).
Second Office Action for Application No. 200680026180.4 issued by the State Intellectual Property Office of the People's Republic of China (Oct. 20, 2011) (translation).
Second Office Action for Patent Application No. 200510099916.8 issued by the Chinese Patent Office (Nov. 16, 2007) (translation).
Second Office Action for Patent Application No. 97197460.8 issued by the Chinese Patent Office (Aug. 5, 2005) (translation).
Second Official Action for Patent Application No. a 2005 07947 issued by the Ukrainian Patent Office (2006) (translation).
Serafinowska et al., "Synthesis and in vivo Evaluation of prodrug of 9-{2-(Phosphonomethoxy) ethoxy} adenine," J. Med. Chem. 38:1372-1379, 1995.
Shaw et al., "Metabolism and pharmacokinetics of novel oral prodrugs of 9-[(R)-2-(phosphonomethoxy)propyl]adenine (PMPA) in dogs," Pharm. Res. 14(12):1824-1829, 1997.
Siddiqui et al., "Design and Synthesis of Lipophilic Phosphoramidate D4T-MP Prodrugs Expressing High Potency Against HIV in Cell Culture: Structural Determinants for in Vitro Activity and QSAR," J. Med. Chem. 42(20):4122-4128 (1999).
Smith et al., "Randomized, double-blind, placebo-matched, multicenter trial of abavacir/lamivudine or tenofovideintricitabine with lopinavir/ritonavir for inital HIV treatment," AIDS 23:1547-1556 (2009).
Srinivas et al., "Metabolism and in vitro antiretroviral activities of Bis(Pivaloyloxymethyl) prodrugs of acyclic nucleoside phosphonates," Antimicro AG & Chemo. 37(10):2247-2250, 1993.

(56) References Cited

OTHER PUBLICATIONS

Srivastva et al., "Bioreversible phosphate protective groups: Synthesis and stability of model acyloxymethyl phosphates," Bioorg. Chem. 12:118-129, 1984.
Starret et al., "Synthesis and in vitro evaluation of a phosphonate prodrug:bis(pivaloyloxymethyl) 9-(2-phophonylmethoxyethyl)adenine," Antiviral Res. 19:267-273, 1992.
Starret et al., "Synthesis, oral bioavailability determination, and in vitro evaluation of prodrugs of the Antiviral agent 9-[2-(phosphonomethoxy)ethyl]adenine (PMEA)," J. Med. Chem. 37:1857-1864, 1994.
Substantive Examination Report for Patent Application No. W00 2005 02145 from the Indonesian Patent Office (2010).
Sueoka et al., "Pharmacokinetics of Alkoxycarbonyloxy ester prodrugs of PMPA in dogs," Abstract, American Association of Pharmaceutical Science, Western Regional Meeting, Apr. 24-25, 1997.
Summons to Attend Oral Proceedings and Annex to the Communication for EP Patent EP1583542B1 (Application No. 04701819.7) (May 21, 2010).
Summons to Attend Oral Proceedings and Annex to the Communication for the Opposition of EP 1890681 B1 (Application No. 06773194.3) (Oct. 14, 2010).
Tamari, "A Decade in HIV Treatment: What Is the State of the Art and How Did We Arrive," Clinical Excellence for Nurse Practitioners 5(1):4-12 (2001).
Teva Pharmaceutical Industries Ltd., Notice of Opposition of EP Patent EP1583542B1 (Application No. 04701819.7) (Mar. 13, 2009).
Teva Pharmaceutical Industries Ltd., Written Submission in preparation for Oral Proceedings for EP Patent EP1583542B1 (Application No. 04701819.7) (Sep. 16, 2010).
Teva Pharmaceuticals Industries Ltd., Notice of Opposition of EP 1890681B1 (Application No. 06773194.3) (Oct. 7, 2009).
Teva Pharmaceuticals Industries Ltd., Written Submission in preparation for Oral Proceedings for the Opposition of EP 1890681B1 (Application No. 06773194.3) (Mar. 17, 2011).
Third Amended Answer filed by Teva Pharmaceuticals USA, Inc and Teva Pharmaceuticals Industries, Ltd. Case No. 08-CV-10838 (Filed Aug. 6, 2010).
Third Amended Complaint for Patent Infringement against Teva Pharmaceuticals USA, Inc and Teva Pharmaceuticals Industries, Ltd. filed by Gilead Sciences, Inc., Emory University Case No. 08-CV-10838 (Jul. 6, 2010).
Third Office Action for Patent Application No. 97197460.8 issued by the Chinese Patent Office (Jun. 9, 2006) (translation).
Third Official Action for Patent Application No. a 2005 07947 issued by the Ukrainian Patent Office (2007) (translation).
Thornber "Isosterism and Molecular Modification in Drug Design" Chem. Soc. Reviews 18: 563-580, 1979.
Tisdale et al., "Rapid in vitro selection of human immunodeficiency virus type 1 resistant to 3'-thiacytidine inhibitors due to a mutation in the YMDD region of reverse transcriptase," Proc. Natl. Acad. Sci. USA 90:5653-5656 (1993).
Tsai et al., "Effects of (R)-9-(2-phophonylmethoxypropyl)adenine monotherapy on chronic SIV infection in macaques," Aids Res. & Hum. Retro. 13(8):707-712, 1997.
Tsai et al., "Prevention of SIV infection in macaques by (R)-9-(2-phosphonylmethoxypropyl)adenine," Science 270:1197-1199, 1995.
U.S. Department of Health and Human Services (2004) "Guidance for Industry Fixed Dose Combination and Co-Packaged Drug Products for Treatment of HIV—Draft Guidance" pp. 1-21.
Ueda et al., "Vinyl compounds of nucleic acid bases I. Synthesis of N-vinyluracil, N-vinylthymine, and N-vinyladenine," Die Makromolekulare Chemie 120:13-20, 1968.
USP 24 The United States Pharmacopeia (2000).
Wainberg et al. "In vitro selection and characterization of HIV-1 with reduced susceptability to PMPA," Antiviral Therapy 4:87-94 (1999).
Walmsley et al., "Gemini. A Noninferiority Study of Saquinavir/Ritonavir Versus Lopinavir/Ritonavir as Initial HIV-1 Therapy in Adults," J. Acquir. Immune Defic. Syndr. 50(4):367-374 (2009).
Wang et al. "Lack of Significant Pharmacokinetic Interactions between Emtricitabine and Other Nucleoside Antivirals in Healthy Volunteers," 41st ICAAC Abstracts, Chicago, IL, Sep. 22-25, 2001, Abstract A-505.
Wang et al. "Pharmacokinetic and pharmacodynamic characteristics of emtrictabine support its once daily dosing," Int. Conf. AIDS, Jul. 7-12 14:abstract TUPeB4546 (2002).
Weller et al., "Orally active Fibrinogen receptor antagonists. 2. Amidoximes as prodrugs of amidines," J. Med. Chem. 39:3139-3147, 1995.
Written Opinion issued by the ISA for PCT/US2006/023223 (Feb. 23, 2007).
Written Opinion of the ISA for PCT/US2006/023222 (Feb. 23, 2007).
Yeni et al., "Antiretroviral Treatment for Adult HIV Infection in 2002," JAMA 288(2):222-235 (2002).
Yuan et al., "Degradation Kinetics of Oxycarbonyloxymethyl Prodrugs of Phosphonates in Solution," Pharm. Res. 18(2):234-237 (2001).
Zhang et al. "Phase transformation considerations during process development and manufacture of solid oral dosage forms" Adv Drug Del Reviews 56(30), 371-390 (2004).
"Annex I. Summary of Product Characteristics," for Epivir, 9 pages.
"Annex I. Summary of Product Characteristics," for Truvada film-coated tablets, 14 pages.
"graph," and "convolute of graphs,", cited as documents D54 and D55 in opposition proeedings of EP 04701819.7, Statement of Appeal Grounds filed Jun. 24, 2011.
"Lactose Anhydrous," p. 373 in Analytical Profiles of Drug Substances, vol. 20, Ed. Klaus Florey, Academic Press, Inc. (1990).
"Lactose," Handbook of Pharmaceutical Excipients, 3rd ed. Ed. A.H. Kibbe, American Pharmaceutical Association, pp. 276-285 (2000) pp. 276-285 (2000).
"New Uses for Tenofovir; More Questions about d4T," Project Inform Perspective 35:15-16 (2003).
Ait-Khaled, et al., "Zidovudine appears to prevent selection of K65R and L74V mutations normally selected by abacavir mono- or combination therapies not containing zidovudine" Antiviral Therapy, 2002, 7:S107 (Abstract).
Arimilli et al., "Nucleotide Analogues," U.S. Appl. No. 60/022,708, 40 pages, filed Jul. 26, 1996.
Arzneiformenlehre. Ein Lehrbuch für Pharmazeuten, List et al., Eds., Wissenschaftliche Verlagsgesellschaft mbH, pp. 79 and 477 (1985). An English translation is not readily available. Applicants believe this reference discloses that preparations with lactose can undergo the Maillard reaction with amines. Such preparations result in discolorations. Amines and reducing sugars may also form N-glycosylamines which may react further in a Maillard reaction.
BioWorld Today, "About BioWorld," 1 page, http://www.bioworld.com/servlet/com.accumedia.web.Dispatcher?next=aboutUs (2010).
Borroto-Esoda et al., "In vitro evaluation of the anti-HIV activitiy and metaboloc interactions of tenofovir and emtricitabine," Antiviral Therapy 11:377-384 (2006).
Brogan et al., "Cost-Effectiveness of Nucleoside Revers Transcriptase Inhibitor Pairs in Efavirenz-Based Regimens for Treatment-Naïve Adults with HIV Infection in the United States," Value in Health 14:657-664 (2011).
Communication concerning Correction of the EP Specification for Patent Publication EP 1583542 (Application No. 04701819.7) issued by the European Patent Office (Jul. 22, 2008).
Communication of Notice of Opposition of EP 1583542 B1 (Application No. 04701819.7)—first information to the patent proprietor (Mar. 24, 2009).
Communication of Notice of Opposition of EP 1583542 B1 (Application No. 04701819.7)—first information to the patent proprietor (Mar. 26, 2009).

(56) References Cited

OTHER PUBLICATIONS

Communication pursuant to Article 94(3) EPC for Patent Publication EP 1923063 (Application No. 08152527.1) issued by the European Patent Office (Mar. 26, 2012).
Crowley, "Drug-Excipient Interactions," Pharm. Tech., 6 pages (2001).
Dahl et al., Amended Transmittal of U.S. Appl. No. 10/540,794, Compositions and methods for combination antiviral therapy, filed Mar. 20, 2006.
De Clercq, "New Anti-HIV Agents and Targets," Medicinal Research Reviews 22(6):531-565 (2002).
Decision to Grant a European patent for EP Appln No. 04701819.7 and Druckexemplar (May 23, 2008).
Department of Health and Human Services, "Guidelines for the Use of Antiretroviral Agents in HIV-1-infected Adults and Adolescents," pp. 1, 33-49 (Nov. 3, 2008).
Examiner's Second Report on Patent Application No. 2009200414 issued by the Australian Patent Office (Aug. 29, 2011).
European Search Report, EP 2386294 (Application No. 11167101.2), 15 pages (Dec. 29, 2011).
Eyjolfsson, "Lisinopril-Lactose Incompatibility," Drug Devel. Indust. Pharm. 24(8):797-798 (1998).
First Examination Report for Patent Application No. 6665/DELNP/2008 issued by the Indian Patent Office (Jun. 30, 2011).
FTC 101 Virology analysis, TPI Document No. 14022 (2002).
Gallant, et al., "Early Non-Response to Tenofovir DF (TDF) + Abacavir (ABC) and Lamivudine (3TC) in a Randomized Trial Compared to Efavirenz (EFV) + ABC and 3TC: ESS30009 Unplanned Interim Analysis," Abstr Intersci Conf Antimicrob Agents Chemother Intersci Conf Antimicrob Agents Chemother, Abstract No. H-1722a (2003).
Giron, "Applications of thermal analysis in the pharmaceutical industry," J. Pharm. Biomed. Anal. 4(6):755-770 (1986).
Glaxo Marketing Material, Epivir + Ziagen, 6 pages (2003).
Huff, "Five New Drugs Enter the Homestretch," The Body: The Complete HIV/AIDS Resource, 3 pages (2002).
Information About the Results of the Oral Proceedings for EP 1890681 B1 (Application No. 06773194.3) (Apr. 5, 2011).
Jamsek, et al. "Poor Virological Responses and Early Emergence of Resistance in Treatment Naïve, HIV-infected Patients Receiving a Once Daily Triple Nucleoside Regimen of Didanosine, Lamivudine, and Tenofovir DF" 11th Conf Retrovir Oppor Infect, Abstract No. 51 (2004).
Kusmierek et al., "Kinetics and Mechanisms of Hydrolytic Reactions of Methylated Cytidines under Acidic and Neutral Conditions," Acta Chem. Scand. 43:196-202 (1989).
Lanier, et al. "Prediction of NRTI Optins by Linking Reverse Transcriptase Genotype to Phenotypic Breakpoints" 10th Conf Retrovir Oppor Infect, Abstract No. 586 (2003).
Lindahl, "Instability and decay of the primary structure of DNA," Nature 362:709-715 (1993).
Lu, et al., "Determination of Clinical Cut-Offs for Reduced Response to Tenofovir DF therapy in Antiretroviral-Experienced Patients," Antiviral Therapy 7(1):S104, Abstract No. 125 (2002).
Marcelin et al., "Resistance profiles of emtricitabine and lamivudine in tenofovir-containing regimens," J. Antimicrob. Chemother. 67:1475-1478 (2012).
Margot et al., "In Vitro Human Immunodeficiency Virus Type 1 Resistance Selections with Combinations of Tenofovir and Emtricitabine or Abacavir and Lamivudine," Antimicrobial Agents and Chemotherapy 50(12):4087-4095 (2006).
Merck Index, 13th Edition, p. ONR-65 (2001).
Molina et al., "Castle: Atazanavir-Ritonavir vs Lopinavir-Ritonavir in Antiretroviral-Naïve HIV-1 Infected Patients: 96 Week Efficacy & Safety," 48th Annual ICAAC/IDSA 46th Annual Meeting, Washington, D.C., Presentation No. H-1250d (Oct. 25-28, 2008).
National Institutes of Health, "Guidelines for the Use of Antiretroviral Agents in HIV-1-Infected Adults and Adolescents," 9 pages (2011/2012).

Notice of Allegation and Detailed Statement in respect of Tenofovir Disoproxil Fumarate and Emtricitabine (Truvada®) and Canadian Patent Nos. 2,261,619 and 2,298,059, 56 pages (Nov. 22, 2011).
Notice of Allegation and Detailed Statement in respect of Truvada and Canadian Patent Nos. 2,512,475, 37 pages (Nov. 22, 2011).
Office Action for Korean Patent Application No. 7013069/2005 issued by the Korean Intellectual Property Office (Jan. 23, 2008).
Office Action, 10 pages, from U.S. Appl. No. 12/195,161 (mailed May 7, 2010).
Office Action, 10 pages, from U.S. Appl. No. 12/204,174 (mailed Oct. 1, 2009).
Office Action, 7 pages, from U.S. Appl. No. 10/540,794 (mailed Sep. 21, 2006).
Office Action, 8 pages, from U.S. Appl. No. 10/540,794 (mailed Oct. 31, 2007).
Office Action, 8 pages, from U.S. Appl. No. 12/204,174 (mailed Jun. 4, 2010).
Office Action, 9 pages, from U.S. Appl. No. 10/540,794 (mailed May 16, 2007).
Official Action and Preliminary Notice of Allowance from the Eurasian Patent Office for Application No. 200501134/28 (May 14, 2010).
Official Action for Application No. 2008-517083 issued by the Japanese Patent Office (Mar. 23, 2012) (translation).
Official Action for Patent Application No. 93100813 issued by the Taiwanese Intellectual Property Office (Mar. 16, 2011) (translation).
Official Action, 2 pages, from JP appl. No. 2010-175808 (mailed Nov. 6, 2012) translation attached.
Official Communication for Patent Application No. 2100/DEL/2007 issued by the Indian Patent Office (Jan. 16, 2013).
Opposition filed in Indian Patent Appl. No. 9661/DELNP/2007 by Cipla Limited (Jun. 30, 2009).
Osborne, "Gilead plans $300M notes sale to recoup some merger costs.(Gilead Sciences Inc.)," Bioworld Today, 13(239), 1 page (Dec. 16, 2002).
Osborne, "Gilead, Triangle Plan Merger: $464 Deal Pairs HIV Drugs," Bioworld Today 13(233):1,6 (2002).
Pharmaceutical Dosage Forms. Tablets. 2nd Ed., revised and expanded, Lieberman et al., eds., pp. 93 and 98 (1990).
Project Inform, "Perspective," pp. 1-28 (2003).
Quan et al., "Endogenous Reverse Transcriptase Assays Reveal Synergy between Combinations of the M184V and other Drug-Resistance-conferring Mutations in Interactions with Nucleoside Analog Triphosphates," J. Mol. Biol. 277:237-247 (1998).
Reply to the statement of appeal grounds, EP 1583542 B1 (Application No. 04701819.7), 50 pages (Oct. 18, 2011).
Request for Correction of EP Appln No. 04701819.7 (Jul. 8, 2008).
Request for Correction of EP Appln No. 04701819.7 (Jun. 27, 2008).
Response to the Noting of Loss of Rights pursuant to Rule 112(1) EPC dated Sep. 3, 2012, Patent Publication EP 2386294 (Application No. 11167101.2) (Nov. 13, 2012).
Response to the Noting of Loss of Rights pursuant to Rule 112(1)EPC dated Nov. 14, 2012, Patent Publication EP 1923063 (Application No. 08152527.1) (Jan. 24, 2013).
Response to the reply letter of Teva Pharmaceutical Industries Ltd. dated Oct. 18, 2011, EP 1583542 B1 (Application No. 04701819.7), 35 pages (Aug. 9, 2012).
Reversal of Rejection Decision for Application No. 200480002190.5 by the Patent Reexamination Board (Patent Office of the People's Republic of China) (Jun. 10, 2010).
Riaz and Ami, "Stability of Aminophylline," Pak. J. Pharm. Sci. 6(1):35-44 (1993).
Scrip, "Gilead Acquires Triangle for $464 Million," 2 pages (Dec. 6, 2002).
Second Office Action for Patent Application No. 200480002190.5 issued by the Patent Office of the People's Republic of China (May 11, 2011).
Smirnov et al., "A Comparative Study of the Kinetics of Cytarabine Hydrolytic Deamination in Aqueous Solutions," Pharm. Chem. J. 34(8):451-454 (2000).
Staszewski et al., NEJM, 1999, 341 5,1865-1873.

(56) References Cited

OTHER PUBLICATIONS

Teva Pharmaceutical Industries, Ltd, (Opponent), Opposition Brief against Israel Patent No. 169243 (dated Jul. 26, 2009).
Teva's Response to Patentee's Appeal, 5 pages, EP Pat. No. 1890681, EP Appl. No. 06773194.3 (mailed May 3, 2012).
Theory and Practice of Industrial Pharmacy, 3rd Edition, Lachman et al., Eds., Lea & Febiger, pp. 324-329 (1986).
Thoithi et al., "Investigation of the Kinetics of Degradation of Hexopyranosylated Cytosine Nucleosides Using Liquid Chromatography," Nucleosides, Nucleotides & Nucleic Acids 19(1 &2):189-203 (2000).
Truvada Patient Information Leaflet, 33 pages (2008).
Viread (Tenofovir Disoproxil Fumarate Tablets) Summary of Product Characteristics, EMEA, SmPC, 37 pages (Feb. 5, 2002).
Viread Label pp. 1-44 (2001).
Viread Patient Information Leaflet, 21 pages (2002).
Virji-Jeganathan, "BVV Stock Table Highlights," Bioventure View, 17(25): pp. 6-7 (Dec. 10, 2002).
Wang "FTC: A Potent and Selective Anti-HIV and Anti-HBV Agent Demonstrating Desirable Pharmacokinetic (PK Characteristics," Abstracts of the IDSA, 36th Annual Meeting, Session 58, Poster 415, Hepatits A, B, and C in HIV-Infected Persons Friday, 4-6 pm (1998).
Wirth et al., "Maillard Reaction of Lactose and Fluoxetine Hydrochloride, a Secondary Amine," J. Pharm. Sci. 87(1):31-39 (1998).
Zalac et al., "Paracetamol-Propyphenazone Interaction and Formulation Difficulties Associated with Eutectic Formation in Combination Solid Dosage Forms," Chem. Pharm. Bull. 47(3):302-307 (1999).
Affirmation of Andrew W. Williams in Support of Plaintiffs Merck, Sharp & Dohme Corp and Bristol-Myers Squib Company Co's Opening Claim Construction Brief and Exhibits Case No. 10-CV-01851 (Dec. 2, 2011).
Answer and Counterclaim filed by Teva Pharmaceuticals USA, Inc and Teva Pharmaceuticals Industries, Ltd. Case No. 09-CV-04463 (Aug. 10, 2009).
Answer to Amended Complaint filed by Teva Pharmaceuticals USA, Inc and Teva Pharmaceuticals Industries, Ltd. Case No. 10-CV-01796 (Jun. 29, 2011).
Complaint for Patent Infringement against Teva Pharmaceuticals USA, Inc and Teva Pharmaceuticals Industries, Ltd. filed by Gilead Sciences, Inc. Case No. 09-CV-04463 (May 8, 2009).
Declaration of Paul A. Bartlett in Support of Plaintiffs' Claim Constructions and Exhibits filed by Gilead Sciences, Inc., Emory University Case No. 08-CV-10838 (Nov. 4, 2011).
Declaration of Michael J. Freno in Support of Teva's Opening Claim Construction Brief and Exhibits filed by Teva Pharmaceuticals USA, Inc and Teva Pharmaceuticals Industries, Ltd. Case No. 08-CV-10838 (Nov. 4, 2011).
Declaration of Adam C. LaRock in Support of Plaintiffs' Claim Constructions and Exhibits filed by Gilead Sciences, Inc., Emory University Case No. 08-CV-10838 (Nov. 4, 2011).
Declaration of Adam C. LaRock in Support of Plaintiffs' Rebuttal Claim Constructions and Exhibits filed by Gilead Sciences, Inc., Emory University Case No. 08-CV-10838 (Dec. 16, 2011).
Declaration of Natalie Lieber and Exhibits filed by Gilead Sciences, Inc. Case No. 10-CV-01796 (Dec. 2, 2011).
Declaration of Natalie Lieber in Support of Plaintiffs' Rebuttal Claim Constructions and Exhibits filed by Gilead Sciences, Inc. Case No. 10-CV-01796 (Jan. 13, 2012).
Declaration of Daniel P. Margolis in Support of Teva's Opening Claim Construction Brief and Exhibits filed by Teva Pharmaceuticals USA, Inc and Teva Pharmaceuticals Industries, Ltd. Case No. 10-CV-01796 (Dec. 2, 2011).
Declaration of Daniel P. Margolis in Support of Teva's Rebuttal Claim Construction Brief and Exhibits filed by Teva Pharmaceuticals USA, Inc and Teva Pharmaceuticals Industries, Ltd. Case No. 08-CV-10838 (Dec. 16, 2011).
Declaration of Daniel P. Margolis in Support of Teva's Rebuttal Claim Construction Brief and Exhibits filed by Teva Pharmaceuticals USA, Inc and Teva Pharmaceuticals Industries, Ltd. Case No. 10-CV-01796 (Jan. 13, 2012).
Declaration of Allan S. Myerson in Support of Plaintiffs' Claim Constructions and Exhibits filed by Gilead Sciences, Inc. Case No. 10-CV-01796 (Dec. 2, 2011).
Declaration of Robin D. Rogers, Ph.D. in Support of Teva's Claim Constructions and Exhibits Case No. 10-CV-01851 (Jan. 13, 2012).
Declaration of Karen C. Shen in Support of Teva's Opening Claim Construction Brief and Exhibits Case No. 10-CV-01851 (Dec. 2, 2011).
Declaration of Slaven Jesic in Support of Teva's Rebuttal Claim Construction Brief and Exhibits Case No. 10-CV-01851 (Jan. 13, 2012).
Declaration of Andrew W. Williams in Support of Plaintiffs Merck, Sharp & Dohme Corp and Bristol-Myers Squib Company Co's Rebuttal Claim Construction Brief and Exhibits Case No. 10-CV-01851 (Jan. 13, 2012).
Defendants' Memorandum in Opposition to Plaintiff's Pretrial Memorandum filed by Teva Pharmaceuticals USA, Inc and Teva Pharmaceuticals Industries, Ltd. Case No. 10-CV-01796 (Jan. 28, 2013).
Defendants' Memorandum in Opposition to Plaintiffs' Pretrial Memorandum filed by Teva Pharmaceuticals USA, Inc and Teva Pharmaceuticals Industries, Ltd. Case No. 10-CV-01851 (May 24, 2013).
Defendants' Notice Pursuant to 35 U.S.C. § 282 filed by Merck, Sharp & Dohme Corp and Bristol-Myers Squib Company Co. Case No. 10-CV-01851 (May 22, 2013).
Defendants' Pretrial Memorandum filed by Teva Pharmaceuticals USA, Inc and Teva Pharmaceuticals Industries, Ltd. Case No. 10-CV-01796 (Jan. 14, 2013).
Defendants' Pretrial Memorandum filed by Teva Pharmaceuticals USA, Inc and Teva Pharmaceuticals Industries, Ltd. Case No. 10-CV-01851 (May 10, 2013).
Defendants' Proposed Findings of Fact and Conclusions of Law filed by Teva Pharmaceuticals USA, Inc and Teva Pharmaceuticals Industries, Ltd. Case No. 10-CV-01796 (Jan. 14, 2013).
Defendants' Proposed Findings of Fact and Conclusions of Law filed by Teva Pharmaceuticals USA, Inc and Teva Pharmaceuticals Industries, Ltd. Case No. 10-CV-01851 (May 10, 2013).
Letter to Judge Richard J. Sullivan Case No. 10-CV-01796 (Jan. 13, 2012).
Fourth Amended Answer filed by Teva Pharmaceuticals USA, Inc and Teva Pharmaceuticals Industries, Ltd. Case No. 08-CV-10838 (Oct. 17, 2011).
Fourth Amended Complaint for Patent Infringement against Teva Pharmaceuticals USA, Inc and Teva Pharmaceuticals Industries, Ltd. and Exhibits filed by Gilead Sciences, Inc., Emory University Case No. 08-CV-10838 (Oct. 3, 2011).
First Amended Complaint for Patent Infringement filed by Gilead Sciences, Inc. Case No. 10-CV-01796 (Jun. 15, 2011).
Merck, Sharp & Dohme Corp and Bristol-Myers Squib Company Co's Opening Claim Construction Brief Case No. 10-CV-01851 (Dec. 2, 2011).
Merck, Sharp & Dohme Corp and Bristol-Myers Squib Company Co's Rebuttal Claim Construction Brief Case No. 10-CV-01851 (Jan. 13, 2012).
Order signed by Judge Richard J. Sullivan Case No. 08-CV-10838 (May 26, 2010).
Order signed by Judge Richard J. Sullivan Case No. 10-CV-01798 (May 26, 2010).
Order signed by Judge Richard J. Sullivan Case No. 10-CV-01796 (Dec. 5, 2011).
Order signed by Judge Richard J. Sullivan Case No. 08-CV-10838 (Dec. 19, 2011).
Order signed by Judge Richard J. Sullivan Case No. 10-CV-01796 (Apr. 26, 2012).
Order signed by Judge Richard J. Sullivan Case No. 10-CV-01796 (Jan. 18, 2013).
Order signed by Judge Richard J. Sullivan Case No. 10-CV-01796 (Jan. 30, 2013).

(56) References Cited

OTHER PUBLICATIONS

Order signed by Judge Richard J. Sullivan Case No. 10-CV-01851 (May 14, 2013).
Order signed by Judge Richard J. Sullivan Case No. 10-CV-01851 (May 24, 2013).
Order signed by Judge Richard J. Sullivan Case No. 10-CV-01851 (Jun. 5, 2013).
Order signed by Judge Richard J. Sullivan Case No. 10-CV-01851 (Jul. 19, 2013).
Plaintiff's Opposition to Defendants' Pretrial Memorandum by Gilead Sciences, Inc. Case No. 10-CV-01796 (Jan. 28, 2013).
Plaintiffs' Opening Claim Construction Brief filed by Gilead Sciences, Inc., Emory University Case No. 08-CV-10838 (Nov. 4, 2011).
Plaintiff's Opening Claim Construction Brief filed by Gilead Sciences, Inc. Case No. 10-CV-01796 (Dec. 2, 2011).
Plaintiffs' Opening Pretrial Brief filed by Merck, Sharp & Dohme Corp and Bristol-Myers Squib Company Co. Case No. 10-CV-01851 (May 10, 2013).
Plaintiff's Pretrial Memorandum filed by Gilead Sciences, Inc. Case No. 10-CV-01796 (Jan. 14, 2013).
Plaintiff's Proposed Findings of Fact and Conclusions of Law filed by Gilead Sciences, Inc. Case No. 10-CV-01796 (Jan. 14, 2013).
Plaintiffs' Proposed Findings of Fact and Conclusions of Law filed by Merck, Sharp & Dohme Corp and Bristol-Myers Squib Company Co. Case No. 10-CV-01851 (May 10, 2013).
Plaintiffs' Rebuttal Claim Construction Brief filed by Gilead Sciences, Inc., Emory University Case No. 08-CV-10838 (Dec. 16, 2011).
Plaintiffs' Rebuttal Claim Construction Brief filed by Gilead Sciences, Inc., Emory University Case No. 10-CV-01796 (Jan. 13, 2012).
Plaintiffs' Reply to Teva USA's Counterclaim filed by Gilead Sciences, Inc., Emory University Case No. 09-CV-04463 (Aug. 31, 2009).
Plaintiffs' Response to Defendants' Pretrial Memorandum filed by Merck, Sharp & Dohme Corp and Bristol-Myers Squib Company Co. Case No. 10-CV-01851 (May 24, 2013).
Request for Leave to Submit Supplemental Expert Witness Affidavit of Jerry L. Atwood, Ph.D. on behalf of Plaintiffs filed by Merck, Sharp & Dohme Corp and Bristol-Myers Squib Company Co. Case No. 10-CV-01851 (May 24, 2013).
Stipulation and Agreement Regarding U.S. Pat. Nos. 5,922,965, 5,935,946, 5,977,089, and 6,043,230 Case No. 10-CV-01796 (Oct. 9, 2012).
Teva's Opening Claim Construction Brief filed by Teva Pharmaceuticals USA, Inc and Teva Pharmaceuticals Industries, Ltd. Case No. 08-CV-10838 (Nov. 4, 2011).
Teva's Opening Claim Construction Brief filed by Teva Pharmaceuticals USA, Inc and Teva Pharmaceuticals Industries, Ltd. Case No. 10-CV-01796 (Dec. 2, 2011).
Teva Pharmaceuticals USA, Inc and Teva Pharmaceuticals Industries, Ltd.'s Opening Claim Construction Brief Case No. 10-CV-01851 (Dec. 2, 2011).
Teva's Rebuttal Claim Construction Brief filed by Teva Pharmaceuticals USA, Inc and Teva Pharmaceuticals Industries, Ltd. Case No. 08-CV-10838 (Dec. 16, 2011).
Teva's Rebuttal Claim Construction Brief filed by Teva Pharmaceuticals USA, Inc and Teva Pharmaceuticals Industries, Ltd. Case No. 10-CV-01796 (Jan. 13, 2012).
Teva Pharmaceuticals USA, Inc and Teva Pharmaceuticals Industries, Ltd.'s Rebuttal Claim Construction Brief Case No. 10-CV-01851 (Jan. 13, 2012).
Transcript of Proceedings held on Apr. 26, 2012 Case No. 10-CV-01796.
Transcript of Proceedings held on Oct. 3, 3012, 2012 Case No. 10-CV-01796.
Bloor S., et al, Patterns of HIV drug resistance in routine clinical practice; a survey of almost 12000 samples from the USA in 1999, Antiviral Therapy 5(3):132.
Carpenter, C.C.J., et al., "Antiretroviral Therapy for HIV Infection in 1997: Updated Recommendations of the International AIDS Society—USA Panel," The Journal of the American Medical Association 277(24):1962-1969 (Jun. 25, 1999).
Cherry, et al., "Mutations at codon 184 in simian immunodeficiency virus reverse transcriptase confer resistance to the (−) enantiomer of 2,,3'-dideoxy-3,-thiacytidine," Antimicrob., Agents Chemother. 41:2763-2765 ( 1997) http://aac.asm.org/content/41/12/2763.full.pdf+html (retrieved on Jan. 29, 2014).
Delehanty J., et al., "Selection of FTC dose based on viral kinetics and pharmacokinetics in an accelerated clinical trial design,"12th World AIDS Conference, Geneva, Switzerland, Abstract No. 12208 (Jul. 1998) http://www.aegis.org/DisplayContent/print.aspx?Section1D=341007 (retrieved on Jan. 30, 2014).
Flexner, C., "HIV-Protease Inhibitors," The New England Journal of Medicine 338(18):1281-1292 (Apr. 30, 1998).
Gosselin, et al., "Anti-human immunodeficiency virus activities of the (3-L enantiomer of 2',3'-dideoxycytidine and its 5-fluoro derivative in vitr,"Antimicrob Agents Chemother 38: 1292-1297 (1994) http://aac.asm.org/content/38/6/1292.full.pdf (retrieved on Jan. 30, 2014).
Harrigan, P.R., et al., "Phenotypic susceptibilities to tenofovir in a large panel of clinically derived human immunodeficiency virus type 1 isolates," Antimicrob Agents Chemother. 46:1067-1072 (2002) http://aac.asm.Org/content/46/4/1067.full.pdf+html (retrieved on Jan. 30, 2014).
Miller, Margot N.A., et al., "Antiviral activity of tenofovir (PMPA) against nucleoside-resistant clinical HIV samples,"Nucleosides Nucleotides Nucleic Acids,; 20:1025-1028 (2001).
Miller M.D., et al., Human Immunodeficiency Virus Type 1 Expressing the Lamivudine-Associated M184V Mutation in Reverse Transcriptase Shows Increased Susceptibility to Adefovir and Decreased Replication Capability in Vitro, The Journal of Infectious Diseases 179:92-100 (1999) http://jid.oxfordjournals.org/content/179/1/92.full.pdf (retrieved on Jan. 30, 2014).
Robinson B.S., et al. BMS-232632, a Highly Potent Human Immunodeficiency Virus Protease Inhibitor That Can Be Used in Combination with Other Available Antiretroviral Agents.—Antimicrobial Agents and Chemotherapy 44(8):2093-2099 (Aug. 2000) http://www.ncbi.nhn.nih.gov/pmc/articles/PMC90019/pdf/acQ02093.pdf (retrieved on Jan. 30, 2014).
Srinivas R.V. et al., "Antiviral Activities of 9-R-2-Phosphonomethoxypropyl Adenine (PMPA) and Bis(isopropyloxymethylcarbonyl)PMPA against Various Drug-Resistant Human Immunodeficiency Virus Strains," Antimicrob. Agents Chemother 42(6):1484-1487 (Jun. 1988) http://aac.asm.org/content/42/6/1484.full.pdf+html (retrieved on Jan. 30, 2014).
Staszewski S., et al., "Efficacy and safety of tenofovir disoproxil fumarate (TDF) versus stavudine (d4T) when used in combination with lamivudine (3TC) and efavirenz (EFV) in HIV-1 infected patients naive to antiretroviral therapy (ART): 48-week interim results," XIV International AIDS Conference, Barcelona, Spain, Abstracts No. 9804:7-12 (Jul. 2002) http://www.iasocietv.org/Default.aspx?page1d=12&abstract1d=9804 (retrieved on Jan. 30, 2014).
Van Rompay, K. K., et al., "Virulence and reduced fitness of simian immunodeficiency virus with the M184V mutation in reverse transcriptase," J. Virology, 76(12):6083-6092 (2002) http://www.ncbi.nlm.nih.gov/pmc/articles/PMC136201/pdf/0196.pdf (retrieved on Jan. 30, 2014).
Van Rompay, et al., "9-[2-(Phosphonomethoxy)propyl]adenine therapy of established simian immunodeficiency virus infection in infant rhesus macaques," Antimicrob. Agents Chemother. 40:2586-2591 (1996 ) http://www.ncbi.nlm.nih.gov/pmc/articles/PMC163581/pdf/402586.pdf (retrieved on Jan. 31, 2014).
Zao, Biokad Objection against the application of Eurasian Patent No. 015145 in the Russian Federation dated Jul. 10, 2013.
Patent Examination Report No. 1, Australia patent appl. No. 2011253996, 2 pages (Nov. 15, 2012).
Office Action for Patent Application No. 200680026180.4 issued by the Chinese Patent Office (May 29, 2013) (translation).
Summons to attend Oral Proceedings EPO for Application No. 067731595.0 dated Jul. 9, 2013.

(56) References Cited

OTHER PUBLICATIONS

Communication and Annex from PO for Application No. 067731595.0 dated Jul. 9, 2013.
Response to Summons and Annex rom EPO for Application No. 067731595.0 dated Sep. 25, 2013.
Brief Communication from EPO for Application No. 067731595.0 dated Nov. 10, 2013.
Communication from EPO for Application No. 067731595.0 dated Nov. 15, 2013.
Minutes of Oral Proceedings from EPO for Application Application No. 067731595.0 dated Nov. 25, 2013.
Communication from EPO for Application No. 067731595.0 dated Dec. 4, 2013.
Excerpt of The Merck Veterinary Manual (Clarence M. Fraser et al. eds., 7th ed., 1991).
Excerpts from Daniel S. Kemp & Frank Vellaccio, Organic Chemisty (Worth Publishers, Inc. 1980).
Excerpts from K. Peter C. Vollhardt, Organic Chemistry (W.H. Freeman and Company 1987).
Excerpts from the Reexamination of U.S. Pat. No. 6,043,230.
Excerpts of Teva Pharmaceuticals USA, Inc.'s Detailed Statement of the Factual and Legal Bases for Its Opinion That U.S. Pat. Nos. 5,814,639, 5,914,331, 5,922,695, 5,935,946, 5,977,089. and 6,043,230 are Invalid, Unenforceable or Not Infringed by the Manufacture, Use or Sale of Its Emtricitabine & Tenofovir Disoproxil Fumarate Tablets, 200 mg/300 mg dated Jan. 28, 2010 ("2010 Detailed Statement").
Excerpts of Panel on Antiretroviral Guidelines for Adults and Adolescents, Department of Health and Human Services, Guidelines for the use of antiretroviral agents in HIV-1-infected adults and adolescents 1-167 (20 11 ).
Excerpts of Teva Pharmaceuticals USA, Inc.'s Detailed Statement of the Factual and Legal Bases for Its Opinion That U.S. Pat. Nos. 6,642,245 and 6,703,396 are Invalid, Unenforceable or Not Infringed by the Manufacture, Use or Sale of Its Emtricitabine & Tenofovir Disoproxil Fumarate Tablets, 200 mg/300 mg dated Nov. 3, 2008 ("2008 Detailed Statement"); "Teva Pharmaceuticals USA, Inc.'s Detailed Statement of the Factual and Legal Bases for Its Opinion That U.S. Pat. Nos. 6,642,245 and 6, 703,396 Are Invalid, Unenforceable or Not Infringed by the Manufacture, Use or Sale of Its Efavirenz/Emtricitabine/Tenofovir Disoproxil Fumarate Tablets, 600 mg/200 mg/300 mg" dated Mar. 30, 2009 ("2009 Detailed Statement"); and Teva Pharmaceuticals USA, Inc.'s Detailed Statement of the Factual and Legal Bases for Its Opinion That U.S. Pat. Nos. 5,814,639, 5,914,331, 5,922,695, 5,935,946, 5,977,089 and 6,043,230 are Invalid, Unenforceable or Not Infringed by the Manufacture, Use or Sale of Its Emtricitabine & Tenofovir Disoproxil Fumarate Tablets, 200 mg/300 mg dated Jan. 28, 2010 ("2010 Detailed Statement").
Excerpts of the Gilead Sciences, Inc., Q2, 2011 Earnings Results Conference Call and Webcast presentation, pp. 16 & 19 (Jul. 26, 2011).
Excerpts of the Gilead Sciences, Inc., Q2, 2011 Earnings Results Conference Call and Webcast presentation, p. 16-18 (Jul. 26, 2011).
Fischl, Margaret A. et al., Prolonged Zidovudine Therapy in Patients with AIDS and Advanced AIDS-Related Complex, 262 J.A.M.A. 2405 (1989).
Harada, Shinji et al., *Infection of HTLV-III/LAV in HTLV-I-Carrying Cells MT-2 and MT-4 and Application in a Plaque Assay*, 229 Science 563 (1985).
Hoong, Lee K. et al., Enzyme-Mediated Enantioselective Preparation of Pure Enantiomers of the Antiviral Agent 2',3'-Dideoxy-5-. fluoro-3 '-thiacytidine (FTC) and Related Compounds, 57 J. Organic Chemistry 5563 (1992).
Larder, Brendan A. et al., HIV with Reduced Sensitivity to Zidovudine (AZT) Isolated During Prolonged Therapy, 243 Science 1731 (1989).
Norton, Telly M. et al., Efficacy of Acyclovir Against Herpesvirus Infection in Quaker Parakeets, 52(12) Am. J. Vet. Res. 2007-09 (Dec. 1991).

Order signed by Judge Richard J. Sullivan Case No. 10-CV-01796 (Jan. 17, 2012).
Stella, Valentino J. et al., *Prodrugs and Site-Specific Drug Delivery*, 23 Journal of Medicinal Chemistry 1275 (1980).
Teva Pharmaceuticals USA, Inc.'s Detailed Statement of the Factual and Legal Bases for Its Opinion That U.S. Pat. Nos. 5,922,695, 5,935,946, 5,977,089, and 6,043,230 are Invalid, Unenforceable or Not Infringed by the Manufacture, Use or Sale OfTenofovir Disoproxil Fumarate Tablets, 300 mg dated Jan. 25, 2010("2010 Detailed Statement").
Castello and Mattocks, "Discoloration of Tablets Containing Amines and Lactose," J. Pharm. Sci. 51(92):106-108 (Feb. 1962).
"Pill" Encarta Dictionary, 2 pages (2009), retrieved from encarta.msn.com on Mar. 16, 2009.
"Time-Release," Compact Oxford English Dictionary, 1 page (2009), retrieved from www.askoxford.com/concise_oed on Mar. 12, 2009.
Petition for Inter Partes Review of U.S. Pat. No. 5,922,695, for Case No. IPR2014-00885, filed Jun. 4, 2014, 75 pages.
Corrected Petition for Inter Partes Review of U.S. Pat. No. 5,922,695, for Case No. IPR2014-00885, filed Jun. 24, 2014, 74 pages.
Related Matters for Case No. IPR2014-00885, filed Jun. 25, 2014, 6 pages.
Patent Owner Preliminary Response for Case No. IPR2014-00885, filed Sep. 18, 2014, 69 pages.
Moyle, Graeme and Gazzard,Brian, "Current Knowledge and Future Prospects for the Use of HIV Protease Inhibitors," 51:701-712, Drugs, May 1996.
Danner, et al., "A Short-Term Study of the Safety, Pharmacokinetics, and Efficacy of Ritonavir, and Inhibitor of HIV-1 Protease," 333:1528-1533, The New England Journal of Medicine, Dec. 1995.
Link, Derek; "The Collapse of Early Intervention at the Ninth International AIDS Conference," 7(6) Treatment Issues, 1993.
Bechtel-Boenning,Christine;"State of the Art Antiviral Treatment of HIV Infection," 31:1-13, NIH Nursing Clinics of North America, Mar. 1996.
Leary, Warren E.; "F.D.A. Panel Urges Fast Action on Approving a New AIDS Drug," N.Y. Times, Nov. 8, 1995.
HIV/AIDS Historical Time Line 1995-1999, FDA, 6 pages.
Vistide® (cidofovir injection) Package Insert, 2 pages.
Lacy et al., "Evaluation of the Subchronic Toxicity of an Oral Prodrug of the Anti-HIV Nucleotide Analog (9-2-Phosphonylmethoxyethyl)Adenine (PMEA)," 15(1) at 179 Abstract 958, Abstracts of the 34th Annual Meeting of the Society of Toxicology, 1995.
Lalezari et al., "(S)-1-[3-Hydroxy-2-(Phosphonylmethoxy)propyl] cytosine (Cidofovir): Results of Phase I/II Study of a Novel Antiviral Nucleotide Analogue," 171:788-796, The Journal of Infectious Diseases, 1995.
Foscavir® (foscarnet sodium) Package Insert, 2 pages.
Lee, William A. and Martin, John C., "Perspectives on the development of acyclic nucleotide analogs as antiviral drugs", 71:254-259, Antiviral Research, 2006.
Park et al., "Acyclovir Permeation Enhancement Across Intestinal and Nasal Mucosae by Bile Salt-Acylcarnitine Mixed Micelles," 9:1262-1267, Pharmaceutical Research, 1992.
Fix et al., "Acylcarnitines: drug absorption-enhancing agents in the gastrointestinal tract," 251:G332-G340, Am. J. Physiol., 1986.
Fleisher et al., "Improved oral drug delivery: solubility limitations overcome by the use of prodrugs," 19:115-130, Advanced Drug Delivery Reviews, 1996.
Starrett et al., "Synthesis, Oral Bioavailability Determination, and in Vitro Evaluation of Prodrugs of the Antiviral Agent 9-[2-(Phosphonomethoxy)ethyl]adenine (PMEA)," 37:1857-1864, Journal of Medicinal Chemistry, 1994.
Negi et al., "Studies on Orally Active Cephalosporins: Synthesis and Structure-Activity Relationships of New 3-Substituted Carbamoyloxymethyl Cephalosporins," 47:1507-1525, The Journal of Antibiotics, 1994.
Safadi et al., "Phosphoryloxymethyl Carbamates and Carbonates Novel Water—Soluble Prodrugs for Amines and Hindered Alcohols," 10:1350-55, Pharmaceutical Research, 1993.

(56) References Cited

OTHER PUBLICATIONS

Samara et al., "Pharmacokinetic Analysis of Diethylcarbonate Prodrugs of Ibuprofen and Naproxen," 16:201-210, Biopharmaceutics & Drug Disposition, 1995.
World Health Organization Model List of Essential Medicines, 18th Ed. (2013), 47 pages.
Institution Decision Case No. IPR2014-00885, filed Dec. 9, 2014, 23 pages.
Mylan's Updated Exhibit List, Case No. IPR2014-00885, dated Jan. 7, 2015, 9 pages.
Rehearing Request, Case No. IPR2014-00885, dated Jan. 8, 2015, 17 pages.
U.S. Pat. No. 5,922,695C1 (Ex Parte Reexamination Certificate) to Murty N. Arimilli, Kenneth C. Cundy, Joseph P. Dougherty, Choung U. Kim, Reza Oliyai and Valentino J. Stella, issued on Oct. 14, 2008 (Mylan's Updated Exhibit List Jan. 7, 2015.
U.S. Pat. No. 5,922,695 Prosecution File History U.S. Appl. No. 08/900,746, filed Jul. 25, 1997.
U.S. Pat. No. 5,922,695 Reexamination File History Reexamination Request U.S. Appl. No. 90/008,555, filed Apr. 30, 2007.
U.S. Pat. No. 5,977,089C1 (Ex Parte Reexamination Certificate) to Murty N. Arimilli, Kenneth C. Cundy, Joseph P. Dougherty, Choung U. Kim, Reza Oliyai and Valentino J. Stella, issued on Nov. 25, 2008.
U.S. Pat. No. 5,977,089 Reexamination File History Reexamination Request U.S. Appl. No. 90/008,550, filed Apr. 30, 2007.
U.S. Pat. No. 6,043,230 (Ex Parte Reexamination Certificate) to Murty N. Arimilli, Kenneth C. Cundy, Joseph P. Dougherty, Choung U. Kim, Reza Oliyai and Valentino J. Stella, issued on Oct. 14, 2008.
U.S. Pat. No. 6,043,230 Prosecution File History U.S. Appl. No. 09/314,606, filed May 19, 1999.
U.S. Pat. No. 6,043,230 Reexamination File History Reexamination Request U.S. Appl. No. 90/008,549, filed Apr. 30, 2007.
U.S. Pat. No. 5,935,946C1 (Ex Parte Reexamination Certificate) to John D. Munger, Jr., John C. Rohloff and Lisa M. Schultze, issued on Oct. 14, 2008.
U.S. Pat. No. 5,935,946 Prosecution File History U.S. Appl. No. 08/900,752, filed Jul. 25, 1997.
U.S. Pat. No. 5,935,946 Reexamination File History Reexamination Request U.S. Appl. No. 90/008,556, filed Apr. 30, 2007.
*Gilead Sciences, Inc. v. Teva Pharmaceuticals USA, Inc. et al.*, 10cv-07196-RJS (S. Dist. NY (Foley Square)) (consolidation of 08-cv-10838; 12-cv-06351; 12-cv-06294; 12-cv-07910), dated Feb. 4, 2014, 1618 pages.
Fischl, M.A., et al., "The Efficacy of Azidothymidine (AZT) in the Treatment of Patients with AIDS and AIDS Related Complex," New England J. Med. 317:185 (1987).
Richman, D. et al., "The Toxicity of Azidothymidine (AZT) in the Treatment of Patients with AIDS and AIDS Related Complex," New England J. Med. 317:192 (1987).
Larder, B.A., Darby, G. and Richman, D., "HIV with reduced sensitivity to zidovudine (AZT) isolated during prolonged therapy," Science 243:1731 (1989).
Kieburtz, KD, et al "Extended follow-up of peripheral neuropathy in patients with AIDS and AIDS related complex treated with dideoxyinosine," J. Acquir. Immune Defic. Syndr. 5:60 (1992).
Allan, J.D., et al. "Long term follow-up of didanosine administered orally twice daily to patients with advanced human immunodeficiency virus infection and hematologic intolerance of zidovudine," Clin. Infect. Dis. 16(S1):S46 (1993).
Simpson, D.M. and Tagliati, M., "Nucleoside Analogue Associated Peripheral Neuropathy in Human Immunodeficiency Virus Infection," J. Acquir. Immune Defic. Syndr. 9:153 (1995).
Van Leeuwen, R., et al., "Evaluation of Safety & Efficacy of 3TC (Lamivudine) in Patients with Asymptomatic or Mildly Symptomatic Human Immunodeficiency Virus Infection: A Phase I/II Study," J. Infect. Dis. 171:1166 (1995).

Beck, EJ., et al. "Survival and the use and costs of hospital services for London AIDS patients treated with AZT," Int. J. STD AIDS 7:507 (1996).
Boucher, C., et al., "High level Resistance to (-31 ) Enantiomeric 2',Deoxy3'-Thiacytidine in Vitro is Due to One Amino Acid Substitution in the Catalytic Site of Human Immunodeficiency Virus Type 1 Reverse Transcriptase," Antimicro. Agents Chemother. 37:2231 (1993).
Mayers, D., "Rational Approaches to Resistance: Nucleoside Analogues," AIDS 10(S1):S913 (1996).
Cleland, A. Watson, HG, Robertson, P., Ludlum, CA and Brown, HA, "Evolution of zidovudine resistance genotype in HumaImmunodeficiency Virus I in infected patients," AIDS 12:618 (1996).
Anderson, BD, Shirasaka, T, Kojima E, Yarchoan, R and Mitsuya H, "Identification of drug related genotypic changes in HIV1 from serum using the selective polymerase chain reaction," Antiviral Res. 25:24558 (1994).
Volberding, P., "The Need for Additional Options in the Treatment of Human Immunodeficiency Virus Infection," J. Infect. Diseases 171(S2):150 (1995).
Holy, A., Rosenberg, I., Dvorakova, H. and DeClercq, E., "Synthesis and Evaluation of Acyclic Nucleotide Analogs," Nucleosides & Nucleotides 7:667 (1988).
Srinivas, R., Robbins, B., Connelly,M, Gong, Y., Bischofberger, B., Fridland, A., "Metabolism and in Vitro Antiretroviral Activities of Bis(Pivaloyloxymethyl) Prodrugs of Acyclic Nucleoside Phosphonates," Antimicro. Agents Chemother. 37:2247 (1993).
Heljtink, R.A., et al , "Inhibitory effects of acyclic nucleoside phosphonates on human hepatitis B virus and duck hepatitis B virus infections in tissue culturQ," Antimicrobial. Agents Chemotherap. 38:2180 (1994).
Tsai, C., et al., "Prevention of SIV Infection in Macaques by (R)9(2Phosphonylmethoxypropyl)adenine," Science 270:1197 (1995).
Cohen, J., "New Drug Shows Promise in Monkeys," Science 220:1121 (1995).
Gong, Y., Marshall, D., Srinivas, R., Fridland, A., "Susceptibilities of zidovudineresistant variants of human immunodeficiency virus type 1 to inhibitor by acyclic nucleoside phosphonates," Antimicrobial Agents Chemother. 38:1683 (1994).
Examiner's Amendment and Notice of Allowability (dated Apr. 14, 1998), 5 pages.
Kubo, et al. "Nonpeptide angiotensin II receptor antagonists. Synthesis and biological activity of benzimidazolecarboxylic acids." J Med Chem. 1993 vol. 36, Issue No. 15, pp. 2343-2349.
Balzarini, et al. "Differential Antiherpesvirus and Antiretrovirus Effects of the (S) and (R) Enantiomers of Acyclic Nucleoside Phosphonates: Potent and Selective in Vitro and in Vivo Antiretrovirus Activities of (R)-9-(2-Phosphonomethoxypropyl)-2,6-Diaminopurine" Antimicrobial Agents and Chemotherapy, 1993, vol. 37, No. 2, p. 332-338.
James, John S. "AIDS Treatment News, PMPA in Perspective" AIDS Treatment News Issue No. 236, Dec. 1, 1995.
Editorials, "Carnitine Deficiency" Lancet 335:631-33 (1990).
Islam, I., Hinshaw, R., Chong, K-T., Kato,A., Borchardt, R. and Fisher, J.F. "Synthesis and Antiviral Activity of [2-[[4-[3-[(1-Methylethyl)amino]-2-Pyridyl]—Piperazinyl]Carbonyl]-1H-Indol-5-yl] (BHAP) Acylsphingosine HIV Reverse Transcriptase Inhibitors," Bioorg. Chem. 23:499-511 (1995).
De Clercq, E., "Antiviral Therapy for Human Immunodeficiency Virus Infections," Clin. Microbiol. Rev. 8:200-239 (1995).
Bundgaard, H., "Design of prodrugs," pp. 4-5, (1985) 1 page.
Holme, E. et al., "Carnitine deficiency induced by pivampicillin and pivmecillinam therapy" Lancet 2(8661):469-73 (1989).
"Federal Food and Drug Administration Guidance (Drugs) Development of New Stereoisomeric drugs", Chirality, vol. 4, Issue 5, pp. 338-340, 1992.
Bighley, L.D., et al. "Salt forms of drugs and absorption" in Encyclopedia of Pharm. Tech., Eds. J. Swarbrick and J.C. Boylan, vol. 13 (Marcel Dekker, Inc., New York) (1996), 49 pages.
Gould, Phillip L. "Salt selection for basic drugs", International Journal for Pharmaceutics, (1986) vol. 33, pp. 201-217.
Bisoprolol Fumarate Label (Final Printed Labeling, May 1, 1992).

(56) References Cited

OTHER PUBLICATIONS

Bischofberger, N, et al. "Bis(POC)PMPA, an orally bioavailable prodrug of the antiretroviral agent PMPA" Conf. on Retroviruses and Opportunistic Infections 4th:104 (abstract No. 214) (Jan. 22-26, 1997).
Expert Declaration of J. Allen McCutchan, M.D., M.Sc. (Dated May 29, 2014).
Expert Declaration of Jed F. Fisher Ph.D. (Dated Jun. 3, 2014).
Bordwell, F.G. "Equilibrium Acidities in Dimethyl Sulfoxide Solution" Acc. Chem. Res. (1988) vol. 21, pp. 456-463.
Miyazaki, T., Yanagida, S., Itoh, A., and Okahara, M., "Synthesis and Alkali-cation Complexing Properties of 12-Crown-4 Derivatives", The Chemical Society of Japan, Bull. Chem. Soc. Jpn., (1982) vol. 55, pp. 2005-2009.
Petition for Inter Partes Review of U.S. Pat. No. 5,935,946 for Case No. IPR2014-00886, filed Jun. 4, 2014, 75 pages.
Corrected Petition for Inter Partes Review of U.S. Pat. No. 5,922,695, for Case No. IPR2014-00886, filed Jun. 24, 2014, 74 pages.
Related Matters for Case No. IPR2014-00886, filed Jun. 25, 2014, 6 pages.
Patent Owner Preliminary Response for Case No. IPR2014-00886, filed Sep. 18, 2014, 70 pages.
Institution Decision Case No. 1PR2014-00886, filed Dec. 9, 2014, 21 pages.
Mylan's Updated Exhibit List, Case No. IPR2014-00886, dated Jan. 7, 2015, 9 pages.
Request for Rehearing IPR2014-00886, dated Jan. 16, 2014, 15 pages.
Physician's Desk Reference (51 ed. 1997), 28 pages.
Famvir® Package Insert, 16 pages.
Hepsera® Package Insert, 29 pages.
Bastin et al., Organic Process Research and Development, 4:427-435, 2000.
Van Westrenen et al., "The synthesis of polyhydroxycarboxylates. Part 6. N-Alkylation of amino compounds by a Michael-type addition with maleate," Recl. Tray. Chim. Pays-Bas, 109:474-478, 1990.
Stahl and Basel, Characterization and Improvement of the Stability Behaviour of Drug Substances in Stability Testing in the EC, Japan and the USA 56 (Dr. Wolfgang Grimm and Dr. Kurt Krummen, eds., 1993.
Petition for Inter Partes Review of U.S. Pat. No. 5,977,089, for Case No. IPR2014-00887, filed Jun. 4, 2014, 64 pages.
Corrected Petition for Inter Partes Review of U.S. Pat. No. 5,977,089, for Case No. IPR2014-00887, filed Jun. 24, 2014, 63 pages.
Related Matters for Case No. IPR2014-00887, filed Jun. 25, 2014, 6 pages.
Patent Owner Preliminary Response for Case No. IPR2014-00887, filed Sep. 18, 2014, 69 pages.
Institution Decision Case No. IPR2014-00887, filed Dec. 9, 2014, 17 pages.
Mylan's Updated Exhibit List, Case No. IPR2014-00887, dated Jan. 7, 2015, 9 pages.
Rehearing Request, Case No. IPR2014-00887, dated Jan. 8, 2015, 17 pages.
Petition for Inter Partes Review of U.S. Pat. No. 6,043,230, for Case No. IPR2014-00888, filed Jun. 4, 2014, 65 pages.
Corrected Petition for Inter Partes Review of U.S. Pat. No. 6,043,230, for Case No. IPR2014-00888, filed Jun. 24, 2014, 64 pages.
Related Matters for Case No. IPR2014-00888, filed Jun. 25, 2014, 6 pages.
Patent Owner Preliminary Response for Case No. IPR2014-00888, filed Sep. 28, 2014, 67 pages.
Institution Decision Case No. IPR2014-00888, filed Dec. 9, 2014, 20 pages.
Mylan's Updated Exhibit List, Case No. IPR2014-00888, dated Jan. 7, 2015, 9 pages.
Rehearing Request, Case No. IPR2014-00888, dated Jan. 8, 2015, 17 pages.
Complaint for Patent Infringement. Document filed by Emory University, Gilead Sciences, Inc, Case No. 1:12-cv-06293-RJS (Filed: Aug. 16, 2012), 14 pages.
Lupins Limited's Answer, Separate Defenses, and Counterclaims to Plaintiffs' Complaint. Document filed by Lupin Limited, Case No. 1:12-cv-06293-RJS (Filed Oct. 22, 2012), 21 pages.
Plaintiffs' Reply to Defendant's Counterclaims. Document filed by Emory University, Gilead Sciences, Inc., Case No. 1:12-cv-06293-RJS (Filed: Nov. 9, 2012), 10 pages.
Letter to Judge Richard J. Sullivan from Peter J. Curtin dated Sep. 3, 2013 Case No. 1:12-cv-06293-RJS (Filed: Sep. 4, 2013), 1 page.
Stipulation and Agreement Regarding U.S. Pat. Nos. 6,703,396, 6,642,245, 5,814,639 and 5,914,331: Case No. 1:12-cv-06293-RJS (Dated: Sep. 4, 2013), 6 pages.
Letter to Judge Richard J. Sullivan from David B. Bassett dated Sep. 16, 2014 re: Settlement. Document filed by Emory University, Gilead Sciences, Inc., Case No. 1:12-cv-06293-RJS (Filed: Sep. 16, 2014), 1 page.
Exhibit A to Letter addressed to Judge Richard J. Sullivan from David B. Bassett dated Sep. 16, 2014 re: Settlement. Document filed by Emory University, Gilead Sciences, Inc., Case No. 1:12-cv-06293-RJS (Filed: Sep. 16, 2014).
Order on Stipulation for Dismissal of Plaintiffs, Gilead Sciences, Inc. ("Gilead") and Emory University ("Emory"), and Defendant, Lupin Limited ("Lupin"), Case No. 1:12-cv-06293-RJS (Dated: Sep. 17, 2014), 2 pages.
Complaint for Patent Infringment. Document filed by Gilead Sciences, Inc., Case No. 1:12-cv-07910-RJS (Filed: Oct. 24, 2012), 9 pages.
Lupins Limited's Answer, Separate Defenses, and Counterclaims to Plaintiff's Complaint. Document filed by Lupin Limited, Case No. 1:12-cv-07910-RJS (Filed: Dec. 20, 2012), 23 pages.
Plaintiff's Reply to Defendant's Counterclaims. Document filed by Gilead Sciences, Inc., Case No. 1:12-cv-07910-RJS (Filed: Jan. 9, 2013), 9 pages.
Order Case No. 1:12-cv-07910-RJS (Dated: Jul. 24, 2013), 1 page.
Complaint for Patent Infringment. Document filed by Gilead Sciences, Inc. Case No. 2:14-cv-00796-JRG-RSP (Filed: Jul. 24, 2014), 14 pages.
Joint Motion for Order on Stipulation for Dismissal. Case No. 2:14-cv-00796-JRG-RSP (Filed: Sep. 16, 2014), 3 pages.
Order on Stipulation for Dismissal. Signed by Magistrate Judge Roy S. Payne on Sep. 23, 2014. (nkl, ) Case No. 2:14-cv-00796-JRG-RSP (Dated: Sep. 23, 2014).
Complaint for Patent Infringment. Document filed by Gilead Sciences, Inc. Case No. 1:12-cv-06351-RJS. (Filed:Aug. 20, 2012), 23 pages.
First Amended Complaint for Patent Infringment.Document filed by Gilead Sciences, Inc., Case No. 1:12-cv-06351-RJS (Filed: Sep. 11, 2012), 47 pages.
Cipla Limited's Answer and Separate Defenses to Plaintiff's First Amended Complaint. Document filed by Cipla Limited, Case No. 1:12-cv-06351-RJS) (Filed: Dec. 10, 2012), 30 pages.
Second Amended Complaint for Patent Infringment. Document filed by Gilead Sciences, Inc., Case No. 1:12-cv-06351-RJS (Filed: Oct. 17, 2013), 24 pages.
Defendant Cipla's Unneccesary Opening Claim Construction Brief. Document filed by Cipla Limited, Case No. 1:12-cv-06351-RJS) (Filed: Oct. 25, 2013), 25 pages.
Declaration of Aaron M. Johnson in Support of Defendant Cipla's Unneccesary Opening Claim Construction Brief. Case No. 1:12-cv-06351-RJS (Filed: Oct. 25, 2013), 3 pages.
Stella, et al., "Prodrugs—Do They Have Advantages in Clinical Practice?" *Drugs*, 29:455-473 (1985).
Exhibit 10 to Declaration of Aaron M. Johnson in Support re: 46 Claim Construction Statement. Document filed by Cipla Limited, Case No. 1:12-cv-06351-RJS (Filed: Oct. 25, 2013), 3 pages.
"prophylaxis" *Steadman's Medical Dictionary* (1995), 3 pages.
Plaintiff's Opening Claim Construction Brief. Document filed by Gilead Sciences, Inc., (Filed: Oct. 25, 2013), 18 pages.

(56) References Cited

OTHER PUBLICATIONS

Declaration of Jason Johnson. Document filed by Gilead Sciences, Inc., Case No. 1:12-cv06351-RJS (Filed: Oct. 25, 2013), 3 pages.
Exhibit A to Declaration of Jason Johnson in Support of Plaintiff's Opening Claim Construction Brief. Document filed by Gilead Sciences, Inc., Case No. 1:12-cv-06351-RJS (Filed: Oct. 25, 2013), 25 pages.
Exhibit B to Declaration of Jason Johnson in Support of Plaintiff's Opening Claim Construction Brief. Document filed by Gilead Sciences, Inc., Case No. 1:12-cv-06351-RJS (Filed: Oct. 25, 2013), 9 pages.
Exhibit C to Declaration of Jason Johnson in Support of Plaintiff's Opening Claim Construction Brief. Document filed by Gilead Sciences, Inc., Case No. 1:12-cv-06351-RJS (Filed: Oct. 25, 2013), 3 pages.
Gilead Scienes, Inc. Q4 2012 Earnings Results Conference call and Webcast presentation (Feb. 4, 2013), 3 pages.
Gilead Scienes, Inc. Q2 2011 Earnings Results Conference call and Webcast presentation (Jul. 26, 2011), 4 pages.
Exhibit G to of Jason Johnson in Support of Plaintiff's Opening Claim Construction Brief. Document filed by Gilead Sciences, Inc., Case No. 1:12-cv-06351-RJS (Filed: Oct. 25, 2013), 2 pages.
Declaration of Amy Patick in Support of Plaintiff's Opening Claim Construction Document filed by Gilead Sciences, Inc.,. Case No. 1:12-cv-06351-RJS (Filed:Oct. 25, 2013), 13 pages.
Exhibit 1 to Declaration of Amy Patick. Document filed by Gilead Sciences, Inc.,. Case No. 1:12-cv-06351-RJS (Filed:Oct. 25, 2013), 15 pages.
Defendant Cipla Limited's Answer and Separate Defenses to Plaintiff's Second Amended Complaint. Case No. 1:12-cv-06351-RJS (Filed: Nov. 1, 2013), 16 pages.
Defendant Cipla's Reply to Plaintiff's Opening Claim Construction Brief. Document filed by Cipla Limited. Case No. 1:12-cv-06351-RJS (Filed: Nov. 22, 2013), 15 pages.
Second Declaration of Aaron M. Johnson in Support of Defendant Cipla's Reply to Plaintiff's Opening Claim Construction Brief. Document filed by Cipla Limited, Case No. 1:12-cv-06351-RJS (Filed: Nov. 22, 2013) , 2 pages.
Honess, R.W. and Watson, D. H.; "Unity and Diversity in the Herpesviruses," *J. Gen. Virol.* (1977), 37:15-37.
Chang, C., et al, "Expression of the precore region of an avian hepatitis B virus is not required for viral replication," *J. Virol.* 1987, 61(10): 3322.
Plantiff's Rebuttal Claim Construction Brief. Document filed by Gilead Sciences, Inc., Case No. 1:12-cv-06351-RJS (Filed: Nov. 22, 2013), 10 pages.
Declaration of Jason Johnson in Support of Plantiff's Rebuttal Claim Construction Brief. Document filed by Gilead Sciences, Inc., (Case No. 1:12-cv-06351-RJS (Filed: Nov. 22, 2013), 2 pages.
Exhibit A to Declaration of Jason Johnson in Support of Plantiff's Rebuttal Claim Construction Brief. Document filed by Gilead Sciences, Inc., Case No. 1:12-cv-06351-RJS (Filed: Nov. 22, 2013), 5 pages.
Letter addressed to Judge Richard J. Sullivan from Christopher P. Borello dated Jul. 28, 2014, Document filed by Gilead Sciences, Inc., Case No. 1:12-cv-06351-RJS (Filed: Jul. 28, 2014), 1 page.
Order on Stipulation for Dismissal Case No. 1:12-cv-06351-RJS—(Dated: Jul. 29, 2014).
Complaint for Patent Infringment. Filed by Gilead Sciences, Inc., Case No. 1:12-CV-06294-RJS (Filed: Aug. 16, 2012), 19 pages.
Lupin Limited's Answer, Separate Defenses, and Counterclaims to Plaintiff's Complaint. Filed by Lupin Limited Case No. 1:12-CV-06294-RJS (Filed: Oct. 22, 2012), 22 pages.
Plaintiff's Reply to Defendant's Counterclaims. Filed by Gilead Sciences, Inc., Case No. 1:12-CV-06294-RJS (Filed: Nov. 9, 2012), 9 pages.
Order: Filed in Associated Cases:1:12-cv-06294-RJS, 1:12-cv-07910-RJS (Dated: Jul. 23, 2013), 1 page.

Stipulation and Agreement Regarding U.S. Pat. Nos. 5,922,695, 5,935,946, 5,977,089 and 6,043,230: 1. (Dated: Aug. 27, 2013), 4 pages.
Order (Dated: May 30, 2014), 1 page.
Order (Dated May 30, 2014), 4 pages.
Complaint for Patent Infringement. Filed by Gilead Sciences, Inc., Emory University, Case No. 1:14-cv-05352-RJS (Filed Jul. 18, 2014), 12 pages.
Lupin Limited's Answer, Separate Defenses, and Counterclaims to Plaintiff's Complaint. Filed by Lupin Limited.For Case No. 1:14-cv-05352-RJS (Dated: Aug. 22, 2014), 16 pages.
Letter addressed to Judge Richard J. Sullivan from David B. Bassett dated Sep. 16, 2014. Document filed by Emory University, Gilead Sciences, Inc.,Case No. 1:14-cv-05352-RJS (Filed Sep. 16, 2014), 1 page.
Order on Stipulation for Dismissal: Case No. 1:12-cv-06293-RJS (Dated: Sep. 16, 2014), 2 pages.
Complaint for Patent Infringement. Filed by Emory University, Gilead Sciences, Inc., Case No. 1:14-cv-03928-RJS (Filed: Jun. 2, 2014), 18 pages.
Letter addressed to Judge Richard J. Sullivan from Colleen Tracy dated Jun. 27, 2014. Document filed by Emory University, Gilead Sciences, Inc., Case No. 1:14-cv-03928-RJS (Filed: Jun. 27, 2014), 2 pages.
Notice of Voluntary Dismissal Pursuant to F.R.C.P. 41(a)(1)(a)(i) Case No. 1:14-cv-03928-RJS (Dated: Jun. 27, 2014), 1 page.
Complaint for Patent Infringement. Filed by Emory University, Gilead Sciences, Inc., Case No. 1:12-CV-06350 (Filed: Aug. 20, 2012), 14 pages.
Cipla Limited's Answer and Separate Defences to Plaitiffs' Complaint. Filed by Cipla Limited, Case No. 1:12-CV-06350-RJS (Filed: Dec. 10, 2012), 10 pages.
Letter addressed to Judge Richard J. Sullivan from Christopher P. Borello dated Jul. 28, 2014. Document filed by Emory University, Gilead Sciences, Inc., 1:12-cv-06350-RJS (Dated: Jul. 28, 2014), 1 page.
Order on Stipulation for Dismissal. Case No. 1:12-cv-06350-RJS (Dated: Jul. 29, 2014), 2 pages.
Complaint for Patent Infringement. Filed by Gilead Sciences, Inc. and Emory University, Case No. 1:14-cv-00099-IMK (Filed: Jun. 10, 2014), 19-pages.
Appendix 1 to Complaint Filed by Gilead Sciences, Inc. and Emory University, Case No. 1:14-cv-00099-IMK (Filed: Jun. 10, 2014), 19 pages.
Amended Complaint for Patent Infringement. Filed by Gilead Sciences, Inc. and Emory University, Case No. 1:14-cv-00099-IMK (Filed: Jun. 27, 2014), 18 pages.
Answer, Defenses, and Counterclaims of Mylan Pharmaceuticals Inc and Mylan Inc., Filed by Mylan Inc., Mylan Pharmaceuticals Inc., Case No. 1:14-cv-00099-IMK (Filed Aug. 12, 2014), 36 pages.
Plaintiff's Answer to Defendants' Counterclaims. Filed by Gilead Sciences, Inc. and Emory University, Case No. 1:14-cv-00099-IMK (Filed: Sep. 2, 2014), 10 pages.
Amended Answer, Defenses, and Counterclaims of Mylan Pharmaceuticals Inc and Mylan Inc., Filed by Mylan Inc., Mylan Pharmaceuticals Inc., Case No. 1:14-cv-00099-IMK (Filed: Sep. 2, 2014), 36 pages.
Stipulation Concerning Defendants Amended Answer, Defenses and Counterclaims, Case No. 1:14-cv-00099-IMK (Filed: Oct. 2, 2014), 2 pages.
Stipulation Regarding Mylan Inc., Filed by Mylan Inc., Case No. 1:14-cv-00099-IMK (Filed: Dec. 15, 2014), 3 pages.
Second Amended Complaint for Patent Infringement, Filed by Gilead Sciences, Inc. and Emory University,Case No. 1:14-cv-00099-IMK (Filed: Jan. 21, 2015), 21 pages.
Answer, Defenses, and Counterclaims of Mylan Pharmaceuticals Inc and Mylan Inc. To Plaintiffs' Second Amended Complaint, Filed by Mylan Inc., Mylan Pharmaceuticals Inc., Case No. 1:14-cv-00099-IMK (Filed: Feb. 9, 2015), 51 pages.
Joint Stipulation Regarding Claim Construction. Case No. 1:14-cv-00099-IMK (Filed: Feb. 19, 2015), 4 pages.

(56) References Cited

OTHER PUBLICATIONS

Gilead's Opening Brief in Support of Its Proposed Claim Constructions for U.S. Pat. Nos. 8,592,397 and 8,716,264. Case No. 1:14-cv-00099-IMK (Filed: Feb. 19, 2015), 27 pages.
Declaration of David B. Bassett in Support of Gilead's Opening Brief in Support of Its Proposed Claim Construction. Case No. 1:14-cv-00099-IMK (Filed: Feb. 19, 2015), 134 pages.
Declaration of Patrick J. Sinko, Ph.D., R.Ph., in Support of Gilead's Opening Brief in Support of Its Proposed Claim Construction. Case No. 1:14-cv-00099-IMK (Filed: Feb. 19, 2015), 171 pages.
Declaration of Carlo-Federico Perno, M.D. Ph.D. in Support of Gilead's Claim Construction., Case No. 1:14-cv-00099-IMK (Filed: Feb. 19, 2015), 14 pages.
Exhibit 1 Declaration of Carlo-Federico Perno, M.D. Ph.D. in Support of Gilead's Claim Construction. Case No. 1:14-cv-00099-IMK (Filed: Feb. 19, 2015), 42 pages.
Exhibit 2 Declaration of Carlo-Federico Perno, M.D. Ph.D. in Support of Gilead's Claim Construction.Case No. 1:14-cv-00099-IMK (Filed: Feb. 19, 2015), 2 pages.
Exhibit 3 Declaration of Carlo-Federico Perno, M.D. Ph.D. in Support of Gilead's Claim Construction. Case No. 1:14-cv-00099-IMK (Filed: Feb. 19, 2015), 3 pages.
Muma, R. D., et al, "Zidovudine adherence among individuals with HIV infection." *AIDS Care.* 1995;7(4):439-47.
Richman, D.D., "Antiretroviral drug resistance: mechanisms, pathogenesis, clinical significance." *Antiviral Chemotherapy* 4, 383-395 J. Mills, Ed., Plenum Press, New York, 1996.
Johnson, V., "Combination therapy for HIV-1 infection-overview: preclinical and clinical analysis of antiretroviral combinations" *Antiviral Research* 29 (1996) 35-39.
Akanbi, M.O., et al, "Combination nucleoside/nucleotide reverse transcriptase inhibitors for treatment of HIV infection" *Expert Opin Pharmacother.* Jan. 2012;13(1):65-79.
De Clercq, E., "Anti-HIV drugs: 25 compounds approved within 25 years after the discovery of HIV" *Int J Antimicrob Agents.* Apr. 2009;33(4):307-20.
Heffernan, J.M. and Wahl, L. M., "Natural variation in HIV infection: Monte Carlo estimates that include CD8 effector cells" *Journal of Theoretical Biology* 243 (2006) 191-204.
Ho, D. D., "Viral Counts Count in HIV Infection" vol. 272, 1124-1125, May 24, 1996.
Mellors, J. W., et al, "Prognosis in HIV-1 Infection Predicted by the Quantity of Virus in Plasma" *Science*,vol. 272, 1167-1170, May 24, 1996.
Plaintiffs' Motion to Strike Mylan's Third Separate Defense. Document filed by Gilead Sciences, Inc. and Emory University, Case No. 1:14-cv-00099-IMK (Filed: Mar. 2, 2015), 3 pages.
Declaration of David Bassett in Support of Plaintiffs' Motion to Strike Mylan's Third Separate Defense. Document filed by Gilead Sciences, Inc. and Emory University, Case No. 1:14-cv-00099-IMK (Filed: Mar. 2, 2015), 12 pages.
Memorandum in Support of Plaintiffs' Motion to Strike Mylan's Third Separate Defense. Document filed by Gilead Sciences, Inc. and Emory University, Case No. 1:14-cv-00099-IMK (Filed: Mar. 2, 2015), 15 pages.
Plaintiffs' Answer to Defentant Mylan Pharmaceuticals Inc.'s Amended Counter Claims. Document filed by Gilead Sciences, Inc. and Emory University, Case No. 1:14-cv-00099-IMK (Filed: Mar. 2, 2015), 12 pages.
Defendants Mylan Inc. and Mylan Pharmaceuticals Inc.'s Answering Claim Construction Brief in Support of Their Proposed Claim Constructions for U.S. Pat. Nos. 8,592,397 and 8,716,264. Document filed by Mylan Inc., Mylan Pharmaceuticals Inc., Case No. 1:14-cv-00099-IMK (Filed: Mar. 12, 2015), 28 pags.
Declaration of Karen M. Cassidy in Support of Defendants Mylan Inc. and Mylan Pharmaceuticals Inc.'s Answering Claim Construction Brief in Support of Their Proposed Claim Constructions for U.S. Pat. Nos. 8,592,397 and 8,716,264. Document filed by Mylan Inc., Mylan Pharmaceuticals Inc., Case No. 1:14-cv-00099-IMK (Filed: Mar. 12, 2015), 199 pages.

Declaration of Choloe Lynne Thio, M.D. in Support of Defendants Mylan Inc. and Mylan Pharmaceuticals Inc.'s Answering Claim Construction Brief in Support of Their Proposed Claim Constructions for U.S. Pat. Nos. 8,592,397 and 8,716,264. Document filed by Mylan Inc., Mylan Pharmaceuticals Inc., Case No. 1:14-cv-00099-IMK (Filed: Mar. 12, 2015), 184 pages.
Declaration of Frank Chrzanowsiu, Ph.D. in Support of Defendants Mylan Inc. and Mylan Pharmaceuticals Inc.'s Answering Claim Construction Brief in Support of Their Proposed Claim Constructions for U.S. Pat. Nos. 8,592,397 and 8,716,264. Document filed by Mylan Inc., Mylan Pharmaceuticals Inc., Case No. 1:14-cv-00099-IMK (Filed: Mar. 12, 2015), 32 pages.
Gilead's Motion to Defer Consideration of Mylan's Indefiniteness Argument or, Alternatively, for Leave to File a Reply. Case No. 1:14-cv-00099-IMK (Filed: Mar. 19, 2015), 8 pages.
Declaration of David B. Bassett in Support of Gilead's Motion to Defer Consideration of Mylan's Indefiniteness Argument or, Alternatively, for Leave to File a Reply., Case No. 1:14-cv-00099-IMK (Filed: Mar. 19, 2015), 30 pages.
Mylan Inc.'s and Mylan Pharmaceuticals Inc.'s Response to Plaintiffs' Motion to Strike, Case No. 1:14-cv-00099-IMK (Filed: Mar. 19, 2015), 3 pages.
Motion Requesting Expedited Briefing for Gilead's Motion to Defer Consideration of Mylan's Indefiniteness Argument or, Alternatively, for Leave to File a Reply., Case No. 1:14-cv-00099-IMK (Filed: Mar. 19, 2015), 3 pages.
Defendants Mylan Inc. and Mylan Pharmaceuticals Inc.'s Response to Gilead's Motion to Defer Consideration of Mylan's Indefiniteness Argument or, Alternatively, for Leave to File a Reply. Case No. 1:14-cv-00099-IMK (Filed: Mar. 26, 2015), 9 pages.
Declaration of William O. Adams in Support of Defendants Mylan Inc. and Mylan Pharmaceuticals Inc.'s Response to Gilead's Motion to Defer Consideration of Mylan's Indefiniteness Argument or, Alternatively, for Leave to File a Reply. Document filed by Mylan Inc., Mylan Pharmaceuticals Inc., Case No. 1:14-cv-00099-IMK (Filed: Mar. 26, 2015), 20 pages.
Reply Memorandum in Support of Gilead's Motion to Defer Consideration of Mylan's Indefiniteness Argument. Document filed by Emory University and Gilead Sciences, Inc., Case No. 1:14-cv-00099-IMK (Filed: Mar. 30, 2015), 6 pages.
Joint Stipulation Regarding Claim Construction. Signed by District Judge Irene M. Keeley on Mar. 31, 2015. (jss), Case No. 1:14-cv-00099-IMK (Filed: Mar. 31, 2015), 4 pages.
Notice of Opposition filed by Alphaphann Pty Ltd in the Australian Patent Office for Application No. 2011253996, dated Nov. 28, 2014, 1 page.
Coffin JM, Hughes SH, Varmus HE, editors, "Retroviruses," Cold Spring Harbor (NY) : Cold Spring Harbor Laboratory Press 1997.
White et al., "Molecular Mechanisms of Resistance to Human Immunodeficiency Virus Type 1 with Reverse Transcriptase Mutations K65R and K65R M184V and Their Effects on Enzyme Function and Viral Replication Capacity," Antimicrobial Agents and Chemotherapy, Nov. 2002, p. 2437-3446.
Viread insert, 2001, DNA 21-356, 20 pages.
Epivir Approval Package Mar. 23 ,1999, 22 pages.
Whitney, "The M184V Mutation in Reverse Transcriptase Can Delay Reversion of Attenuated Variants of Simian Immunodeficiency Virus," Journal of Vrology vol. 76 (17) p. 8958-8962.
Retrovir Product Information (2001), 23 pages.
Jemesk, Poor Virologic Responses and Early Emergence of Resistance in Treatment Naive, HIV-infected Patients Receiving a Once Daily Triple Nucleoside Regimen of Didanosine, Lamivudine, and Tenefoir DF, Program Abstr. Conf, Ertrovir, Oppor Infect 11th 2004 San Francisco Calf, Feb. 8-11, 2004. Abstract 51.
Farthing, "Early Virologic Failure in a Pilot Study Evaluating the Efficacy of Abacavir, Lamivudine and Tenofovir in the Treatment Naive HIV-Infected Patients," The 2nd IAS Conference on HIV Pathogenesis and Treatment Abstract No. 43, Jul. 2003.
Kagan, "Increasing prevalence of HIV-1 reverse transcriptase mutation K65R correlates with tenofovir utilization," 2004, AntiViral Therapy vol. 9 pp. 827-828.

(56) References Cited

OTHER PUBLICATIONS

Fisher, "The safety and efficacy of adefovir dipivoxil in patients with advanced HIV disease: a randomized, placebocontrolled trial," Aids vol. 15 p. 1695-1700.
Cihiar, "Human Renal Organic Anion Transporter 1 (Hoat1) and Its Role in the Nephrotoxicity of Antiviral Nucleotide Analogs," Nucleosides ,Nucleotides & nucleic Acids, 2001 vol. 20(4-7) p. 641-648.
Charpentier, "Evolution of the K65R, K103N and M184V/I reverse transcriptase mutations prevalence in HIV-1 infected patients experiencing virologic failure between 2005 and 2010," Abstract CROI 2012.
Grant and Hackh's "Chemical Dictionary" 5th ed. R. Grant (editors) 1987, 7 pages.
Foye's Principles of Medicinal Chemistry 5th ed. 2002, 4 pages.
Center for drug evaluation and research 21-356 Chemistry Review (Viread)—12 pages.
Thoithi et. al, "Investigation of the kinetics of degradation of hexopyranosylated cytosine nucleosides using liquid chromatography" Nucleosides ,Nucleotides & Nucleic Acids (2003).
Calculating the pH of an aquesou solution of TDF, 1 page.
Handbook of Pharmaceutical Excipients, Fourth Edition, edited by Rowe, Sheskey, and Weller, "Lactose and Water," 17 pages (Nov. 2002).
Kashuba, "Antiretroviral-Drug Concentrations in Semen: Implications for Sexual Transmission of Human Immunodeficiency Virus Type 1," Antimicrobial Agents and Chemotherapy 43(8):1817-1826 (1999).
The Emtriva Label, 19 pages.
Chemistry Reviews for NDA 21-752 Truvada, 27 pages.
Clinical pharmacology section of the ANCOBON, 6 pages (Mar. 2003).
Proloprim, 3 pages.
ICH Stability Testing of New Drug Substances and Products 2003, 98 pages.
Reynolds et al. "Available Guidance and Best Practices for Conducting Forced Degradation Studies" Pharm Technol 2002, 9 pages.
Carstensen, J.T., *Advanced Pharmaceutical Solids*, 2001, p. 273, 3 pages.
Novak, "Prevalence of Antiretroviral Drug Resistance Mutations in Chronically HIV-Infected, Treatment-Naïve Patients: Implications for Routine Resistance Screening before Initiation of Antiretroviral Therapy," Clin. Infect Dis. Feb. 1, 2005;40(3) 486-74.
Grant et al., "Preexposure Chemoprophylaxis for HIV Prevention in Men Who Have Sex with Men," New England Journal of Medicine 363:27, 2587 (2010).
Time Magazine, Dec. 9, 2010, "AIDS Drugs Lower the Risk of HIV Infection," by Alice Park.
EMEA (European Medicine Agency) Scientific Discussion on Truvada, 2005, 28 pages.
EMEA (European Medicine Agency) Scientific Discussion on Emtriva, 2005,—30 pages.
Pischetsrieder, "Formation of an Aminoreductone during the Maillard Reaction of Lactose with Nr-Acetyllysine or Proteins," J. Agric. Food Chem. 1998, 46, 928-931.
Bharate, "Interactions and incompatibilities of pharmaceutical excipients with active pharmaceutical ingredients: a comprehensive review" J. Excipients and Food Chem. 1 (3) (2010).
Expert Opinion Prof. Richard M. Novak relating to opposition proceedings being conducted in Israel against Gilead Sciences, Inc. ("The Applicant"), concerning Israel patent application No. IL 169243, Sep. 22, 2012, 40 pages.
Second Expert Opinion Prof. Richard M.Novak relating to opposition proceedings being conducted in Israel against Gilead Sciences, Inc. ("The Applicant"), concerning Israel patent application No. IL 169243, Apr. 9, 2014, 50 pages.
Expert Opinion Prof. Joseph Marian Fortunak relating to opposition proceedings being conducted in Israel against Gilead Sciences, Inc. ("The Applicant"), concerning Israel patent application No. IL 169243, Sep. 20, 2012, 30 pages.
Expert Opinion of Dr. G. Patrick Stahly filed in the Israeli Patent Office in opposition proceedings initiated by Teva Pharmaceutical Industries Ltd. against Israeli Patent Application No. 169,243, filed by GileadSciences Inc., 27 pages.
Truvada Summary of Product Characteristics, 35 pages.
Shapiro and Klein "The Deamination of Cytidine and Cytosine by Acidic Buffer Solutions. Mutagenic Implications," *Biochemistry*, vol. 5, No. 7, Jul. 1966, 2358.
Notari, "A Mechanism for the Hydrolytic Deamination of Cytosine Arabinoside in Aqueous Buffer," *Journal of Pharmaceutical Science*, vol. 56, No. 7, Jul. 1967, 804.
Notari, "intermolecular and Intramolecular Catalysis in Deamination of Cytosine Nucleosides," *Journal of Pharmaceutical Science*, vol. 59, No. 1, Jan. 1970, 28.
Lonnberg, "Competition between the hydrolysis and deandntion of cytidine and its 5-substituted deirivatives in aqueous acid," *Nucleic Acid Research*, vol. 13, Nov. 1985, 2451.
Dong, "Modeling of Autocatalytic Hydrolysis of Adefovir Dipivoxil in Solid Formulations," *Journal of the Pharmaceutical Society of Japan*, 131(4), 643.
Wong, "Major Degradation Product Identified in Several Pharmaceutical Formulkions against the Common Cold," *Anal. Chem.*, 2006, 78, 7891.
Aulton, *Pharmaceutics the Science of Dosage Form Design* (1988), 618.
Augsburger, "Tablet Formulation," *Encyclopedia of Pharmaceutical Technology* ($3^{rd}$. ed.), 3646, 13 pages (2007).
Armstrong, "Tablet Manufacture by Direct Compression," Encyclopedia of Pharmaceutical Technology (3rd. ed.), 3673-3683 (2007).
Chan, "Excipients: Powders and Solid Dosage Forms," Encyclopedia of Pharmaceutical Technology (3rd. ed.), 1646-1655 (2007).
Airaksinen, "Role of Water in the Physical Stability of Solid Dosage Formulations," *Journal of Pharmaceutical Sciences*, vol. 94, No. 10, 19 pages.
Ahlneck and Zografi, "The molecular basis of moisture effects on the physical and chemical stability of drugs in the solid state," *International Journal of Pharmaceutics*, 62 (1990) 87-95.
Kaupp, "Solid-state reactions, dynamics in molecular crystals," *Current Opinion in Solid State & Material Science*, 6 (2002) 131-138.
Byrn, "Chemical reactivity in solid-state pharmaceuticals: formulation implications," *Advanced Drug Deliveries Reviews* 48 (2001), 115-136.
Li, "The Solid State Michael Addition of Indole to 4-Arylidene-3-methyl-5 pyrazolone," 6*J. Heterocyclic. Chem.*, 36, 697 (1999).
Frantz, "The trouble with making combination drugs,"News & Analysis section of *Nature Review Drug Discovery*, vol. 5, 881, 2 pages.
Summary of Preformulation Report for GS-4331 fumarate salt,1 page, Mar. 4, 1997.
Flemming, "Compaction of lactose drug mixtures: Quantification of the extent of incompatibility by FT-Raman spectroscopy," *European Journal of Pharmaceutics and Biopharmaceutics* 68, 802-810.
Desai, "Preformulation Compatibility Studies of tamsylate and Fluconazole Drugs with Lactose by DSC," *Journal of Thermal Analysis*, vol. 71, 651-658.
Gokhale, "Glycosylation of Aromatic Amines I: Characterization of Reaction Products and Kinetic Scheme," *AAPS PharmaSciTech*, vol. 10, No. 2, 317.
Gallo, "Frequent Detection and Isolation of Cytopathic Retroviruses (HTL V-III) from Patients with AIDS and at Risk for AIDS," *Science, New Series*, vol. 224, No. 4648 (May 4, 1984), 500-503.
Expert Opinion of Prof. Robert R. Redfield in opposition proceedings initiated by Teva Pharmaceutical Industries Ltd. against Israeli Patent Application No. 169,243, filed by Gilead Sciences Inc., 38 pages.
Redfield, "Frequent Transmission of HTLV-III Among Spouses of Patients with AIDS-Related Complex and AIDS", JAMA 1985; 253(11):1571-1573.
Redfield, "The Walter Reed Staging Classification for HTLV III, LAV Infection", *New England Journal of Medicine* 1986; 314: 131-132.

(56) References Cited

OTHER PUBLICATIONS

Baeten, "Antiretroviral Prophylaxis for HIV Prevention in Heterosexual Men and Women," New England Journal of Medicine 367:5, 399 (2012).

Thigpen, "Antiretroviral Preexposure Prophylaxis for Heterosexual HIV Transmission in Botsw," New England Journal of Medicine 367:5, 423 (2012).

Highlights of Prescribing Information for Truvada, 45 pages, Jul. 2012.

Grossman, et al., "Drug-Resistant HIV Infection among Drug-Naïve Patients in Israel," Journal of Clinical Infectious Disease 40, 294 (2005).

Bazmi, "In Vitro Selection of Mutations in the Human Immunodeficiency Virus Type 1 Reverse Transcriptase That Decrease Susceptibility to (2)-b-D-Dioxolane-Guanosine and Suppress Resistance to 39-Azido-39-Deoxythymidine," Antimicrobial Agents and Chemotherapy, 44, 1783 (2000).

Roge, "Genotypic and phenotypic changes in antiretroviral-naive patients experiencing failure on randomised treatment with abacavir, didanosine and stavudine," Antiviral Therapy, 7, S125 (2002).

Dart Virology Group and Trial Team "Virological response to a triple nucleoside/nucleotide analogue regimen over 48 weeks in HIV-1-infected adults in Africa," AIDS 20(10), 1391-1399 (2006).

Rey, "Virologic Response of Zidovudine, Lamivudine, and Tenofovir Disoproxil Fumarate Combination in Antiretroviral-Naive HIV-1-Infected Patients," *J. AIDS* 43(5), 530 (2006).

Kirkland, "Response to Lamivudine-Zidovudine plus Abacavir Twice Daily in Antiretroviral-Naive, Incarcerated Patients with HIV Infection Taking Directly Observed Treatment," Clinical Infectious Diseases, 34, 511 (2002).

Little, "Antiretroviral-Drug Resistance Among Patients Recently Infected With HIV," New England Journal of Medicine, 347(6), 385 (2002).

Rubio,"Increase in the frequency of mutation at codon 215 associated with zidovudine resistance in HIV-1-infected antiviral-naive patients from 1989 to 1996," AIDS, 11(9), 1184 (1997).

Winston, "The prevalence and determinants of the K65R mutation in HIV-1 reverse transcriptase in tenofovir-naive patients," AIDS, 16(15), 2087, Oct. 18, 2002.

Pillay, "HIV Type 1 Subtype C Drug Resistance among Pediatric and Adult South African Patients Failing Antiretroviral Therapy," AIDS Research Human Retroviruses, 24, 1449 (2008).

Loemba, "Genetic Divergence of Human Immunodeficiency Virus Type 1 Ethiopian Clade C Reverse Transcriptase (RT) and Rapid Development of Resistance agains," *Antimicrobial Agents and Chemotherapy*, 46(7), 2087, Jul. 2002.

Lambert, "Prevalence of pre-existing resistance-associated mutations to rilpivirine, emtricitabine and tenofovir in antiretroviral-naiv," *Journal of Antimicrobial Chemotherapy*, Jan. 29, 2013.

Anion, "The K65R Mutation Confers Increased DNA Polymerase Processivity to HIV-1 Reverse Transcriptase ," *J. Biological Chemistry*, 37, 15908, Aug. 16, 1996.

Miller, "Human Immunodeficiency Virus Type 1 Reverse Transcriptase Expressing the K7OE Mutation Exhibits a Decrease in Specific Activity and Processivity," Molecular Pharmacology, 54, 291 (1998).

The FDA's press release dated Jul. 2, 2002 reporting the new approved dosing for Epivir (3TC), titled "New Dosing approved for Epivir (lamivudine)," 1 page.

Raune,Pharmacodynamic effects of zidovudine 600 mg once daily versus zidovudine 300 mg twice daily in therapy-naïve HIVinfected patients (COD20002), Late Breaker Poster Exhibition: *The XIV International AIDS Conference* (2002), 1 page.

FDA Press Release Zerit XR, Dec. 31, 2002, titled "Approval of ZERIT® XR, a new formulation that allows once-a-day dosing Dec. 31," 1 page.

FDA Videx EC Approval Letter dated Oct. 31, 2000, 3 pages.

Callendar, "Pharmacokinetics of Oral Zidovudine Entrapped in Biodegradable Nanospheres in Rabbits," *Antimicrobial Agents and Chemotherapy* 43(4), 972, Apr. 1999.

Cohen, 45th *Interscience Conference on Antimicrobial Agents and Chemotherapy* Poster H-521, 1 page.

Elion, "Once-Daily Abacavir/Lamivudine/Zidovudine plus Tenofovir for the Treatment of HIV-1 Infection in Antiretroviral-Naive Subjects: A 48-Week Pilot Study," *HIV Clinical Trials*, 7(6), 324, 2006.

Meier, "Cidofovir-induced End-Stage Renal Failure,"Nephrology Dialysis Transplantation, 17, 148 (2002).

Verhelst, "Fanconi Syndrome and Renal Failure Induced by Tenofovir: A First Case Report," American Journal of Kidney Diseases, 40(6), 1331, Dec. 2002.

Coca, "Rapid Communication: Acute Renal Failure Associated with Tenofovir: Evidence of Drug-Induced Nephrotoxicity," American Journal of Medical Science 324(6), 342 Dec. 2002.

Bowonwatanuwong, "A Randomised, Open Label Study to Investigate Abacavir ( Abc) and Lamivudine (3TC) As Once Daily (QD) Components of a Triple Combination Regimen (EPV40001).," 1st IAS Conference, Buenos Aires, Argentina, Jul. 8-11 2001, 1 page.

Statement in Response by Applicant in opposition proceedings initiated by Teva Pharmaceutical Industries Ltd. against Israeli Patent Application No. 169,243, filed by Gilead Sciences Inc., 27 pages.

Memorandum Opinion and Order Granting Plaintiffs' Motion to Defer Consideration of Mylan's Indefiniteness Argument, CV No. 1:14CV99, signed Apr. 6, 2015.

Statement concerning Request for Intervention for Case No. 3k:26-27, Istanbul Patent No. TR 2008/067, dated Apr. 13, 2015, 25 pages.

İlko İlaç San. ve Tic. A.Ş.'s Invalidation Petition for Turkish Patent No. 2008/06970 filed Sep. 10, 2014.

Gilead Sciences, Inc.'s Response to İlko İlaç San. ye Tic. A.Ş.'s Invalidation Petition for Turkish Patent No. 2008/06970 filed Dec. 31, 2014.

İlko İlaç San. ye Tic. A.Ş.'s Second Invalidation Petition for Turkish Patent No. 2008/06970 field Feb. 26, 2015 (Translation).

* cited by examiner

COMPOSITIONS AND METHODS FOR COMBINATION ANTIVIRAL THERAPY

This application is a Continuation of U.S. application Ser. No. 14/227,653 filed Mar. 27, 2014, which is a continuation of U.S. patent application Ser. No. 12/204,174 now U.S. Pat. No. 8,716,264, filed Sep. 4, 2008, which is a continuation of U.S. patent application Ser. No. 10/540,794, filed Mar. 20, 2006, which is a national stage entry of PCT/US04/00832, filed Jan. 13, 2004 which claims the benefit of Provisional Application Nos. 60/440,246 and 60/440,308, both filed Jan. 14, 2003, the disclosures of each of which is incorporated herein by reference in its entirety.

FIELD OF THE INVENTION

The invention relates generally to combinations of compounds with antiviral activity and more specifically with anti-HIV properties. In particular, it relates to chemically stable combinations of structurally diverse anti-viral agents.

BACKGROUND OF THE INVENTION

Human immunodeficiency virus (HIV) infection and related diseases are a major public health problem worldwide. Human immunodeficiency virus type 1 (HIV-1) encodes at least three enzymes which are required for viral replication: reverse transcriptase (RT), protease (Prt), and integrase (Int). Although drugs targeting reverse transcriptase and protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001). Human immunodeficiency virus type 1 (HIV-1) protease (Prt) is essential for viral replication and is an effective target for approved antiviral drugs. The HIV Prt cleaves the viral Gag and Gag-Pol polyproteins to produce viral structural proteins (p17, p24, p7 and p6) and the three viral enzymes. Combination therapy with RT inhibitors has proven to be highly effective in suppressing viral replication to unquantifiable levels for a sustained period of time. Also, combination therapy with RT and Prt inhibitors (PI) have shown synergistic effects in suppressing HIV replication. Unfortunately, a high percentage, typically 30 to 50% of patients currently fail combination therapy due to the development of drug resistance, non-compliance with complicated dosing regimens, pharmacokinetic interactions, toxicity, and lack of potency. Therefore, there is a need for new HIV-1 inhibitors that are active against mutant HIV strains, have distinct resistance profiles, fewer side effects, less complicated dosing schedules, and are orally active. In particular, there is a need for a less onerous dosage regimen, such as once per day oral dosing, optimally with as few pills as possible.

The use of combinations of compounds can yield an equivalent antiviral effect with reduced toxicity, or an increase in drug efficacy. Lower overall drug doses can reduce the frequency of occurrence of drug-resistant variants of HIV. Many different methods have been used to examine the effects of combinations of compounds acting together in different assay systems (Furman WO 02/068058). Lower doses predict better patient compliance when pill burden decreases, dosing schedules are simplified and, optionally, if synergy between compounds occurs (Loveday, C. "Nucleoside reverse transcriptase inhibitor resistance" (2001) *JAIDS Journal of Acquired Immune Deficiency Syndromes* 26:S10—S24). AZT (Zidovudine™, 3'-azido, 3'-deoxythymidine) demonstrates synergistic antiviral activity in vitro in combination with agents that act at HIV-1 replicative steps other than reverse transcription, including recombinant soluble CD4 castanospermine and recombinant interferon-α. However, it must be noted that combinations of compounds can give rise to increased cytotoxicity. For example, AZT and recombinant interferon-α have an increased cytotoxic effect on normal human bone marrow progenitor cells.

Chemical stability of combinations of antiviral agents is an important aspect of co-formulation success and the present invention provides examples of such combinations.

There is a need for new combinations of orally-active drugs for the treatment of patients infected with certain viruses, e.g. HIV, that provide enhanced therapeutic safety and efficacy, impart lower resistance, and predict higher patient compliance.

SUMMARY OF THE INVENTION

The present invention provides combinations of antiviral compounds, in particular compositions and methods for inhibition of HIV. In an exemplary aspect, the invention includes a composition including tenofovir disoproxil fumarate and emtricitabine which has anti-HIV activity. The composition of tenofovir DF and emtricitabine is both chemically stable and either synergistic and/or reduces the side effects of one or both of tenofovir DF and emtricitabine. Increased patient compliance is likely in view of the lower pill burden and simplified dosing schedule.

The present invention relates to therapeutic combinations of [2-(6-amino-purin-9-yl)-1-methyl-ethoxymethyl]-phosphonic acid diisopropoxycarbonyloxymethyl ester fumarate (tenofovir disoproxil fumarate, tenofovir DF, TDF, Viread®) and (2R,5S,cis)-4-amino-5-fluoro-1-(2-hydroxymethyl-1,3-oxathiolan-5-yl)-(1H)-pyrimidin-2-one (emtricitabine, Emtriva™, (−)-cis FTC) and their use in the treatment of HIV infections including infections with HIV mutants bearing resistance to nucleoside and/or non-nucleoside inhibitors. The present invention is also concerned with pharmaceutical compositions and formulations of said combinations of tenofovir disoproxil fumarate and emtricitabine. Another aspect of the invention is a pharmaceutical formulation comprising a physiologically functional derivative of tenofovir disoproxil fumarate or a physiologically functional derivative of emtricitabine.

Therapeutic combinations and pharmaceutical compositions and formulations of the invention include the combination of PMEA or PMPA (tenofovir) compounds with emtricitabine or (2R,5S,cis)-4-amino-1-(2-hydroxymethyl-1,3-oxathiolan-5-yl)-(1H)-pyrimidin-2-one (3TC, lamivudine, Epivir™), and their use in the treatment of HIV infections.

One aspect of the invention is a method for the treatment or prevention of the symptoms or effects of an HIV infection in an infected animal which comprises administering to, i.e. treating, said animal with a therapeutically effective amount of a combination comprising [2-(6-amino-purin-9-yl)-1-methyl-ethoxymethyl]-phosphonic acid diisopropoxycarbonyloxymethyl ester fumarate (tenofovir DF, TDF) or a physiologically functional derivative thereof, and (2R,5S,cis)-4-amino-5-fluoro-1-(2-hydroxymethyl-1,3-oxathiolan-5-yl)-(1H)-pyrimidin-2-one (emtricitabine) or a physiologically functional derivative thereof.

Another aspect of the invention is a unit dosage form of a therapeutic combination comprising tenofovir disoproxil fumarate and emtricitabine, or physiological functional derivatives thereof. The unit dosage form may be formulated for administration by oral or other routes and is unexpectedly chemically stable in view of the properties of the structurally diverse components.

Another aspect of the invention is directed to chemically stable combination antiviral compositions comprising tenofovir disoproxil fumarate and emtricitabine. In a further aspect of the invention, the chemically stable combinations of tenofovir disoproxil fumarate and emtricitabine further comprise a third antiviral agent. In this three-component mixture, the unique chemical stability of tenofovir disoproxil fumarate and emtricitabine is taken advantage of in order to enable the combination with the third antiviral agent. Particularly useful third agents include, by way of example and not limitation, those of Table A. Preferably, the third component is an agent approved for antiviral use in humans, more preferably, it is an NNRTI or a protease inhibitor (PI), more preferably yet, it is an NNRTI. In a particularly preferred embodiment, the invention is directed to a combination of the chemically stable mixture of tenofovir disoproxil fumarate and emtricitabine together with efavirenz.

Another aspect of the invention is a patient pack comprising at least one, typically two, and optionally, three active ingredients and other antiviral agents selected from tenofovir disoproxil fumarate and emtricitabine, and an information insert containing directions on the use of tenofovir disoproxil fumarate and emtricitabine together in combination.

Another aspect of the invention is a process for preparing the combinations hereinbefore described, which comprises bringing into association tenofovir DF and emtricitabine of the combination in a medicament to provide an antiviral effect. In a further aspect of the present invention, there is provided the use of a combination of the present invention in the manufacture of a medicament for the treatment of any of the aforementioned viral infections or conditions.

DETAILED DESCRIPTION OF THE INVENTION

While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

When tradenames are used herein, applicants intend to independently include the tradename product and the active pharmaceutical ingredient(s) of the tradename product.

The term "chemical stability" means that the two primary antiviral agents in combination are substantially stable to chemical degradation. Preferably, they are sufficiently stable in physical combination to permit commercially useful shelf life of the combination product. Typically, "chemically stable" means that a first component of the mixture does not act to degrade a second component when the two are brought into physical combination to form a pharmaceutical dosage form. More typically, "chemically stable" means that the acidity of a first component does not catalyzes or otherwise accelerate the acid decomposition of a second component. By way of example and not limitation, in one aspect of the invention, "chemically stable" means that tenofovir disoproxil fumarate is not substantially degraded by the acidity of emtricitabine. "Substantially" in this context means at least about less than 10%, preferably less than 1%, more preferably less than 0.1%, more preferably yet, less than 0.01% acid degradation of tenofovir disoproxil fumarate over a 24-hour period when the products are in a pharmaceutical dosage form.

The terms "synergy" and "synergistic" mean that the effect achieved with the compounds used together is greater than the sum of the effects that results from using the compounds separately, i.e. greater than what would be predicted based on the two active ingredients administered separately. A synergistic effect may be attained when the compounds are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic antiviral effect denotes an antiviral effect which is greater than the predicted purely additive effects of the individual compounds of the combination.

The term "physiologically functional derivative" means a pharmaceutically active compound with equivalent or near equivalent physiological functionality to tenofovir DF or emtricitabine when administered in combination with another pharmaceutically active compound in a combination of the invention. As used herein, the term "physiologically functional derivative" includes any: physiologically acceptable salt, ether, ester, prodrug, solvate, stereoisomer including enantiomer, diastereomer or stereoisomerically enriched or racemic mixture, and any other compound which upon administration to the recipient, is capable of providing (directly or indirectly) such a compound or an antivirally active metabolite or residue thereof.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

The compounds of the combinations of the invention may be referred to as "active ingredients" or "pharmaceutically active agents."

The term "prodrug" as used herein refers to any compound that when administered to a biological system generates the drug substance, i.e. active ingredient, as a result of spontaneous chemical reaction(s), enzyme catalyzed chemical reaction(s), and/or metabolic chemical reaction(s).

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in Textbook of Drug Design and Development (1991), P. Krogsgaard-Larsen and H. Bundgaard, Eds. Harwood Academic Publishers, pp. 113-191). Prodrug moieties can serve to enhance solubility, absorption and lipophilicity to optimize drug delivery, bioavailability and efficacy. A "prodrug" is thus a covalently modified analog of a therapeutically-active compound.

"Alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups consist of 1-18 saturated and/or unsaturated carbons, such as normal, secondary, tertiary or cyclic carbon atoms. Examples include, but are not limited to: methyl, Me (—CH$_3$), ethyl, Et (—CH$_2$CH$_3$), acetylenic (—C≡CH), ethylene, vinyl (—CH=CH$_2$), 1-propyl, n-Pr, n-propyl (—CH$_2$CH$_2$CH$_3$), 2-propyl, i-Pr, i-propyl (—CH(CH$_3$)$_2$), allyl (—CH$_2$CH=CH$_2$), propargyl (—CH$_2$C≡CH), cyclopropyl (—C$_3$H$_5$), 1-butyl, n-Bu, n-butyl (—CH$_2$CH$_2$CH$_2$CH$_3$), 2-methyl-1-propyl, i-Bu, i-butyl (—CH$_2$CH(CH$_3$)$_2$), 2-butyl, s-Bu, s-butyl (—CH(CH$_3$)CH$_2$CH$_3$), 2-methyl-2-propyl, t-Bu, t-butyl (—C(CH$_3$)$_3$), 1-pentyl, n-pentyl, (—CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), cyclopentyl (—C$_5$H$_9$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 5-hexenyl (—CH$_2$CH$_2$CH$_2$CH=CH$_2$) 1-hexyl (—CH(CH$_3$)CH$_2$CH$_2$CH$_3$), 3-hexyl (—CH(CH$_2$CH$_3$)(CH$_2$CH$_2$CH$_3$)), cyclohexyl (—C$_6$H$_{11}$), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), and 3,3-dimethyl-2-butyl (—CH(CH$_3$)C(CH$_3$)$_3$.

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group 6 to 20 carbon atoms e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O)O$_2$RR —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, or prodrug moiety.

"Heteroaryl" and "Heterocycle" refer to a ring system in which one or more ring atoms is a heteroatom, e.g. nitrogen, oxygen, and sulfur. Heterocycles are described in: Katritzky, Alan R., Rees, C. W., and Scriven, E. *Comprehensive Heterocyclic Chemistry* (1996) Pergamon Press; Paquette, Leo A.; *Principles of Modern Heterocyclic Chemistry* W. A. Benjamin, New York, (1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28. Exemplary heterocycles include but are not limited to substituents, i.e. radicals, derived from pyrrole, indole, furan, benzofuran, thiophene, benzothiophene, 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, purine, cinnoline, pthalazine, quinazoline, quinoxaline, 3-(1,2,4-N)-triazolyl, 5-(1,2,4-IV)-triazolyl, 5-tetrazolyl, 3-N)-oxazole, 5-(1-O, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, and benzimidazole.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer is also referred to as an enantiomer, and a mixture of such isomers is often called an enantiomeric mixture. A 50:50 mixture of enantiomers is referred to as a racemic mixture or a racemate. The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Active Ingredients of the Combinations

The present invention provides novel combinations of two or more active ingredients being employed together. In some embodiments, a synergistic antiviral effect is achieved. In other embodiments, a chemically stable combination is obtained. The combinations include at least one active ingredient selected from (1) tenofovir disoproxil fumarate and physiologically functional derivatives, and at least one active ingredient selected from (2) emtricitabine and physiologically functional derivatives. The term "synergistic antiviral effect" is used herein to denote an antiviral effect which is greater than the predicted purely additive effects of the individual components (a) and (b) of the combination.

Tenofovir disoproxil fumarate (also known as Viread®, Tenofovir DF, Tenofovir disoproxil, TDF, Bis-POC-PMPA (U.S. Pat. Nos. 5,935,946, 5,922,695, 5,977,089, 6,043,230, 6,069,249) is a prodrug of tenofovir, and has the structure:

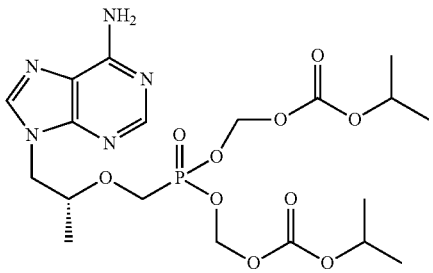 [SMILES: CC(C)OC(=O)OCOP(=O)(CO[C@H](C)Cn1cnc2c(N)ncnc21)OCOC(=O)OC(C)C]

and including fumarate salt ($HO_2CCH_2CH_2CO_2^-$).

The chemical names for Tenofovir disoproxil include: [2-(6-amino-purin-9-yl)-1-methyl-ethoxymethyl]-phosphonic acid diisopropoxycarbonyloxymethyl ester; 9-[(R)-2-[[bis[[(isopropoxycarbonyl)oxy]methoxy]phosphinyl]methoxy]propyl]adenine; and 2,4,6,8-tetraoxa-5-phosphanonanedioic acid, 5-[[(1R)-2-(6-amino-9H-purin-9-yl)-1-methylethoxy]methyl]-, bis(1-methylethyl) ester, 5-oxide. The CAS Registry numbers include: 201341-05-1; 202138-50-9; 206184-49-8. It should be noted that the ethoxymethyl unit of tenofovir has a chiral center. The R (rectus, right handed configuration) enantiomer is shown. However, the invention also includes the S isomer. The invention includes all enantiomers, diastereomers, racemates, and enriched stereoisomer mixtures of tenofovir (PMPA) and physiologically functional derivatives thereof.

PMPA or tenofovir (U.S. Pat. Nos. 4,808,716, 5,733,788, 6,057,305) has the structure:

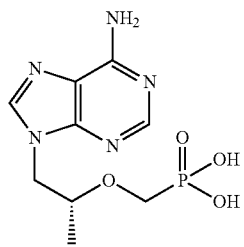 [SMILES: C[C@H](Cn1cnc2c(N)ncnc21)OCP(=O)(O)O]

The chemical names of PMPA, tenofovir include: (R)-9-(2-phosphonylmethoxypropyl)adenine; and phosphonic acid, [[(1R)-2-(6-amino-9H-purin-9-yl)-1-methylethoxy]methyl]. The CAS Registry number is 147127-20-6.

Tenofovir disoproxil fumarate (DF) is a nucleotide reverse transcriptase inhibitor approved in the United States in 2001 for the treatment of HIV-1 infection in combination with other antiretroviral agents. Tenofovir disoproxil fumarate or Viread® (Gilead Science, Inc.) is the fumarate salt of tenofovir disoproxil. Viread® may be named as: 9-[(R)-2-[[bis[[(isopropoxycarbonyl)oxy]methoxy]phosphinyl]methoxy]propyl]adenine fumarate (1:1); or 2,4,6,8-tetraoxa-5-phosphanonanedioic acid, 5-[[(1R)-2-(6-amino-9H-purin-9-yl)-1-methylethoxy]methyl]-, bis(1-methylethyl) ester, 5-oxide, (2E)-2-butenedioate (1:1). The CAS Registry number is 202138-50-9.

Physiologically functional derivatives of tenofovir disoproxil fumarate include PMEA (adefovir, 9-((R)-2-(phosphonomethoxy)ethyl)adenine) and PMPA compounds. Exemplary combinations include a PMEA or PMPA compound in combination with emtricitabine or 3TC. PMEA and PMPA compounds have the structures:

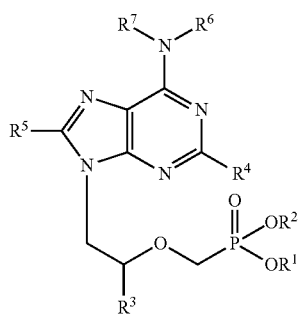

where PMEA ($R^3$ is H) and PMPA ($R^3$ is $C_1$-$C_6$ alkyl, $C_1$-$C_6$ substituted alkyl, or $CH_2OR^8$ where $R^8$ is $C_1$-$C_6$ alkyl, $C_1$-$C_6$ hydroxyalkyl or $C_1$-$C_6$ haloalkyl. $R^6$ and $R^7$ are independently H or $C_1$-$C_6$ alkyl. $R^4$ and $R^5$ are independently H, $NH_2$, NHR or $NR_2$ where R is $C_1$-$C_6$ alkyl. $R^1$ and $R^2$ are independently H, $C_1$-$C_6$ alkyl, $C_1$-$C_6$ substituted alkyl, $C_6$-$C_{20}$ aryl, $C_6$-$C_{20}$ substituted aryl, $C_6$-$C_{20}$ arylalkyl, $C_6$-$C_{20}$ substituted arylalkyl, acyloxymethyl esters —$CH_2OC(=O)R^9$ (e.g. POM) or acyloxymethyl carbonates —$CH_2OC(=O)OR^9$ (e.g. POC) where $R^9$ is $C_1$-$C_6$ alkyl, $C_1$-$C_6$ substituted alkyl, $C_6$-$C_{20}$ aryl or $C_6$-$C_{20}$ substituted aryl. For example, $R_1$ and $R_2$ may be pivaloyloxymethoxy, POM, —$CH_2OC(=O)C(CH_3)_3$; —$CH_2OC(=O)OC(CH_3)_3$; or POC, —$CH_2OC(=O)OCH(CH_3)_2$. Also for example, tenofovir has the structure where $R^3$ is $CH_3$, and $R^1$, $R^2$, $R^4$, $R^5$, $R^6$ and $R^7$ are H. Dialkyl phosphonates may be prepared according to the methods of: Quast et al (1974) *Synthesis* 490; Stowell et al (1990) *Tetrahedron Lett.* 3261; U.S. Pat. No. 5,663,159.

The PMPA compound may be enantiomerically-enriched or purified (single stereoisomer) where the carbon atom bearing $R^3$ may be the R or S enantiomer. The PMPA compound may be a racemate, i.e. a mixture of R and S stereoisomers.

Adefovir (9-(2-phosphonomethoxyethyl)adenine where $R_1$-$R_7$=H) is an exemplary PMEA compound (U.S. Pat. Nos. 4,808,716, 4,724,233). As the bis-pivalate prodrug, Adefovir dipivoxil, also known as bis-POM PMEA, ($R_3$-$R_7$=H, $R_1$ and $R_2$=—$CH_2OC(=O)C(CH_3)_3$, pivoxil, POM, pivaloyloxymethoxy), is effective against HIV and Hepatitis B infections (U.S. Pat. Nos. 5,663,159, 6,451,340). Adefovir dipivoxil has demonstrated minor to moderate synergistic inhibition of HIV replication in combination with other compounds with anti-HIV activity including PMPA, d4T, ddC, nelfinavir, ritonavir, and saquinavir (Mulato et al (1997) *Antiviral Research* 36:91-97).

The invention includes all enantiomers, diastereomers, racemates, and enriched stereoisomer mixtures of PMEA and PMPA, and physiologically functional derivatives thereof.

Emtricitabine ((–)-cis-FTC, Emtriva™), a single enantiomer of FTC, is a potent nucleoside reverse transcriptase inhibitor approved for the treatment of HIV (U.S. Pat. Nos. 5,047,407, 5,179,104, 5,204,466, 5,210,085, 5,486,520, 5,538,975, 5,587,480, 5,618,820, 5,763,606, 5,814,639, 5,914,331, 6,114,343, 6,180,639, 6,215,004; WO 02/070518). The single enantiomer emtricitabine has the structure:

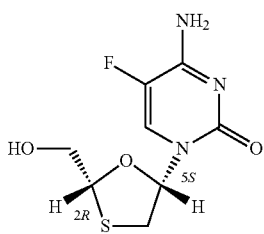 [SMILES: Nc1nc(=O)n([C@@H]2CS[C@H](CO)O2)cc1F]

The chemical names for emtricitabine include: (−)-cis-FTC; β-L-hydroxymethyl-5-(5-fluorocytosin-1-yl)-1,3-oxathiolane; (2R,5S)-5-fluoro-1-[2-(hydroxymethyl)-1,3-oxathiolan-5-yl]cytosine; and 4-amino-5-fluoro-1-(2-hydroxymethyl-[1,3]-(2R,5S)-oxathiolan-5-yl)-1H-pyrimidin-2-one. The CAS Registry numbers include: 143491-57-0; 143491-54-7. It should be noted that FTC contains two chiral centers, at the 2 and 5 positions of the oxathiolane ring, and therefore can exist in the form of two pairs of optical isomers (i.e. enantiomers) and mixtures thereof including racemic mixtures. Thus, FTC may be either a cis or a trans isomer or mixtures thereof. Mixtures of cis and trans isomers are diastereomers with different physical properties. Each cis and trans isomer can exist as one of two enantiomers or mixtures thereof including racemic mixtures. The invention includes all enantiomers, diastereomers, racemates, and enriched stereoisomer mixtures of emtricitabine and physiologically functional derivatives thereof. For example, the invention includes physiological functional derivatives such as the 1:1 racemic mixture of the enantiomers (2R,5S,cis)-4-amino-5-fluoro-1-(2-hydroxymethyl-1,3-oxathiolan-5-yl)-(1H)-pyrimidin-2-one (emtricitabine) and its mirror image (2S,5R,cis)-4-amino-5-fluoro-1-(2-hydroxymethyl-1,3-oxathiolan-5-yl)-(1H)-pyrimidin-2-one, or mixtures of the two enantiomers in any relative amount. The invention also includes mixtures of cis and trans forms of FTC.

Physiologically functional derivatives of emtricitabine include 1,3 oxathiolane nucleosides having the structure:

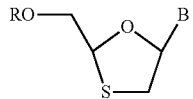

In the 1,3 oxathiolane nucleoside structure above, B is a nucleobase including any nitrogen-containing heterocyclic moiety capable of forming Watson-Crick hydrogen bonds in pairing with a complementary nucleobase or nucleobase analog, e.g. a purine, a 7-deazapurine, or a pyrimidine. Examples of B include the naturally occurring nucleobases: adenine, guanine, cytosine, uracil, thymine, and minor constituents and analogs of the naturally occurring nucleobases, e.g. 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, 5-fluorocytosine, 5-chlorocytosine, 5-bromocytosine, 5-iodocytosine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, pyrazolo[3,4-D]pyrimidines (U.S. Pat. Nos. 6,143,877 and 6,127,121; WO 01/38584), and ethenoadenine (Farman (1989) in Practical Handbook of Biochemistry and Molecular Biology, pp. 385-394, CRC Press, Boca Raton, Fla.).

Nucleobases B may be attached in the configurations of naturally-occurring nucleic acids to the 1,3 oxathiolane moiety through a covalent bond between the N−9 of purines, e.g. adenin-9-yl and guanin-9-yl, or N−1 of pyrimidines, e.g. thymin-1-yl and cytosin-1-yl (Blackburn, G. and Gait, M. Eds. "DNA and RNA structure" in Nucleic Acids in Chemistry and Biology, $2^{nd}$ Edition, (1996) Oxford University Press, pp. 15-81).

Also in the 1,3 oxathiolane nucleoside structure above, R is H, $C_1$-$C_{18}$ alkyl, $C_1$-$C_{18}$ substituted alkyl, $C_2$-$C_{18}$ alkenyl, $C_2$-$C_{18}$ substituted alkenyl, $C_2$-$C_{18}$ alkynyl, $C_2$-$C_{18}$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, phosphonate, phosphophosphonate, diphosphophosphonate, phosphate, diphosphate, triphosphate, polyethyleneoxy, or a prodrug moiety.

Physiologically functional derivatives of emtricitabine also include 3TC (lamivudine, Epivir®), a reverse transcriptase inhibitor approved in the United States for the treatment of HIV-1 infection in combination with AZT as Combivir® (GlaxoSmithKline). U.S. Pat. Nos. 5,859,021; 5,905,082; 6177435; 5627186; 6417191. Lamivudine (U.S. Pat. Nos. 5,587,480, 5,696,254, 5,618,820, 5,756,706, 5,744,596, 568,164, 546,6806, 5,151,426) has the structure:

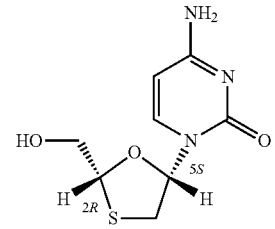 [SMILES: Nc1ccn([C@@H]2CS[C@H](CO)O2)c(=O)n1]

For example and for some therapeutic uses, 3TC may be a physiologically functional derivative of emtricitabine in combination with tenofovir DF or a physiologically functional derivative of tenofovir DF.

It will be appreciated that tenofovir DF and emtricitabine, and their physiologically functional derivatives may exist in keto or enol tautomeric forms and the use of any tautomeric form thereof is within the scope of this invention. Tenofovir DF and emtricitabine will normally be utilized in the combinations of the invention substantially free of the corresponding enantiomer, that is to say no more than about 5% w/w of the corresponding enantiomer will be present.

Prodrugs

The invention includes all prodrugs of tenofovir and emtricitabine. An exemplary prodrug of tenofovir is tenofovir disoproxil fumarate (TDF, Viread®). A large number of structurally-diverse prodrugs have been described for phosphonic acids (Freeman and Ross in Progress in Medicinal Chemistry 34: 112-147 (1997). A commonly used prodrug class is the acyloxyalkyl ester, which was first used as a prodrug strategy for carboxylic acids and then applied to phosphates and phosphonates by Farquhar et al (1983) J.

*Pharm. Sci.* 72: 324; also U.S. Pat. Nos. 4,816,570, 4,968, 788, 5,663,159 and 5,792,756. Subsequently, the acyloxyalkyl ester was used to deliver phosphonic acids across cell membranes and to enhance oral bioavailability. A close variant of the acyloxyalkyl ester strategy, the alkoxycarbonyloxyalkyl ester, may also enhance oral bioavailability as a prodrug moiety in the compounds of the combinations of the invention. Aryl esters of phosphorus groups, especially phenyl esters, are reported to enhance oral bioavailability (DeLambert et al (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al (1992) *J. Chem. Soc. Perkin Trans.* I2345; Brook et al WO 91/19721. Still other benzylic prodrugs have been described containing a carboxylic ester-containing group attached to the benzylic methylene (Glazier et al WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al (1993) *Antiviral Res.*, 22: 155-174; Benzaria et al (1996) *J. Med. Chem.* 39: 4958). Cyclic phosphonate esters have also been described as prodrugs of phosphorus-containing compounds.

Prodrug esters in accordance with the invention are independently selected from the following groups: (1) mono-, di-, and tri-phosphate esters of tenofovir or emtricitabine or any other compound which upon administration to a human subject is capable of providing (directly or indirectly) said mono-, di, or triphosphate ester; (2) carboxylic acid esters (3) sulphonate esters, such as alkyl- or aralkylsulphonyl (for example, methanesulphonyl); (4) amino acid esters (for example, alanine, L-valyl or L-isoleucyl); (5) phosphonate; and (6) phosphonamidate esters.

Ester groups (1)-(6) may be substituted with; straight or branched chain $C_1$-$C_{18}$ alkyl (for example, methyl, n-propyl, t-butyl, or n-butyl); $C_3$-$C_{12}$ cycloalkyl; alkoxyalkyl (for example, methoxymethyl); arylalkyl (for example, benzyl); aryloxyalkyl (for example, phenoxymethyl); $C_5$-$C_{20}$ aryl (for example, phenyl optionally substituted by, for example, halogen, $C_1$-$C_4$ alkyl, $C_1$-$C_4$ alkoxy, or amino; acyloxymethyl esters —$CH_2OC(=O)R^9$ (e.g. POM) or acyloxymethyl carbonates —$CH_2OC(=O)OR^9$ (e.g. POC) where $R^9$ is $C_1$-$C_6$ alkyl, $C_1$-$C_6$ substituted alkyl, $C_6$-$C_{20}$ aryl or $C_6$-$C_{20}$ substituted aryl. For example, ester groups may be: —$CH_2OC(=O)C(CH_3)_3$, —$CH_2OC(=O)OC(CH_3)_3$ or —$CH_2OC(=O)OCH(CH_3)_2$.

An exemplary aryl moiety present in such esters comprises a phenyl or substituted phenyl group. Many phosphate prodrug moieties are described in U.S. Pat. No. 6,312,662; Jones et al (1995) *Antiviral Research* 27:1-17; Kucera et al (1990) *AIDS Res. Hum. Retro Viruses* 6:491-501; Piantadosi et al (1991) *J. Med. Chem.* 34:1408-14; Hosteller et al (1992) *Antimicrob. Agents Chemother.* 36:2025-29; Hostetler et al (1990) *J. Biol. Chem.* 265:611127; and Siddiqui et al (1999) *J. Med. Chem.* 42:4122-28.

Pharmaceutically acceptable prodrugs refer to a compound that is metabolized in the host, for example hydrolyzed or oxidized, by either enzymatic action or by general acid or base solvolysis, to form an active ingredient. Typical examples of prodrugs of the active ingredients of the combinations of the invention have biologically labile protecting groups on a functional moiety of the active compound. Prodrugs include compounds that can be oxidized, reduced, aminated, deaminated, esterified, deesterified, alkylated, dealkylated, acylated, deacylated, phosphorylated, dephosphorylated, or other functional group change or conversion involving forming or breaking chemical bonds on the prodrug.

Chemical Stability of a Pharmaceutical Formulation

The chemical stability of the active ingredients in a pharmaceutical formulation is of concern to minimize the generation of impurities and ensure adequate shelf-life. The active ingredients, tenofovir disoproxil fumarate and emtricitabine, in the pharmaceutical formulations of the invention have relatively low pKa values, indicative of the potential to cause acidic hydrolysis of the active ingredients. Emtricitabine, with a pKa of 2.65 (Emtriva™ Product Insert, Gilead Sciences, Inc. 2003, available at gilead.com) is subject to hydrolytic deamination of the 5-fluoro cytosine nucleobase to form the 5-fluoro uridine nucleobase. Tenofovir disoproxil fumarate, with a pKa of 3.75 (Yuan L. et al "Degradation Kinetics of Oxycarbonyloxymethyl Prodrugs of Phosphonates in Solution", *Pharmaceutical Research* (2001) Vol. 18, No. 2, 234-237), is subject also to hydrolytic deamination of the exocyclic amine of the adenine nucleobase, and to hydrolysis of one or both of the POC ester groups (U.S. Pat. No. 5,922,695). It is desirable to formulate a therapeutic combination of tenofovir disoproxil fumarate and emtricitabine, and the physiological functional derivatives thereof, with a minimum of impurities and adequate stability.

The combinations of the present invention provide combination pharmaceutical dosage forms which are chemically stable to acid degradation of: (1) a first component (such as tenofovir disoproxil fumarate, and physiological functional derivatives; (2) a second component (such as emtricitabine, and physiological functional derivatives; and (3) optionally a third component having antiviral activity. The third component includes anti-HIV agents and include: protease inhibitors (PI), nucleoside reverse transcriptase inhibitors (NRTI), non-nucleoside reverse transcriptase inhibitors (NNRTI), and integrase inhibitors. Exemplary third active ingredients to be administered in combination with first and second components are shown in Table A. First and second components are as defined in the above section entitled: ACTIVE INGREDIENTS OF THE COMBINATIONS.

Salts

Any reference to any of the compounds in the compositions of the invention also includes any physiologically acceptable salt thereof. Examples of physiologically acceptable salts of tenofovir DF, emtricitabine and their physiologically functional derivatives include salts derived from an appropriate base, such as an alkali metal (for example, sodium), an alkaline earth (for example, magnesium), ammonium and $NX_4^+$ (wherein X is $C_1$-$C_4$ alkyl), or an organic acid such as fumaric acid, acetic acid, succinic acid. Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the combinations of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

Administration of the Formulations

While it is possible for the active ingredients of the combination to be administered alone and separately as monotherapies, it is preferable to administer them as a pharmaceutical co-formulation. A two-part or three-part combination may be administered simultaneously or sequentially. When administered sequentially, the combination may be administered in one, two, or three administrations.

Preferably, two-part or three-part combinations are administered in a single pharmaceutical dosage form. More preferably, a two-part combination is administered as a single oral dosage form and a three-part combination is administered as two identical oral dosage forms. Examples include a single tablet of tenofovir disoproxil fumarate and emtricitabine, or two tablets of tenofovir disoproxil fumarate, emtricitabine, and efavirenz.

It will be appreciated that the compounds of the combination may be administered: (1) simultaneously by combination of the compounds in a co-formulation or (2) by alternation, i.e. delivering the compounds serially, sequentially, in parallel or simultaneously in separate pharmaceutical formulations. In alternation therapy, the delay in administering the second, and optionally a third active ingredient, should not be such as to lose the benefit of a synergistic therapeutic effect of the combination of the active ingredients. By either method of administration (1) or (2), ideally the combination should be administered to achieve peak plasma concentrations of each of the active ingredients. A one pill once-per-day regimen by administration of a combination co-formulation may be feasible for some HIV-positive patients. Effective peak plasma concentrations of the active ingredients of the combination will be in the range of approximately 0.001 to 100 µM. Optimal peak plasma concentrations may be achieved by a formulation and dosing regimen prescribed for a particular patient. It will also be understood that tenofovir DF and emtricitabine, or the physiologically functional derivatives of either thereof, whether presented simultaneously or sequentially, may be administered individually, in multiples, or in any combination thereof. In general, during alternation therapy (2), an effective dosage of each compound is administered serially, where in co-formulation therapy (1), effective dosages of two or more compounds are administered together.

Formulation of the Combinations

When the individual components of the combination are administered separately they are generally each presented as a pharmaceutical formulation. The references hereinafter to formulations refer unless otherwise stated to formulations containing either the combination or a component compound thereof. It will be understood that the administration of the combination of the invention by means of a single patient pack, or patient packs of each formulation, within a package insert diverting the patient to the correct use of the invention is a desirable additional feature of this invention. The invention also includes a double pack comprising in association for separate administration, formulations of tenofovir disoproxil fumarate and emtricitabine, or a physiologically functional derivative of either or both thereof.

The combination therapies of the invention include: (1) a combination of tenofovir DF and emtricitabine or (2) a combination containing a physiologically functional derivative of either or both thereof.

The combination may be formulated in a unit dosage formulation comprising a fixed amount of each active pharmaceutical ingredient for a periodic, e.g. daily, dose or subdose of the active ingredients.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared (*Remington's Pharmaceutical Sciences* (Mack Publishing Co., Easton, Pa.). Compositions intended for oral use may be prepared according to any method known to the art for the manufacture of pharmaceutical compositions and such compositions may contain one or more agents including antioxidants, sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and absorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example pregelatinized starch, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose, sucralose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid, BHT, etc.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions or liposome formulations. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The pharmaceutical compositions of the invention may be injected parenterally, for example, intravenously, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The pharmaceutical compositions of the invention may also be administered intranasally or by inhalation and are conveniently delivered in the form of a dry powder inhaler or an aerosol spray presentation from a pressurized container or a nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFC 134a), carbon dioxide or other suitable gas. In the case of a pressurized aerosol, the dosage unit may be determined by providing a valve to deliver a metered amount. The pressurized container or nebuliser may contain a solution or suspension of the composition, e.g. using a mixture of ethanol and the propellant as the solvent, which may additional contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch. Aerosol or dry powder formulations are preferably arranged so that each metered dose or "puff" contains from 20 µg to 20 mg of a composition for delivery to the patient. The overall daily dose with an aerosol will be in the range of from 20 µg to 20 mg which may be administered in a single dose or, more usually, in divided doses throughout the day.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur. As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

The combinations of the invention may conveniently be presented as a pharmaceutical formulation in a unitary dosage form. A convenient unitary dosage formulation contains the active ingredients in any amount from 1 mg to 1 g each, for example but not limited to, 10 mg to 300 mg. The synergistic effects of tenofovir DF in combination with emtricitabine may be realized over a wide ratio, for example 1:50 to 50:1 (tenofovir DF:emtricitabine). In one embodiment, the ratio may range from about 1:10 to 10:1. In another embodiment, the weight/weight ratio of tenofovir to emtricitabine in a co-formulated combination dosage form, such as a pill, tablet, caplet or capsule will be about 1, i.e. an approximately equal amount of tenofovir DF and emtricitabine. In other exemplary co-formulations, there may be more or less tenofovir than FTC. For example, 300 mg tenofovir DF and 200 mg emtricitabine can be co-formulated in a ratio of 1.5:1 (tenofovir DF: emtricitabine). In one embodiment, each compound will be employed in the combination in an amount at which it exhibits antiviral activity when used alone. Exemplary Formulations A, B, C, D, E, and F (Examples) have ratios of 12:1 to 1:1 (tenofovir DF:emtricitabine). Exemplary Formulations A, B, C, D, E, and F use amounts of tenofovir DF and emtricitabine ranging from 25 mg to 300 mg. Other ratios and amounts of the compounds of said combinations are contemplated within the scope of the invention.

A unitary dosage form may further comprise tenofovir DF and emtricitabine, or physiologically functional derivatives of either thereof, and a pharmaceutically acceptable carrier.

It will be appreciated by those skilled in the art that the amount of active ingredients in the combinations of the invention required for use in treatment will vary according to a variety of factors, including the nature of the condition being treated and the age and condition of the patient, and will ultimately be at the discretion of the attending physician or health care practitioner. The factors to be considered include the route of administration and nature of the formulation, the animal's body weight, age and general condition and the nature and severity of the disease to be treated. For example, in a Phase I/II monotherapy study of emtricitabine, patients received doses ranging from 25 mg to 200 mg twice-a-day for two weeks. At each dose regimen greater or equal to 200 mg, a 98-percent (1.75 log 10) or greater viral suppression was observed. A once-a-day dose of 200 mg of emtricitabine reduced the viral load by an average of 99 percent (1.92 log 10). Viread® (tenofovir DF) has been approved by the FDA for the treatment and prophylaxis of HIV infection as a 300 mg oral tablet. Emtriva™ (emtricitabine) has been approved by the FDA for the treatment of HIV as a 200 mg oral tablet.

It is also possible to combine any two of the active ingredients in a unitary dosage form for simultaneous or sequential administration with a third active ingredient. The three-part combination may be administered simultaneously or sequentially. When administered sequentially, the combination may be administered in two or three administrations. Third active ingredients have anti-HIV activity and include protease inhibitors (PI), nucleoside reverse transcriptase inhibitors (NRTI), non-nucleoside reverse transcriptase inhibitors (NNRTI), and integrase inhibitors. Exemplary third active ingredients to be administered in combination with tenofovir DF, emtricitabine, and their physiological functional derivatives, are shown in Table A.

TABLE A 5,6 dihydro-5-azacytidine
5-aza 2'deoxycytidine
5-azacytidine
5-yl-carbocyclic 2'-deoxyguanosine (BMS200,475)
9 (arabinofuranosyl)guanine; 9-(2' deoxyribofuranosyl)guanine
9-(2'-deoxy 2'fluororibofuranosyl)-2,6-diaminopurine
9-(2'-deoxy 2'fluororibofuranosyl)guanine
9-(2'-deoxyribofuranosyl)-2,6 diaminopurine
9-(arabinofuranosyl)-2,6 diaminopurine
Abacavir, Ziagen ®
Acyclovir, ACV; 9-(2-hydroxyethoxylmethyl)guanine
Adefovir dipivoxil, Hepsera ®
amdoxivir, DAPD
Amprenavir, Agenerase ®
araA; 9-β-D-arabinofuranosyladenine (Vidarabine)
atazanivir sulfate (Reyataz ®)
AZT; 3'-azido-2',3'-dideoxythymdine, Zidovudine, (Retrovir ®)
BHCG; (.+-.)-(1a,2b,3a)-9-[2,3-bis(hydroxymethyl)cyclobutyl]guanine
BMS200,475; 5-yl-carbocyclic 2'-deoxyguanosine TABLE A-continued Buciclovir; (R) 9-(3,4-dihydroxybutyl)guanine
BvaraU; 1-β-D-arabinofuranosyl-E-5-(2-bromovinyl)uracil (Sorivudine)
Calanolide A
Capravirine
CDG; carbocyclic 2'-deoxyguanosine
Cidofovir,
HPMPC; (S)-9-(3-hydroxy-2-phosphonylmethoxypropyl)cytosine
Clevudine, L-FMAU; 2'-Fluoro-5-methyl-β-L-arabino-furanosyluracil
Combivir ® (lamivudine/zidovudine)
Cytallene; [1-(4'-hydroxy-1',2'-butadienyl)cytosine]
d4C; 3'-deoxy-2',3'-didehydrocytidine
DAPD; (−)-β-D-2,6-diaminopurine dioxolane
ddA; 2',3'-dideoxyadenosine
ddAPR; 2,6-diaminopurine-2',3'-dideoxyriboside
ddC; 2',3'-dideoxycytidine (Zalcitabine)
ddI; 2',3'-dideoxyinosine, didanosine, (Videx ®, Videx ® EC)
Delavirdine, Rescriptor ®
Didanosine, ddI, Videx ®; 2',3'-dideoxyinosine
DXG; dioxolane guanosine
E-5-(2-bromovinyl)-2'-deoxyuridine
Efavirenz, Sustiva ®
Enfuvirtide, Fuzeon ®
F-ara-A; fluoroarabinosyladenosine (Fludarabine)
FDOC; (−)-β-D-5-fluoro-1-[2-(hydroxymethyl)-1,3-dioxolane]cytosine
FEAU; 2'-deoxy-2'-fluoro-1-β-D-arabinofuranosyl-5-ethyluracil
FIAC; 1-(2-deoxy-2-fluoro-β-D-arabinofuranosyl)-5-iodocytosine
FIAU; 1-(2-deoxy-2-fluoro-β-D-arabinofuranosyl)-5-iodouridine
FLG; 2',3'-dideoxy-3'-fluoroguanosine
FLT; 3'-deoxy-3'-fluorothymidine
Fludarabine; F-ara-A; fluoroarabinosyladenosine
FMAU; 2'-Fluoro-5-methyl-β-L-arabino-furanosyluracil
FMdC
Foscarnet; phosphonoformic acid, PFA
FPMPA; 9-(3-fluoro-2-phosphonylmethoxypropyl)adenine
Gancyclovir, GCV; 9-(1,3-dihydroxy-2-propoxymethyl)guanine
GS-7340; 9-[R-2-[[(S)-[[(S)-1-(isopropoxycarbonyl)ethyl]amino]-phenoxyphosphinyl]methoxy]propyl]adenine
HPMPA; (S)-9-(3-hydroxy-2-phosphonylmethoxypropyl)adenine
HPMPC; (S)-9-(3-hydroxy-2-phosphonylmethoxypropyl)cytosine (Cidofovir)
Hydroxyurea, Droxia ®
Indinavir, Crixivan ®
Kaletra ® (lopinavir/ritonavir)
Lamivudine,
3TC, Epivir ™; (2R, 5S, cis)-4-amino-1-(2-hydroxymethyl-1,3-oxathiolan-5-yl)-(1H)-pyrimidin-2-one
L-d4C; L-3'-deoxy-2',3'-didehydrocytidine
L-ddC; L-2',3'-dideoxycytidine
L-Fd4C; L-3'-deoxy-2',3'-didehydro-5-fluorocytidine
L-FddC; L-2',3'-dideoxy-5-fluorocytidine
Lopinavir
Nelfinavir, Viracept ®
Nevirapine, Viramune ®
Oxetanocin A;
9-(2-deoxy-2-hydroxymethyl-β-D-erythro-oxetanosyl)adenine
Oxetanocin G;
9-(2-deoxy-2-hydroxymethyl-β-D-erythro-oxetanosyl)guanine
Penciclovir
PMEDAP; 9-(2-phosphonylmethoxyethyl)-2,6-diaminopurine
PMPA, tenofovir; (R)-9-(2-phosphonylmethoxypropyl)adenine
PPA; phosphonoacetic acid
Ribavirin; 1-β-D-ribofuranosyl-1,2,4-triazole-3-carboxamide
Ritonavir, Norvir ®
Saquinavir, Invirase ®, Fortovase ®
Sorivudine, BvaraU; 1-β-D-arabinofuranosyl-E-5-(2-bromovinyl)uracil
Stavudine, d4T, Zerit ®; 2',3'-didehydro-3'-deoxythymidine
Trifluorothymidine, TFT; Trifluorothymidine
Trizivir ® (abacavir sulfate/lamivudine/zidovudine)
Vidarabine, araA; 9-β-D-arabinofuranosyladenine
Zalcitabine, Hivid ®, ddC; 2',3'-dideoxycytidine
Zidovudine, AZT, Retrovir ®; 3'-azido-2',3'-dideoxythymdine
Zonavir; 5-propynyl-1-arabinosyluracil Another aspect of the present invention is a three-part combination comprising tenofovir DF, FTC, and 9-[(R)-2-[[(5)-[[(S)-1-(isopropoxycarbonyl)ethyl]amino]phenoxyphosphinyl]methoxy]propyl] adenine, also designated herein as GS-7340, which has the structure:

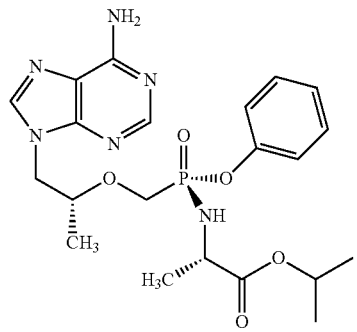 [SMILES: CC(C)OC(=O)[C@H](C)N[P@](=O)(CO[C@H](C)Cn1cnc2c(N)ncnc21)Oc1ccccc1]

GS-7340 is a prodrug of tenofovir and the subject of commonly owned, pending application, U.S. Ser. No. 09/909,560, filed Jul. 20, 2001 and Becker et al WO 02/08241.

For example, a ternary unitary dosage may contain 1 mg to 1000 mg of tenofovir disoproxil fumarate, 1 mg to 1000 mg of emtricitabine, and 1 mg to 1000 mg of the third active ingredient. As a further feature of the present invention, a unitary dosage form may further comprise tenofovir DF, emtricitabine, the third active ingredient, or physiologically functional derivatives of the three active ingredients thereof, and a pharmaceutically acceptable carrier.

Combinations of the present invention enable patients greater freedom from multiple dosage medication regimens and ease the needed diligence required in remembering and complying with complex daily dosing times and schedules. By combining tenofovir disoproxil fumarate and emtricitabine into a single dosage form, the desired daily regimen may be presented in a single dose or as two or more sub-doses per day. The combination of co-formulated tenofovir DF and emtricitabine may be administered as a single pill, once per day.

A further aspect of the invention is a patient pack comprising at least one active ingredient: tenofovir disoproxil fumarate, emtricitabine, or a physiologically functional derivative of either of the combination and an information package or product insert containing directions on the use of the combination of the invention.

Segregation of active ingredients in pharmaceutical powders and granulations is a widely recognized problem that can result in inconsistent dispersions of the active ingredients in final dosage forms. Some of the main factors contributing to segregation are particle size, shape and density. Segregation is particularly troublesome when attempting to formulate a single homogenous tablet containing multiple active ingredients having different densities and different particle sizes. Glidants are substances that have traditionally been used to improve the flow characteristics of granulations and powders by reducing interparticulate friction. See Lieberman, Lachman, & Schwartz, *Pharmaceutical Dosage Forms: Tablets*, Volume 1, p. 177-178 (1989), incorporated herein by reference. Glidants are typically added to pharmaceutical compositions immediately prior to tablet compression to facilitate the flow of granular material into the die cavities of tablet presses. Glidants include: colloidal silicon dioxide, asbestos free talc, sodium aluminosilicate, calcium silicate, powdered cellulose, microcrystalline cellulose, corn starch, sodium benzoate, calcium carbonate, magnesium carbonate, metallic stearates, calcium stearate, magnesium stearate, zinc stearate, stearowet C, starch, starch 1500, magnesium lauryl sulfate, and magnesium oxide. Exemplary Tablet Formulation A has colloidal silicon dioxide (Examples). Glidants can be used to increase and aid blend composition homogeneity in formulations of anti-HIV drugs (U.S. Pat. No. 6,113,920). The novel compositions of the present invention may contain glidants to effect and maintain homogeneity of active ingredients during handling prior to tablet compression.

The present invention provides pharmaceutical formulations combining the active ingredients tenofovir DF and emtricitabine, or physiologically functional derivatives thereof, in a sufficiently homogenized form, and a method for using this pharmaceutical formulation. An object of the present invention is to utilize glidants to reduce the segregation of active ingredients in pharmaceutical compositions during pre-compression material handling. Another object of the present invention is to provide a pharmaceutical formulation combining the active ingredients tenofovir DF and emtricitabine, or physiologically functional derivatives thereof, with a pharmaceutically acceptable glidant, resulting in a mixture characterized by a pharmaceutically acceptable measure of homogeneity.

Formulations include those suitable for oral, rectal, nasal, topical (including transdermal, buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods represent a further feature of the present invention and include the step of bringing into association the active ingredients with the carrier, which constitutes one or more accessory ingredients, and maintaining chemical stability. In general, the formulations are prepared by uniformly and intimately bringing into association the active ingredients with liquid carriers or finely divided solid carriers or both, and then if necessary shaping the product.

Formulations of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropyl methylcellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, cellulose ether derivatives (e.g., hydroxypropyl methylcellulose) or methacrylate derivatives in varying proportions to provide the desired release profile. Tablets may optionally be provided with an enteric coating, to provide release in parts of the gut other than the stomach.

Formulations suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration may be presented as a suppository with a suitable base comprising, for example, cocoa butter or a salicylates. Topical administration may also be by means of a transdermal iontophoretic device.

Formulations suitable for vaginal administration may be presented as pessaries, tampons, creams, gels, pastes, foams or spray formulations containing in addition to the active ingredient such carriers as are known in the art to be appropriate.

Formulations suitable for penile administration for prophylactic or therapeutic use may be presented in condoms, creams, gels, pastes, foams or spray formulations containing in addition to the active ingredient such carriers as are known in the art to be appropriate.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in moulds.

Formulations suitable for parenteral administration include aqueous and nonaqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Exemplary unit dosage formulations are those containing a daily dose or daily subdose of the active ingredients, as hereinbefore recited, or an appropriate fraction thereof. It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The compounds of the combination of the present invention may be obtained in a conventional manner, known to those skilled in the art. Tenofovir disoproxil fumarate can be prepared, for example, as described in U.S. Pat. No. 5,977,089. Methods for the preparation of FTC are described in WO 92/14743, incorporated herein by reference.

Composition Use

Compositions of the present invention are administered to a human or other mammal in a safe and effective amount as described herein. These safe and effective amounts will vary according to the type and size of mammal being treated and the desired results of the treatment. Any of the various methods known by persons skilled in the art for packaging tablets, caplets, or other solid dosage forms suitable for oral administration, that will not degrade the components of the present invention, are suitable for use in packaging. The combinations may be packaged in glass and plastic bottles. Tablets, caplets, or other solid dosage forms suitable for oral administration may be packaged and contained in various packaging materials optionally including a dessicant, e.g. silica gel. Packaging may be in the form of unit dose blister packaging. For example, a package may contain one blister tray of tenofovir DF and another blister tray of emtricitabine pills, tablets, caplets, or capsule. A patient would take one dose, e.g. a pill, from one tray and one from the other. Alternatively, the package may contain a blister tray of the co-formulated combination of tenofovir DF and emtricitabine in a single pill, tablet, caplet or capsule. As in other combinations and packaging thereof, the combinations of the invention include physiological functional derivatives of tenofovir DF and FTC.

The packaging material may also have labeling and information related to the pharmaceutical composition printed thereon. Additionally, an article of manufacture may contain a brochure, report, notice, pamphlet, or leaflet containing product information. This form of pharmaceutical information is referred to in the pharmaceutical industry as a "package insert." A package insert may be attached to or included with a pharmaceutical article of manufacture. The package insert and any article of manufacture labeling provides information relating to the pharmaceutical composition. The information and labeling provides various forms of information utilized by health-care professionals and patients, describing the composition, its dosage and various other parameters required by regulatory agencies such as the United States Food and Drug Agency.

Assays of the Combinations

The combinations of the inventions may be tested for in vitro activity against HIV and sensitivity, and for cytotoxicity in laboratory adapted cell lines, e.g. MT2 and in peripheral blood mononuclear cells (PBMC) according to standard assays developed for testing anti-HIV compounds, such as WO 02/068058 and U.S. Pat. No. 6,475,491. Combination assays may be performed at varying concentrations of the compounds of the combinations to determine $EC_{50}$ by serial dilutions.

Exemplary Formulations

The following examples further describe and demonstrate particular embodiments within the scope of the present invention. Techniques and formulations generally are found in *Remington's Pharmaceutical Sciences* (Mack Publishing Co., Easton, Pa.). The examples are given solely for illustration and are not to be construed as limitations as many variations are possible without departing from spirit and scope of the Invention. The following examples are intended for illustration only and are not intended to limit the scope of the invention in any way. "Active ingredient" denotes tenofovir disoproxil fumarate, emtricitabine, or a physiologically functional derivative of either thereof.

Tablet Formulation

The following exemplary formulations A, B, C, D, E, and F are prepared by wet granulation of the ingredients with an aqueous solution, addition of extragranular components and then followed by addition of magnesium stearate and compression.

Formulation A:

|  | mg/tablet |
| --- | --- |
| Tenofovir Disoproxil Fumarate | 300 |
| emtricitabine | 200 |
| Microcrystalline Cellulose | 200 |
| Lactose Monohydrate | 175 |
| Croscarmellose Sodium | 60 |
| Pregelatinized Starch | 50 |
| Colloidal silicon dioxide | 5 |
| Magnesium Stearate | 10 |
| total: | 1000 |

Formulation B:

|  | mg/tablet |
| --- | --- |
| Tenofovir Disoproxil fumarate | 300 |
| emtricitabine | 100 |
| Microcrystalline Cellulose | 200 |
| Lactose Monohydrate | 180 |
| Sodium Starch Glycollate | 60 |
| Pregelatinized Starch | 50 |
| Magnesium Stearate | 10 |
| total: | 900 |

Formulation C:

|  | mg/tablet |
| --- | --- |
| Tenofovir Disoproxil fumarate | 200 |
| emtricitabine | 200 |
| Microcrystalline Cellulose | 200 |
| Lactose Monohydrate | 180 |
| Sodium Starch Glycollate | 60 |
| Pregelatinized Starch | 50 |
| Magnesium Stearate | 10 |
| total: | 900 |

Formulation D:

|  | mg/tablet |
| --- | --- |
| Tenofovir Disoproxil fumarate | 300 |
| emtricitabine | 25 |
| Microcrystalline Cellulose | 200 |
| Lactose Monohydrate | 180 |
| Sodium Starch Glycollate | 60 |
| Pregelatinized Starch | 50 |
| Magnesium Stearate | 10 |
| total: | 825 |

Formulation E:

|  | mg/tablet |
| --- | --- |
| Tenofovir Disoproxil fumarate | 200 |
| emtricitabine | 25 |
| Microcrystalline Cellulose | 200 |
| Lactose Monohydrate | 180 |
| Sodium Starch Glycollate | 60 |
| Pregelatinized Starch | 50 |
| Magnesium Stearate | 10 |
| total: | 725 |

Formulation F:

|  | mg/tablet |
| --- | --- |
| Tenofovir Disoproxil fumarate | 100 |
| emtricitabine | 100 |
| Microcrystalline Cellulose | 200 |
| Lactose Monohydrate | 180 |
| Sodium Starch Glycollate | 60 |
| Pregelatinized Starch | 50 |
| Magnesium Stearate | 10 |
| total: | 700 |

Formulation G (Controlled Release Formulation):

This formulation is prepared by wet granulation of the ingredients with an aqueous solution, followed by the addition of magnesium stearate and compression.

|  | mg/tablet |
| --- | --- |
| Tenofovir Disoproxil fumarate | 300 |
| emtricitabine | 200 |
| Hydroxypropyl Methylcellulose | 112 |
| Lactose B.P. | 53 |
| Pregelatinized Starch B.P. | 28 |
| Magnesium Stearate | 7 |
| total: | 700 |

Drug release takes place over a period of about 6-8 hours and is complete after 12 hours.

Capsule Formulations

Formulation H:

A capsule formulation is prepared by admixing the ingredients and filling into a two-part hard gelatin or hydroxypropyl methylcellulose capsule.

|  | mg/capsule |
| --- | --- |
| Active Ingredient | 500 |
| Microcrystalline Cellulose | 143 |
| Sodium Starch Glycollate | 25 |
| Magnesium Stearate | 2 |
| total: | 670 |

Formulation I (Controlled Release Capsule):

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin or hydroxypropyl methylcellulose capsule.

|  | mg/capsule |
| --- | --- |
| (a) Active Ingredient | 500 |
| (b) Microcrystalline Cellulose | 125 |
| (c) Lactose B.P. | 125 |
| (d) Ethyl Cellulose | 13 |
| total: | 763 |

Formulation J (Oral Suspension):

The active ingredients are admixed with the ingredients and filling them as dry powder. Purified water is added and mixed well before use.

|  |  |
|---|---|
| Active Ingredient | 500 mg |
| Confectioner's Sugar | 2000 mg |
| Simethicone | 300 mg |
| Methylparaben | 30 mg |
| Propylparaben | 10 mg |
| Flavor, Peach | 500 mg |
| Purified Water q.s. to | 5.00 ml |

Formulation K (Suppository):

One-fifth of the Witepsol H15 is melted in a steam jacketed pan at 45° C. maximum. The active ingredients are sifted through a 200 micron sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 micron stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

|  | mg/Suppository |
|---|---|
| Active Ingredient | 500 |
| Hard Fat, B.P. (Witepsol H15 - Dynamit Nobel) | 1770 |
| total | 2270 |

Fixed Dose Combination Tablet

A fixed dose combination tablet of tenofovir disoproxil fumarate (TDF) 300 mg/emtricitabine 200 mg was formulated using a wet granulation/fluid-bed drying process using conventional methods. See: U.S. Pat. No. 5,935,946; L. Young (editor). Tableting Specification Manual $5^{th}$ ed., American Pharmaceutical Association, Washington, D.C., (2001); L. Lachman, H. Lieberman (editors). Pharmaceutical Dosage Forms: Tablets (Vol 2), Marcel Dekker Inc., New York, 185-202 (1981); J. T. Fell and J. M. Newton, J. Pharm. Pharmacol. 20, 657-659 (1968); US Pharmacopeia 24-National Formulary 19, "Tablet Friability", Chapter <1216>, Page 2148 (2000).

The effects of granulation water level (ranging from 40% to 50% w/w) and wet massing time were studied on the physicochemical properties of the final powder blend and its performance with respect to blend uniformity and compressibility (tablet compactibility). In addition, content uniformity, assay, stability and dissolution performance was evaluated for the TDF/emtricitabine fixed dose combination tablets.

Formulation Equipment

Equipment included a high shear mixer equipped with a pressure tank and spray nozzle tip to add the granulating water, a fluid-bed dryer, a mill, a tumble blender, a rotary tablet press, and a tablet deduster.

Formulation Process

The dried, milled powder was blended with the extragranular microcrystalline cellulose and croscarmellose sodium and then blended with magnesium stearate. Powder samples were removed after mixing with the magnesium stearate. The blend samples were evaluated for, bulk density, mesh analysis and compressibility. The powder blend mixed with the magnesium stearate was compressed into tablets on a press setup.

Materials

The following Table 1 lists the quantitative composition of the TDF/emtricitabine tablet formulation.

TABLE 1

| Ingredient | % w/w | Unit Formula for tablet cores (mg/tablet) | Quantity per 12 kg Batch (kg) |
|---|---|---|---|
| Tenofovir Disoproxil Fumarate[a] | 30.0 | 300.0 | 3.60 |
| Emtricitabine[a] | 20.0 | 200.0 | 2.40 |
| Pregelatinized Starch, NF/EP | 5.0 | 50.0 | 0.60 |
| Croscarmellose Sodium, NF/EP | 6.0 | 60.0 | 0.72 |
| Lactose Monohydrate, NF/EP[a] | 8.0 | 80.0 | 0.96 |
| Microcrystalline Cellulose, NF/EP[c] | 30.0 | 300.0 | 3.60 |
| Magnesium Stearate, NF/EP | 1.0 | 10.0 | 0.12 |
| Purified Water, USP/EP | [b] | [b] | [b] |
| Totals | 100.0 | 1000.0 | 12.00 |

[a]Actual weight is adjusted based on the Drug Content Factor (DCF) of tenofovir disoproxil fumarate and emtricitabine.
[b]Water removed during drying.

Characterization Equipment

Moisture content was measured by loss on drying using a heat lamp/balance system. The powder blend was sampled with a sampling thief fitted with chambers to determine powder blend uniformity. Duplicate samples were removed from each of several locations in the blender. Blend uniformity analysis was performed on one sample from each location.

Particle size analysis of the final powder blend was determined by sifting a multi-gram sample through a screen using a sonic sifter. The quantity of final powder blend retained on each sieve and the fines collector was determined by calculating the difference in weight between the sieves and fines collector before and after the test. The geometric mean diameter particle size was calculated by logarithmic weighting of the sieved distribution.

Bulk density was determined by filling a graduated cylinder with the final powder blend and measuring the weight differential between the empty and filled graduate cylinder per unit volume.

Tablets were characterized for friability using a friabilator, a hardness tester, a thickness micrometer equipped with a printer, and a weighing balance.

Compression characteristics were determined using a rotary tablet press equipped with a flat-faced, beveled edged punch to a target weight of 400 mg. The powder blends were compressed using target upper punch pressures ranging from approximately 100 to 250 MPa. The apparent normalized ejection force was determined and normalized for tablet thickness and diameter.

Tablet hardness was determined using a hardness tester. Tablet thickness was determined using a micrometer, and tablet weights were determined using a top loading balance.

Wet Granulation

The powders were blended in a granulator and then granulated using water. The impeller and chopper speeds were kept constant in the blender at a low setting during the granulation and wet massing operations. After water addition, the impeller and chopper were stopped and the granulator bowl was opened to observe the granulation consistency and texture. The lid was closed and the wet massing phase was performed. Acceptable granules had 40% w/w and 60% w/w water, respectively.

Wet Milling

To facilitate a uniform drying process, each wet granulation was deagglomerated with a mill fitted with a screen and an impeller. The milled wet granules were charged into a fluid-bed dryer immediately following wet milling.

Fluid-Bed Drying

Milled wet granules were dried using an inlet air setpoint temperature of about 70° C. and airflow of approximately 100 cfm. The target LOD was about 1.0% with a range of not more than (NMT) 1.5%. The total fluid-bed drying time ranged from 53 to 75 minutes. Final LOD ranged from 0.4% to 0.7% for all of the batches dried. The final exhaust temperatures for all the batches ranged from 47° C. to 50° C.

Dry Milling

All dried granules were milled through a perforated screen. The mill was equipped with a square impeller and operated. The lots were milled and manually transferred to the V-blender.

Blending

Each lot was blended using the V-blender. In one set of three formulations, starting with 12 kg materials, final powder blend yield available for compression after blending ranged from 10.5 kg (87.5%) to 11.1 kg (92.5%). The final powder blend bulk density ranged from 0.48 to 0.58 g/cc and the geometric mean diameter particle size ranged from 112 to 221 μm. Percent water and wet massing time affect final powder blend particle size and bulk density.

The powder blending for both tenofovir DF and emtricitabine gave a mean (n=10) strength value for tenofovir DF ranged from 100.6% to 102.8% of target strength for the lots and the relative standard deviation (RSD) was from 0.5% to 1.7%. The mean (n=10) strength value for emtricitabine ranged from 101.3% to 104.1% of target strength for the lots with the relative standard deviation (RSD) ranged from 0.6% to 1.7%. The final powder blend moisture level ranged from 0.8% to 1.1% LOD.

Tablet Compression

The final blends were compressed using a rotary tablet press and the tablets were film-coated.

Three 300 gm formulations (Table 2) were granulated in a granulator equipped with a 1-L bowl. The quantities of intragranular components were based on a 300 g total batch size. The formulations in lots 1 and 2 differed in the amount of microcrystalline cellulose 30% vs. 20% w/w, respectively. Lots 2 and 3 were identical except for the type of binder. Lot 2 contained 5% w/w of pregelatinized starch and lot 3 contained 5% w/w povidone as binder.

TABLE 2

| Ingredient | Lot 1 % w/w | Lot 2 % w/w | Lot 3 % w/w |
| --- | --- | --- | --- |
| Tenofovir Disoproxil Fumarate | 30.0 | 30.0 | 30.0 |
| Emtricitabine | 20.0 | 20.0 | 20.0 |
| Pregelatinized Starch, NF/EP | 5.0 | 5.0 | N/A |
| Povidone, USP/NF (C-30) | N/A | N/A | 5.0 |
| Croscarmellose Sodium, NF/EP | 6.0 | 6.0 | 6.0 |
| Lactose Monohydrate, NF/EP | 8.0 | 18.0 | 18.0 |
| Microcrystalline Cellulose, NF/EP[a] | 30.0 | 20.0 | 20.0 |
| Magnesium Stearate, NF/EP | 1.0 | 1.0 | 1.0 |
| Purified Water, USP/EP | [a] | [a] | [a] |
| Total | 100.0 | 100.0 | 100.0 |

[a] Water removed during drying.

After water addition, the impeller and chopper were stopped and the granulator bowl was opened to observe the granulation consistency and texture. To achieve similar granulation consistency, lots 1, 2, and 3 were granulated with 45%, 40%, and 30% w/w water, respectively. The lid was closed and the wet massing phase was performed. All lots had a 30 sec wet massing resulting in acceptable granulations. The wet granulations from all batches were hand screened through a sieve to deagglomerate. The resulting granulations were tray dried in a convection oven set at 60° C. for approximately 20 hours to an LOD <1.0%. The dried granulations from all batches were hand screened through a sieve. In order to fit the granulation into the small scale (300 mL) V-blender, the final blend batch size was adjusted to 100 g. A portion, 81 g of the resulting blend from Lot 1 was blended with 15 g microcrystalline cellulose, 3 g croscarmellose sodium and 1 g magnesium stearate. 86 g of the resulting granulation from Lot 2 and Lot 3 were each blended with 10 g microcrystalline cellulose, 3 g croscarmellose sodium and 1 g magnesium stearate.

Purity analysis was conducted by reverse-phase HPLC (high performance liquid chromatography). Impurities related to tenofovir disoproxil fumarate and emtricitabine were characterized and measured in the bulk API (active pharmaceutical ingredient) before formulation in the three lots of Table 2, and again after formulation in the resulting tablets. The impurities include by-products from hydrolysis of the exocyclic amino groups of tenofovir disoproxil fumarate and emtricitabine, and the hydrolysis of the disoproxil (POC) esters of tenofovir disoproxil fumarate. In each lot, the sum total of impurities related to tenofovir disoproxil fumarate and emtricitabine was less than 1% after formulation and tablet manufacture.

The physicochemical properties of tenofovir disoproxil fumarate and emtricitabine tablets were evaluated by visual appearance, water content, label strength, impurity and degradation product contents, and tablet dissolution. Stability studies were conducted on drug product packaged in container-closure systems that are identical to the intended clinical and commercial container-closure system. There was no sign of discoloration or tablet cracking during the course of the stability study. Film-coated tenofovir disoproxil fumarate and emtricitabine tablets exhibited satisfactory stability at 40° C./75% RH (relative humidity) for up to six months when packaged and stored with silica gel desiccant. No significant loss (defined as 5% degradation) in % label strength of tenofovir DF or emtricitabine was observed after six months at 40° C./75% RH. when packaged and stored with desiccant. The increase in the total degradation products was 1.5% for tenofovir DF and 0.6-0.7% for emtricitabine after six months at 40° C./75% RH when packaged and stored with 3 grams of desiccant.

All publications and patent applications cited herein are incorporated by reference to the same extent as if each individual publication or patent application was specifically and individually indicated to be incorporated by reference.

Although certain embodiments are described in detail above, those having ordinary skill in the art will clearly understand that many modifications are possible in the claims without departing from the teachings thereof. All such modifications are intended to be encompassed within the claims of the invention.

Embodiments of the Invention

A1. A pharmaceutical composition comprising an effective amount of a compound of the formula:

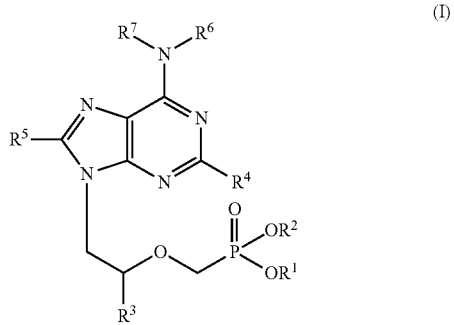

wherein $R^1$ and $R^2$ are independently selected from H, $C_1$-$C_6$ alkyl, $C_1$-$C_6$ substituted alkyl, $C_6$-$C_{20}$ aryl, $C_6$-$C_{20}$ substituted aryl, $C_6$-$C_{20}$ arylalkyl, $C_6$-$C_{20}$ substituted arylalkyl, acyloxymethyl esters —$CH_2OC(=O)R^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl and $C_6$-$C_{20}$ substituted aryl;

$R^3$ is selected from H, $C_1$-$C_6$ alkyl, $C_1$-$C_6$ substituted alkyl, or $CH_2OR^8$ where $R^8$ is $C_1$-$C_6$ alkyl, $C_1$-$C_6$ hydroxyalkyl and $C_1$-$C_6$ haloalkyl;

$R^4$ and $R^5$ are independently selected from H, $NH_2$, NHR and $NR_2$ where R is $C_1$-$C_6$ alkyl; and $R^6$ and $R^7$ are independently selected from H and $C_1$-$C_6$ alkyl;

or a physiologically functional derivative thereof;

in combination with an effective amount of a compound of the formula

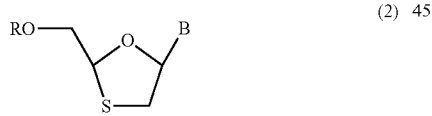

wherein B is selected from adenine, guanine, cytosine, uracil, thymine, 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, 5-fluorocytosine, 5-chlorocytosine, 5-bromocytosine, 5-iodocytosine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, and a pyrazolo[3,4-D]pyrimidine; and R is selected from H, $C_1$-$C_{18}$ alkyl, $C_1$-$C_{18}$ substituted alkyl, $C_2$-$C_{18}$ alkenyl, $C_2$-$C_{18}$ substituted alkenyl, $C_2$-$C_{18}$ alkynyl, $C_2$-$C_{18}$ substituted alkynyl, $C_6$-$C_{20}$ aryl, $C_6$-$C_{20}$ substituted aryl, $C_2$-$C_{20}$ heterocycle, $C_2$-$C_{20}$ substituted heterocycle, phosphonate, phosphophosphonate, diphosphophosphonate, phosphate, diphosphate, triphosphate, polyethyleneoxy or a physiologically functional derivative thereof; and a pharmaceutically acceptable carrier.

B2. A composition of embodiment A1 wherein, in formula 1, $R^1$ and $R^2$ are independently selected from H, $C_1$-$C_6$ alkyl, $C_1$-$C_6$ substituted alkyl, $C_6$-$C_{20}$ aryl, $C_6$-$C_{20}$ substituted aryl, $C_6$-$C_{20}$ arylalkyl, $C_6$-$C_{20}$ substituted arylalkyl, acyloxymethyl esters —$CH_2OC(=O)R^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl and $C_6$-$C_{20}$ substituted aryl; and $R^3$, $R^4$, $R^5$, $R^6$ and $R^7$ are independently H or $C_1$-$C_6$ alkyl.

C3. A composition of embodiment A1 wherein, in formula 2, B is cytosine or a 5-halocytosine.

D4. A composition of embodiment A1 wherein, in formula 1, $R^1$ and $R^2$ are independently selected from H, $C_1$-$C_6$ alkyl, $C_1$-$C_6$ substituted alkyl, $C_6$-$C_{20}$ aryl, $C_6$-$C_{20}$ substituted aryl, $C_6$-$C_{20}$ arylalkyl, $C_6$-$C_{20}$ substituted arylalkyl, acyloxymethyl esters —$CH_2OC(=O)R^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl and $C_6$-$C_{20}$ substituted aryl; and $R^3$, $R^4$, $R^5$, $R^6$ and $R^7$ are independently H or $C_1$-$C_6$ alkyl; and, in formula 2, B is cytosine or a 5-halocytosine.

E5. A composition of embodiment D4 wherein, in formula 1, $R^1$ and $R^2$ are independently selected from H, acyloxymethyl esters —$CH_2OC(=O)R^9$ and acyloxymethyl carbonates —$CH_2OC(=O)OR^9$ where $R^9$ is $C_1$-$C_6$ alkyl; and $R^3$, $R^4$, $R^5$, $R^6$ and $R^7$ are independently H or $C_1$-$C_6$ alkyl; and, in formula 2, B is cytosine or a 5-halocytosine and R is H.

F6. A composition of embodiment E5 wherein, in formula 1, $R^1$ and $R^2$ are independently selected from H and —$CH_2OC(=O)OCH(CH_3)_2$; $R^3$ is —$CH_3$; and $R^4$, $R^5$, $R^6$ and $R^7$ are H; and, in formula 2, B is 5-fluorocytosine and R is H.

G7. A pharmaceutical composition comprising a pharmaceutically effective amount of [2-(6-amino-purin-9-yl)-1-methyl-ethoxymethyl]-phosphonic acid diisopropoxycarbonyloxymethyl ester fumarate (tenofovir disoproxil fumarate) or a physiologically functional derivative thereof and a pharmaceutically effective amount of (2R,5S,)-4-amino-5-fluoro-1-(2-hydroxymethyl-1,3-oxathiolan-5-yl)-(1H)-pyrimidin-2-one (emtricitabine) or a physiologically functional derivative thereof; and a pharmaceutically acceptable carrier.

H8. A pharmaceutical formulation of embodiment A1 to G7 further comprising a third active ingredient selected from the group consisting of a protease inhibitor, a nucleoside or nucleotide reverse transcriptase inhibitor, a non-nucleoside reverse transcriptase inhibitor, and an integrase inhibitor.

I9. A pharmaceutical formulation of embodiments A1 to H8 in unit dosage form.

J10. A method for the treatment or prevention of the symptoms or effects of an HIV infection in an infected animal which comprises administering to said animal a pharmaceutical composition of embodiments claims A1 to I9.

We claim:

1. A fixed dose combination pharmaceutical dosage form comprising 300 mg tenofovir disoproxil fumarate and 200 mg emtricitabine; a binder selected from the group consisting of povidone, gelatin, hydroxypropyl methylcellulose, cellulose, microcrystalline cellulose, starch, and acacia; a disintegrant selected from sodium starch glycolate, cross-linked-povidone, cross-linked sodium carboxymethylcellulose, and alginic acid; and a lubricant selected from the group consisting of magnesium stearate, stearic acid, and talc; wherein said pharmaceutical dosage form exhibits equal to or less than 5% degradation of the tenofovir disoproxil fumarate or emtricitabine after 6 months when packaged and stored with silica gel dessicant at 40° C./75% relative humidity; and wherein said pharmaceutical dosage form is a tablet.

2. The pharmaceutical dosage form of claim 1 where there is less than 1% degradation of tenofovir disoproxil fumarate over a 24-hour period.

3. The pharmaceutical dosage form of claim 1 where there is less than 0.1% degradation of tenofovir disoproxil fumarate over a 24-hour period.

4. The pharmaceutical dosage form of claim 1 where there is less than 0.01% degradation of tenofovir disoproxil fumarate over a 24-hour period.

5. The pharmaceutical dosage form of claim 1 comprising 300 mg tenofovir disoproxil fumarate, 200 mg emtricitabine, pregelatinized starch, croscarmellose sodium, lactose monohydrate, microcrystalline cellulose, and magnesium stearate.

6. The pharmaceutical dosage form of claim 5 comprising 300 mg tenofovir disoproxil fumarate, 200 mg emtricitabine, 50 mg pregelatinized starch, 60 mg croscarmellose sodium, 80 mg lactose monohydrate, 300 mg microcrystalline cellulose, and 10 mg magnesium stearate.

7. The pharmaceutical dosage form of claim 5 comprising 300 mg tenofovir disoproxil fumarate, 200 mg emtricitabine, 50 mg pregelatinized starch, 60 mg croscarmellose sodium, lactose monohydrate, 200 mg microcrystalline cellulose, and 10 mg magnesium stearate.

8. The pharmaceutical dosage form of claim 1 comprising 300 mg tenofovir disoproxil fumarate, 200 mg emtricitabine, pregelatinized starch, croscarmellose sodium, lactose monohydrate, microcrystalline cellulose, magnesium stearate, and colloidal silicon dioxide.

9. The pharmaceutical dosage form of claim 8 comprising 300 mg tenofovir disoproxil fumarate, 200 mg emtricitabine, 50 mg pregelatinized starch, 60 mg croscarmellose sodium, 175 mg lactose monohydrate, 200 mg microcrystalline cellulose, 10 mg magnesium stearate, and 5 mg colloidal silicon dioxide.

10. The pharmaceutical dosage form of claim 8 comprising 300 mg tenofovir disoproxil fumarate, 200 mg emtricitabine, hydroxypropyl methylcellulose, lactose, pregelatinized starch, and magnesium stearate.

11. The pharmaceutical dosage form of claim 8 comprising 300 mg tenofovir disoproxil fumarate, 200 mg emtricitabine, 112 mg hydroxypropyl methylcellulose, lactose, pregelatinized starch, and 7 mg magnesium stearate.

12. The pharmaceutical dosage form of claim 1 comprising less than 1% of impurities related to tenofovir disoproxil fumarate and emtricitabine.

13. A method for the treatment of the symptoms or effects of an HIV infection in an infected animal which comprises administering to said animal the pharmaceutical dosage form of claim 1.

14. A method for the treatment of the symptoms or effects of an HIV infection in an infected animal which comprises administering to said animal the pharmaceutical dosage form of claim 8.

15. The pharmaceutical dosage form of claim 1, wherein the starch is pregelatinized starch.

16. A fixed dose combination pharmaceutical dosage form comprising 300 mg tenofovir disoproxil fumarate and 200 mg emtricitabine; a binder selected from the group consisting of povidone, gelatin, hydroxypropyl methylcellulose, cellulose, microcrystalline cellulose, pregelatinized starch, and acacia; a disintegrant selected from sodium starch glycolate, crosslinked-povidone, cross-linked sodium carboxymethylcellulose, maize starch, and alginic acid; and a lubricant selected from the group consisting of magnesium stearate, stearic acid, and talc; wherein said pharmaceutical dosage form exhibits equal to or less than 5% degradation of the tenofovir disoproxil fumarate or emtricitabine after 6 months when packaged and stored with silica gel dessicant at 40° C./75% relative humidity and wherein said pharmaceutical dosage form is a tablet.

* * * * *

UNITED STATES PATENT AND TRADEMARK OFFICE
CERTIFICATE OF CORRECTION

PATENT NO. : 9,457,036 B2
APPLICATION NO. : 14/523758
DATED : October 4, 2016
INVENTOR(S) : Dahl et al.

Page 1 of 1

It is certified that error appears in the above-identified patent and that said Letters Patent is hereby corrected as shown below:

In the Specification

Column 6, Line 18, replace "4-IV)-triazolyl," with --4-N)-triazolyl,--.

Column 6, Line 18, replace "3-N)-oxazole," with --4-(1-O, 3-N)-oxazole,--.

Column 10, Line 7, replace "(Farman" with --(Fasman--.

Column 18, Line 67, replace "[[(5)-[[(S)-1-(isopropoxycarbonyl)ethyl]amino]phenoxy" with --[[(S)-[[(S)-1-(isopropoxycarbonyl)ethyl]amino]phenoxy--.

Column 28, Line 57, replace "defined as 5%" with --defined as ≥ 5%--.

Signed and Sealed this
Twenty-fifth Day of April, 2017

Michelle K. Lee
*Director of the United States Patent and Trademark Office*